United States Patent [19]
Lewis et al.

[11] Patent Number: 6,166,366
[45] Date of Patent: Dec. 26, 2000

[54] SYSTEM AND METHOD FOR MONITORING AND CONTROLLING THE DEPOSITION OF PATTERN AND OVERALL MATERIAL COATINGS

[75] Inventors: Clarence A. Lewis, Dublin, N.H.; James Edward Lewis, Boston, Mass.; Richard Dale Lewis, Windham, N.H.

[73] Assignee: CC1, Inc., Manchester, N.H.

[21] Appl. No.: 09/120,825

[22] Filed: Jul. 22, 1998

Related U.S. Application Data

[60] Provisional application No. 60/053,519, Jul. 23, 1997.

[51] Int. Cl.[7] .................................................. H01L 27/00
[52] U.S. Cl. .................................... 250/208.1; 250/559.4; 250/559.45
[58] Field of Search ............................ 250/208.1, 559.4, 250/559.22, 559.45, 559.46; 356/237.2, 237.3, 237.4, 237.5, 239.1, 239.2, 239.7, 376

[56] References Cited

U.S. PATENT DOCUMENTS

| | | | |
|---|---|---|---|
| 4,469,440 | 9/1984 | Reich | 35/364 |
| 5,305,079 | 4/1994 | Albrecht et al. | 356/237 |
| 5,414,270 | 5/1995 | Henderson et al. | 250/559.4 |

*Primary Examiner*—Que T. Le
*Attorney, Agent, or Firm*—Kevin Mark Klughart

[57] ABSTRACT

Utilizing optical and signal processing techniques a system permitting the continuous monitoring and quality control of pattern and overall coatings applied to web materials is disclosed. Rather than using manual feedback control means to accomplish a uniform and consistent application of pattern or overall material to roll web material, the disclosed system incorporates optical sensing means along with software methodologies that enable the web material to be sampled and characterized over a number of different points. This characterization of the manufacturing process can be used with the disclosed algorithms to implement a quality control feedback mechanism which in turn can automatically correct for changes in manufacturing conditions in realtime. This permits patterns and coatings to be applied consistently without the use of human intervention and with a great reduction in overall material waste and a corresponding increase in overall coating reliability.

13 Claims, 61 Drawing Sheets

(22 of 61 Drawing Sheet(s) Filed in Color)

701

SYSTEM AND METHOD FOR MONITORING AND CONTROLLING THE DEPOSITION OF PATTERN AND OVERALL MATERIAL COATINGS

CROSS REFERENCE TO RELATED APPLICATIONS

Provisional Applications

Applicant claims benefit pursuant to 35 U.S.C. § 119 for Provisional Patent Application Ser. No. 60/053,519, filed Jul. 23, 1997 and submitted to the IJSPTO with Express Mail Label EI599262652US.

PARTIAL WAIVER OF COPYRIGHT

All of the material in this patent application is subject to copyright protection under the copyright laws of the United States and of other countries. As of the first effective filing date of the present application, this material is protected as unpublished material.

However, permission to copy this material is hereby granted to the extent that the copyright owner has no objection to the facsimile reproduction by anyone of the patent documentation or patent disclosure, as it appears in the United States Patent and Trademark Office patent file or records, but otherwise reserves all copyright rights whatsoever.

Regular Utility Applications

Applicant incorporates by reference pending Utility Patent Application entitled "SYSTEM AND METHOD FOR ZOOM LENS CALIBRATION System and Methlonitodng and Controlling the Deposition of Pattern Overall Material Coatings AND METHOD OF USING SAME", Ser. No. 08/924,595, filed in the USPTO Sep. 4, 1997, U.S. Pat. No. 6,026,172.

STATEMENT REGARDING FEDERALLY SPONSORED RESEARCH OR DEVELOPMENT

Not Applicable

REFERENCE TO A MICROFICHE APPENDIX

Not Applicable

BACKGROUND OF THE INVENTION

Overview

In the printing, converting, and coating industries ink and/or coating material is applied to a continuous web substrate either as an overall application or as a registered pattern. Variations within the materials as well as in the process itself can cause defects which can be minor and objectionable from both an aesthetic and functional point of view such as when they occur in printed images.

More serious are defects which occur in coatings that perform an important mechanical function. Two examples of coating applications in this category are:
1. Pattern coatings of cold seal (package sealants) used to provide and retain sterilization of the contents of medical instruments and supplies. Defects in the cold seal of the packaging render the contents non-sterile with serious potential for medical liability.
2. The manufacture of convertible tops with continuous overall adhesive coating. Defective or inadequate coating in the overall adhesive which binds the inside insulation to the extruded vinyl outer layer results in premature delamination with high corresponding warrantee maintenance costs. Defects in the overall adhesive coating can result in premature delamination of the outer extruded vinyl material which is exposed to the elements and which is bonded to the substrate which would be inside of the car and not subject to the elements.

While the herein described applications are shown for roll to roll processing, the same technique can be used on applications where the material is processed in sheet form.

Coating Processes

Rotogravure and flexography are the two most common coating processes that are capable of both pattern or registered coatings and are the focus of many of the exemplary embodiments of the present invention. These coating processes react similarly in regard to potential defects in coating applications. Thus, for simplicity purposes the rotogravure process will be used throughout this disclosure. A To understand how variations occur in coatings, it is first necessary to understand how coatings are applied to webs in the rotogravure coating process. A rotogravure coating unit is shown as (107) in FIG. 1 and explained as follows:
1. A cylinder (136) contains a large number of recessed engraved cells where ever the coating is to be applied to the web (146).
2. The engraved cylinder rotates in a bath of coating material contained in the coating tank (138).
3. As the engraved cylinder rotates the cells fill with coating material. Doctor blade (137) wipes off all coating that is not trapped in the engraved cells with the result that coating appears only in those areas with engraved cells.
4. Impression roller (135) exerts a large force pressing the web substrate (146) against engraved cylinder (136) whereupon the coating material is withdrawn from the cells and deposited on the web substrate in the same pattern as the etched cells.

The coating material itself is a solid which is dissolved in a suitable solvent and mixed in proportions to obtain a viscous fluid that will both fill the cells as the cylinder rotates and carry and deposit enough solid for the coating application. After the mixture is deposited on the substrate, the solvent evaporates leaving only the solid coating on the web. Generally heat is added after the mixture is deposited to increase the rate of evaporation and the speed of the process.

Types of Potential Coating Defects

For rotogravure coating applications the engraved cell dimensions are generally the same for all areas where the coating is applied. When applied correctly all coated areas are generally homogeneous or even textured. The two most common potential defects which if not corrected will cause waste are:
1. Voids that occur in the coated areas. Some of the cells in the coating areas do not transfer their coating material leaving tiny voids in areas that should contain solid homogeneous coating.
2. Too little or too much coating material being applied. The coating solvent-solid mixture contains either too much or too little solid on a volume basis.

Causes of Potential Coating Defects

Each coating application is dependent upon the density and physical dimensions of the engraved cells and the correct ratio of solvent-to-solid material. Maintaining the ideal ratio of solvent-to-solid mixture is desired if optimum coating consistency is to achieved.

However, large variations in the solvent-solid mixture are common due to the difficulty of determining the correct amount of solvent or solid needed to replenish the original supply as it is being used. Solvent is also lost due to normal evaporation especially during long downtimes of the coating machines. Attempts to control the mixture have included the measurement and control of viscosity of the mixture, the use of large enclosed coating tanks, temperature control and others.

There are a number of other factors which cause the same type of defects as variations in solvent-to-solid ratio. As illustrated in FIG. 1, these include variations in pressure of the impression roller (135) against the engraved coating cylinder (136), wear of the engraved cylinder reducing cell volume, doctor blade wear and adjustment and absorbency of the substrate.

DESCRIPTION OF THE PRIOR ART

Web Printing Overview

FIG. 1 represents a typical rotary printing machine that is used to explain the coating process for which many exemplary embodiments of the present invention are targeted. It represents all of the features required for registration of printed colors to a coated pattern including the most common rotogravure and flexographic coating process. It will be described in detail here as it will be referred throughout this disclosure.

The nonprinted material in roll form (100) proceeds through the dancer roller (102) which controls the brake (101). Dancer roller (102) provides the correct weight or tension on the web material prior to entering the first printing station (104).

The web material proceeds under printing stations (104) and (103) which print two colors on the under side of the web. The web proceeds to station (105, 106) which print two colors on the bottom of the web. Print stations (103, 104, 105, 106) are shown as flexographic printing stations. However, they could be of another printing processes including rotogravure or web offset. Print cylinder (141) is a printing cylinder including a flexographic printing plate of either rubber or photopolymer composition. Analox roller (140) is shown immersed in the ink tank (142). Ink is transferred to analox roller (140) which in turn transfers its ink to the raised image on the printing plate of printing cylinder (141). Ink on the raised image of the printing cylinder (141) is transferred to the web substrate.

The web substrate proceeds through station (107) which can apply either an overall coating, a pattern coating, or ink acting as another printing station. Station (107) is shown as a rotogravure printing station with the printing cylinder (136) immersed into ink tank (138) with doctor blade (137).

The web material proceeds through a pull station (106) which provides the correct amount of web tension throughout the printing press and arrives at the rewind (110) where the finished material is wound into a roll for later processing.

Gearboxes (113, 114, 115, 116, 117) are connected to each printing unit and drive stations (107, 106, 105, 104, 103) respectively.

Encoder (132) is attached one-to-one with the printing cylinders (136, 141). Motors (120, 121, 122, 123, 124) provide circumferential movement for registering each printing station to each other and to a pattern coating. Thus the machine in FIG. 1 provides the capability of printing colors on both sides, coating either pattern or overall by the rotogravure or flexographic process. It includes the various components of both the rotogravure and flexographic processes which are used to describe how defects can originate and propagate.

Visual Inspection Methods

FIG. 2 through FIG. 4 show the development of visual inspection over the years as coating speeds increased with the need to detect smaller and smaller defects. A portion of FIG. 1 is included in each drawing of FIG. 2–4 and noted in FIG. 2 only as coating station (FIG. 1, 107) shown as (202), pull unit (FIG. 1, 133) as (205), rewind (FIG. 1, 110) as (203). Shown also is operator (FIG. 1, 148) as (201) and substrate (FIG. 1, 149) as (204).

FIG. 2 is a completely manual and visual method of inspection by operator (201) viewing the moving web (204). This method is still largely used today, with the operator visually inspecting for defects.

As coating speeds increased and the demand to detect smaller and smaller defects, new devices were developed which aided the operator. However, the inspection process was still manual and completely visual. FIG. 3 shows one such device to aid the operator (301) visually. It consists of a series of rotating mirrors (302) which rotate one-to-one with the printing cylinder. The operator views the web (303) through the mirrors which due to their rotation appear to stop the movement of the web. Although the rotating mirrors provided a significant improvement, they were incapable of magnification and unable to discern small defects.

In FIG. 4 a video camera (404) and video monitor (405) were added to the rotating mirror device (402). The video device included a zoom lens which provided magnification. When combined with a strobe this provides very clear images on monitor (405). Thus the operator could see large areas of the substrate using the rotating mirrors and view magnified areas of the web on the monitor to view small defects. This inspection process remains substantially a manual operation requiring continuous visual inspection to be effective.

Limitations of the Prior Art

Some major limitations of these manual and visual inspection devices and methods for viewing high speed coatings include:

1. The inspection procedure varies from operator to operator with large variations in quality due to variations in operator eyesight and observation diligence.
2. The scope of inspection by a given operator is somewhat limited, and it is in general impossible to perform a full material defect detection at high material thruput rates.
3. Long intervals with no inspection may occur resulting in poor quality and undetected waste as the operator is performing other manufacturing tasks.
4. The manual visual method does not lend itself to the detection and correction of potential defects and lacks the capability of preventing material waste from occurring. Usually by the time defects are detected they are of sufficient magnitude that they cause manufacturing waste and must be removed.
5. The manual visual procedure does not provide the capability of monitoring and recording quantitative product quality.

Thus, there are a number of functional and performance deficiencies present with all existing manual/visual inspection methods. Accordingly, the present invention as per FIG. 5 teaches the replacement of the operator with an inspection traversing mechanism that automatically performs the inspection process, thus eliminating the deficiencies of the prior art.

OBJECTS OF THE INVENTION

Accordingly, the objects of the present invention are to circumvent the deficiencies in the prior art and affect the following objectives:

1. Provide for an automatic inspection process with precise predetermined automatic defect detection to produce the same consistent product quality for all operators;
2. Provide for a dedicated system that performs continuous inspection;
3. Permit complete surface inspection of web coatings and the like in some circumstances;
4. Provide for the detection of any size potential defect by using the magnification capabilities of a zoom lens;

5. Permit corrective action in a timely fashion to prevent defective material production from occurring;
6. Permit the quantification of defect size allowing the recording and storage of quality information and complete images that can be used for a number of purposes such as improving the process, verification of quality, and archiving material images for any reason where later recall may be beneficial;
7. Provide for remote location of inspection cameras where an operator may not be able to inspect the coating material;
8. Provide for inspection of both tinted and clear coating materials;
9. Permit the coating thickness to be estimated in some circumstances;
10. Permit high speed inspections of web coatings and the like;
11. Permit a manufacturing feedback control system to be implemented using the defect size and quantity information automatically gathered by the defect detection system;
12. Permit an automatic void detection system to provide for manufacturing feedback process control of impression pressure, solvent-to-solid mixture, and other process variables which may be adjusted by a typical manual printing operator;
13. Permit feedback indicia for process changes which may compensate for wear of the engraved cylinder reducing cell volume, doctor blade wear, changes in the substrate, and the like.

These objectives are achieved by the disclosed invention which is discussed in the following sections.

BRIEF SUMMARY OF THE INVENTION

This disclosure provides for automatic inspection of overall or pattern coatings applied to a continuous web substrate by taking continuous images of the moving substrate by radiation illumination of the substrate and detecting backscattered radiation images, processing these images through a variety of filter algorithms and detecting voids within the coated area of a size which if corrected prevents material waste from occurring.

The present invention solves the problem of inspecting the coating of any coating operation whether patterned or overall on tinted, and/or clear coatings, using a variety of radiation illumination sources to detect printing voids.

BRIEF DESCRIPTION OF THE DRAWINGS

The file of this patent contains at least one drawing executed in color. Copies of this patent with color drawings will be provided by the Patent and Trademark Office upon request and payment of the necessary fee.

For a fuller understanding of the advantages provided by the invention, reference should be made to the following detailed description together with the accompanying drawings wherein.

DESCRIPTION OF THE PRESENTLY PREFERRED EXEMPLARY EMBODIMENTS

Figure 1:
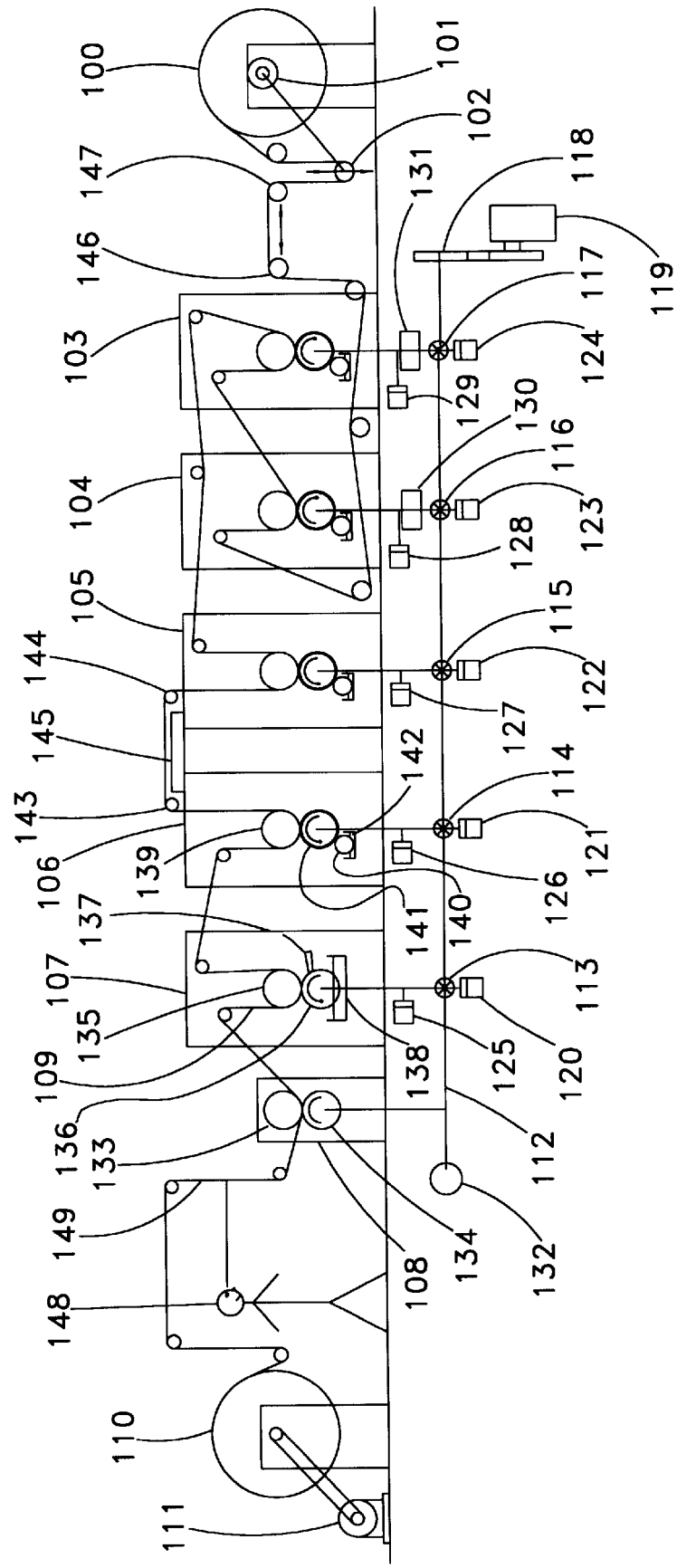
FIG. 1 illustrates a prior art general printing and coating machine.
Figure 2:
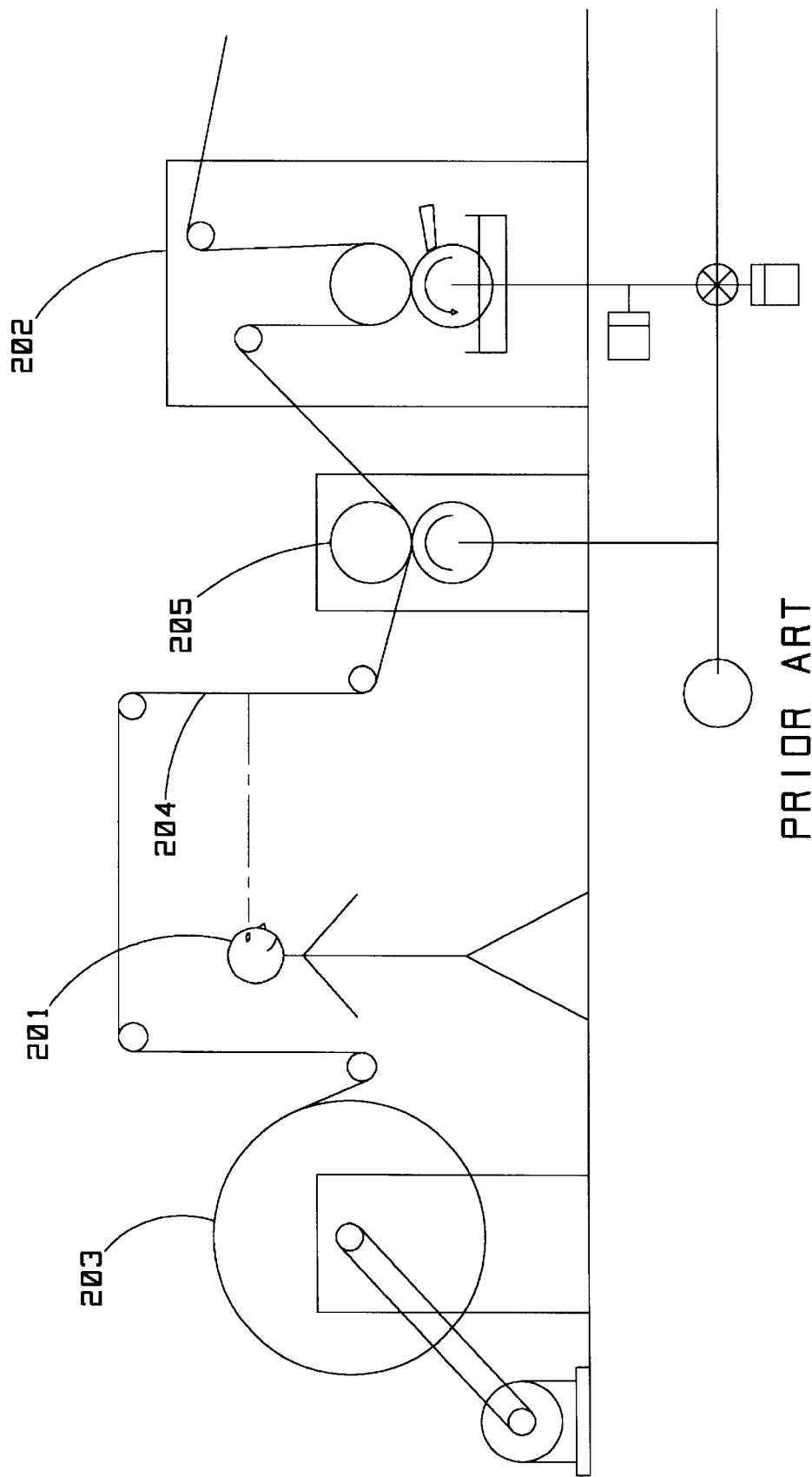
FIG. 2 illustrates a prior art manual visual inspection system for a general printing and coating machine.
Figure 3:
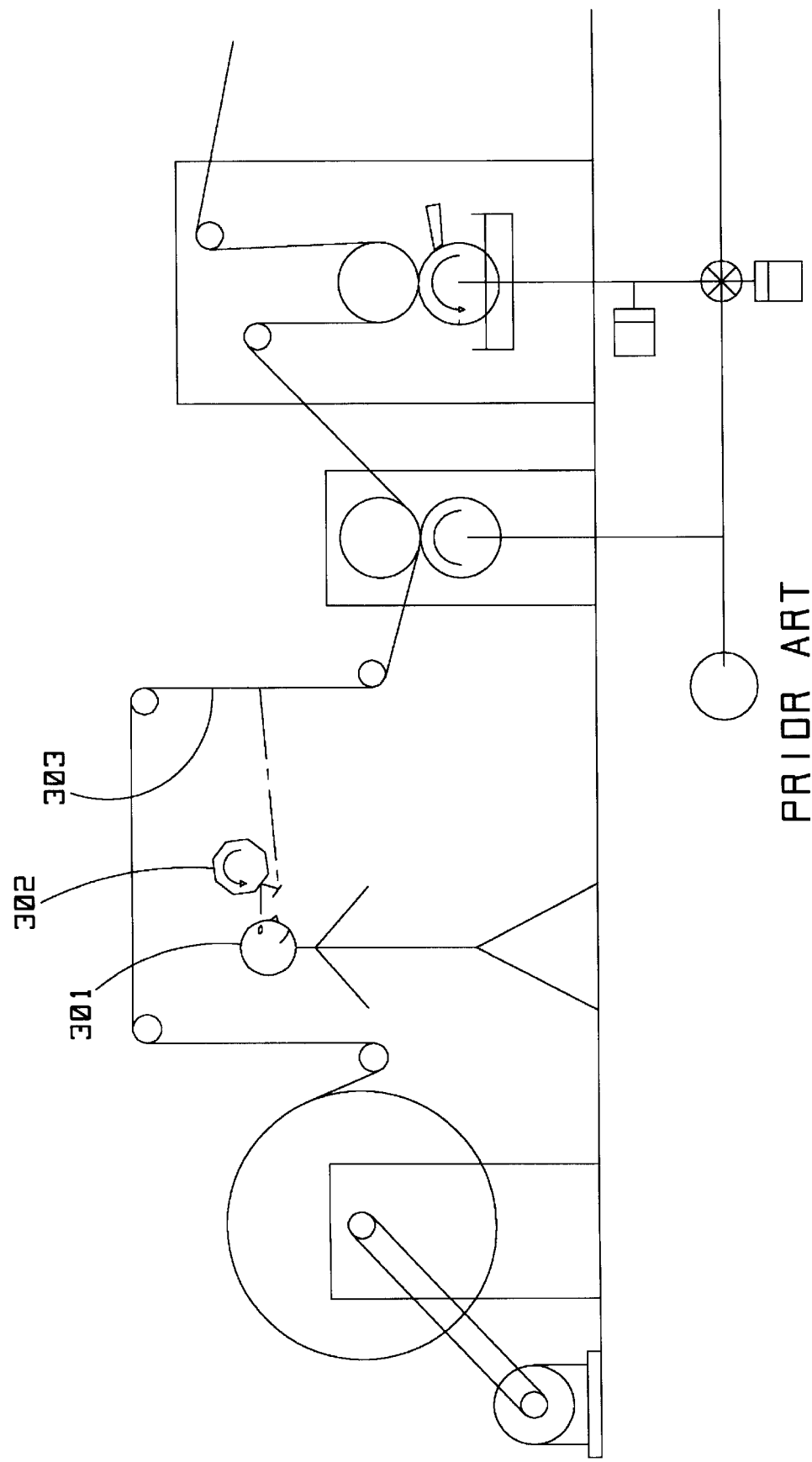
FIG. 3 illustrates a prior art manual visual inspection system for a general printing and coating machine augmented with a rotating mirror device.

While this invention is susceptible of embodiment in many different forms, there is shown in the drawings and will herein be described in detailed preferred embodiments of the invention with the understanding that the present disclosure is to be considered as an exemplification of the principles of the invention and is not intended to limit the broad aspect of the invention to the embodiments illustrated.
Text References While the following list of text references is not exhaustive, it may provide information useful to one skilled in the art to implement the teachings of the present invention in a wide variety of useful embodiments:

1. ITEX-IPL Image Processing Library Software Manual. Document Number 47-S00082-01, June 1996. IMAGING TECHNOLOGY INCORPORATED, 55 Middlesex Turnpike, Bedford Mass. 01730-1421, Tel: 617-275-2700. The image processing runtime library subroutine calls described within this document form the basis of many exemplary primitives which are used within some of the exemplary embodiments of the present invention and described herein.
2. Digital Image Processing ($2^{nd}$ Edition) by William K. Pratt. John Wiley & Sons, Inc., 1991, ISBN 0-471-85766-1.
3. Computer Vision by Dana H. Ballard and Christopher M. Brown. Prentice-Hall, Inc., Englewood Cliffs, N.J. 07632, 1982, ISBN 0-13-165316-4.
4. Computer Imaging Recipes in C by Harley R. Myler and Arthur R. Weeks. PTR Prentice Hall, Englewood Cliffs, N.J. 07632, 1993, ISBN 0-13-189879-5.
5. The Image Processing Handbook by John C. Russ. CRC Press, 1992, ISBN 0-8493-4233-3.
6. Pattern Recognition by Mike James. John Wiley & Sons, Inc., 1988, ISBN 0-471-61120-4.
7. Digital Image Processing—Principles and Applications by Gregory A. Baxes. John Wiley & Sons, Inc., 1994, ISBN 0-471-00949-0.
8. Digital Image Processing ($2^{nd}$ Edition) by Rafael C. Gonzalez and Paul Wintz. Addison-Wesley Publishing Company, 1987, ISBN 0-201-11026-1.

Disclosure Interpretation

RTP Model Numbers

Throughout this document the term 'RTP using' or similar phraseology will indicate specific manufacturers model numbers or products which have been used in embodiments of the present invention that have actually been reduced to practice or for which the model/product may be suitable for use in a preferred embodiment. This use of specific model numbers and products in no way limits the scope or teaching of the present invention to these models and/or products, but is included for informational purposes only to guide the reader so as to minimize any experimental delays which might be associated with actually constructing working embodiments of the present invention. In no way are these construction details meant to limit the scope of the claims or of the teachings of the present invention to the specific construction details given.

Radiation Detection Technology

Throughout the discussion of the exemplary embodiments of the present invention reference will be made to CCD camera technology and 8-bit color and monochrome camera systems. These references are illustrative only, and are not intended to limit the scope of the present invention to these particular technologies. The present invention may be embodied with sensor technologies have a wide variety of bits of resolution and with any number of color planes of sensitivity. Moreover, the use of CCD technology is only exemplary of a whole host of radiation sensors, detectors, and backscattering radiation detection means which may be utilized to embody variants of the present invention.

For example, the present invention specifically envisions the use of linear cameras and/or sensors for use as the radiation detector means in some embodiments of the present invention. The use of these devices may be preferred in many circumstances which require full width continuous inspection of a material coating process to maintain high quality coating laydown with minimum voids in the resulting process. This feature may be of paramount importance in some critical applications such as packaging of medical instruments and/or supplies, as well as the packaging of foodstuffs, where defects in a cold seal coating can introduce contamination into the product and render it tainted, unusable, and in some cases hazardous.

Related to the issue of radiation detection technology is the issue of radiation illumination sources. The present invention makes use of pulsed radiation sources to achieve a radiation intensity sufficient to be detected using a number of various radiation detectors. This is illustrated by exemplary embodiments using pulsed strobe, near infrared (IR), infrared (IR), and ultraviolet (UV) radiation. However, there is nothing within the present invention teachings which limits the radiation source to be that of a pulsed variety. The radiation illumination source could just as well be a source of continuous intensity. In this circumstance the radiation detector would be configured with a mechanical or electrical shutter means to capture an image at a given instant in time, much as in the way a typical radiation sensor would capture an image from a pulsed radiation source. Thus, these two methods should be considered equivalents within the context of implementing the teachings of the present invention, and no limitation on the present invention with respect to the mode of radiation illumination should be imposed by this disclosure.

Digital vs. Analog

The present invention is illustrated in exemplary embodiments which make use of digital computer systems and associated digital signal processing technologies. However, nothing in the teachings of the present invention should be construed to limit the scope of the invention teachings to solely digital systems. Analog signal processing systems are specifically envisioned by the present invention to have a place within the context of embodiments of the present invention teachings. These analog signal processing elements may take the form of smart programmed sensor arrays, neural nets, systolic arrays, or the like in which analog information is processed rather than digital information as is done with the exemplary embodiments disclosed herein. Of course, one skilled in the art will recognize that mixed digital/analog systems may be constructed using hybrids of either of these approaches.

Flowcharts

Throughout the discussion of the exemplary embodiments of the present invention, flowcharts will be used in an effort to convey major points of interest in the exemplary embodiments. These flowcharts are to be considered as exemplary, and steps shown may in general be performed in a wide range of ordering, and some steps may be present and others absent with no loss in the generality of the teachings of the present invention. Additionally, other steps may be added to the those listed with no loss of generality of the teachings of the present invention.

It is significant to note that depending on the pattern/overall coating application, the flowcharts provided may be stripped of some functionality in many circumstances and yet still achieve the overall goal of correctly detecting voids in pattern/overall coating. This is entirely to be expected, as the presently preferred embodiments that are provided are targeted towards a specific type of pattern/overall coating application. The present invention, however, has much wider application to a field of use that extends beyond traditional pattern/overall coating applications.

System Functionality

Throughout this discussion, the term 'monitoring and/or controlling the deposition of pattern and/or overall material coatings' should be interpreted in the broadest sense. That is to say, embodiments of the present invention may be constructed to monitor depositions, control the depositions, and also monitor and control depositions. These depositions should also be construed broadly, as they may include patterns, overall coatings, or combinations of the two. Depending on the target application, some embodiments of the present invention may contain some portions of the functionality described herein and others will omit these for reasons of economy or other design-related compromises.

It must be noted that an adjunct to the monitoring and/or controlling functions mentioned above is the possibility of using the void detection features of the present invention to enable security marks and/or barcode information to be embedded within tinted and/or clear material coatings. This would, for example, enable a manufacturer to incorporate bar codes within a cold seal or other material coating which is invisible to ambient light but which may be read using infrared (IR) or ultraviolet (UV) radiation. In these circumstances the present invention may be used to detect and read bar codes and other security information as well as detect undesirable voids in one or more material coatings.

Exemplary Hardware Overview

In the following description of a preferred embodiment of the present invention, digitized images are obtained from CCD cameras (charge coupled devices) and processed by computer using algorithms which have been developed specifically to detect potential defects in coating applications. When combined with high intensity pulsed radiation (light) sources, very detailed images of pattern or overall coatings can be obtained from webs coated at high speeds. For example with a pulsed light source of ten microseconds in duration, an image can be captured accurately with details as small as 0.002 of an inch.

While the use of CCD cameras and specific types of light sources mentioned herein is a presently preferred method of implementing the teachings of the present invention, there is no inherent restriction in the present invention limiting the radiation sources and radiation detectors to these specific types. For example, the present invention could be implemented with laser radiation and other forms of backscatter detectors suitable for use with this type of radiation source. Similarly, the present invention specifically teaches that radiation sources which are invisible to the naked eye (outside the visible light spectrum) are specifically envisioned to be amenable for use in embodiments of the presently invention.

Coating Applications

Figure 6:
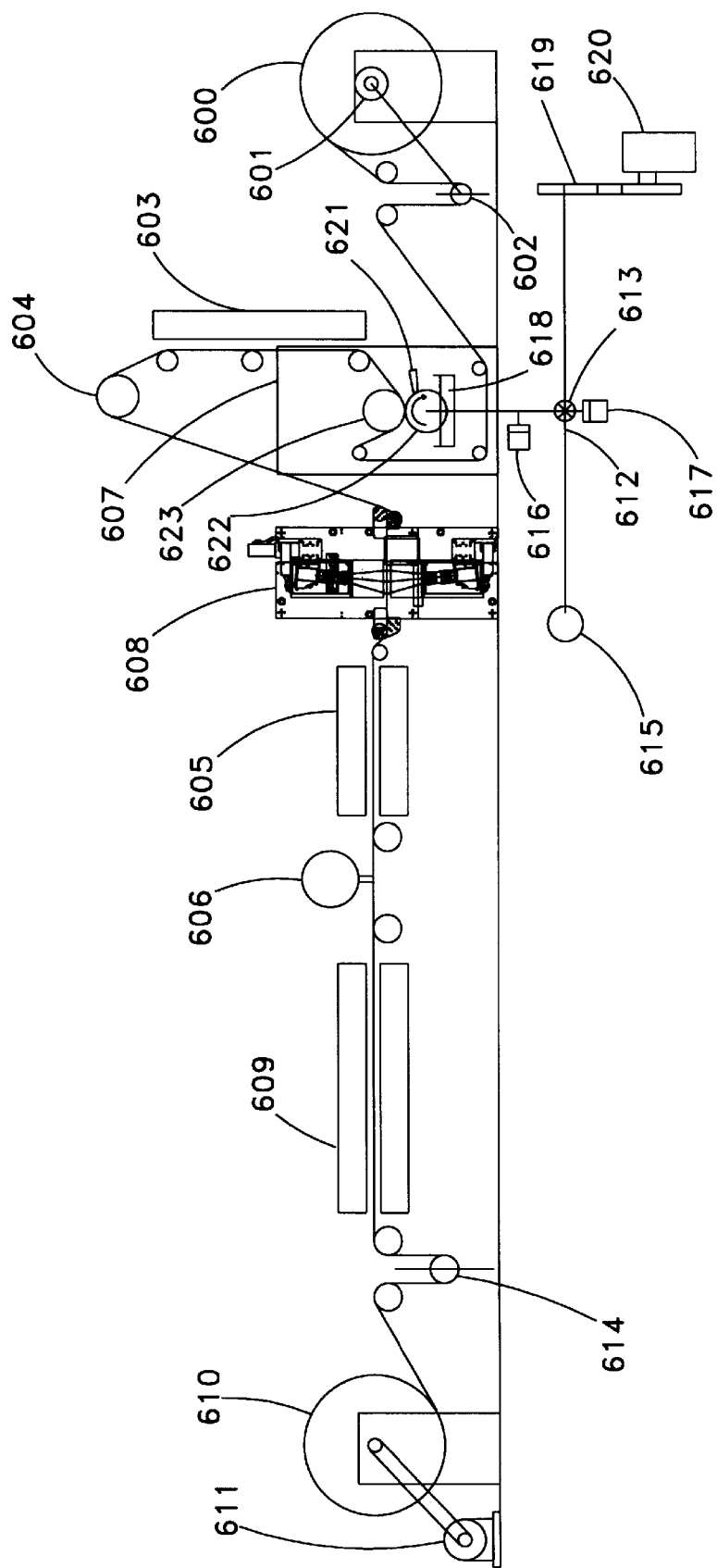
FIG. 6 illustrates application of an exemplary embodiment of the present invention in a coating and extrusion application.

FIG. 6 illustrates an exemplary embodiment of the present invention as applied to a typical coating operation such as would occur when coating either an overall or pattern adhesive to a material which is subsequently laminated to an extruded vinyl material. Such an operation would be used in the manufacture of the material used in automobile convertible tops.

In this example the material in roll form, (600) is coated and proceeds through the coating unit (607) either overall or a pattern coating according to the pattern etched on rotogravure cylinder (621). After coating the material goes through dryer (603) for curing. It then goes through a camera traversing mechanism (608) (RTP using a two camera system) where images are obtained that are processed according to the teachings of this invention. The material continues through another dryer (605) and then received an overall vinyl coating through the extruder (605). The material continues through post dryer (609) and is then rewound into rolls (610).

The coating is tinted and when applied on the white substrate, areas without sufficient coating become visible. With manual visual inspection by the time that these white areas become visible the material must be removed and is considered manufacturing waste. If defective material is not detected, it can cause premature delamination in the final product.

The major thrust of many of the disclosed embodiments of the present invention is to monitor the coating and determine the potential white show-through using magnification and the herein taught software methods. The use of encoder (615) enables the entire repeat areas of the cylinder equal to its circumference and width to be inspected with appropriate movements of the traversing mechanism and activation of the pulsed radiation source (RTP using a strobe, LED IR source, and the like).

Figure 7:
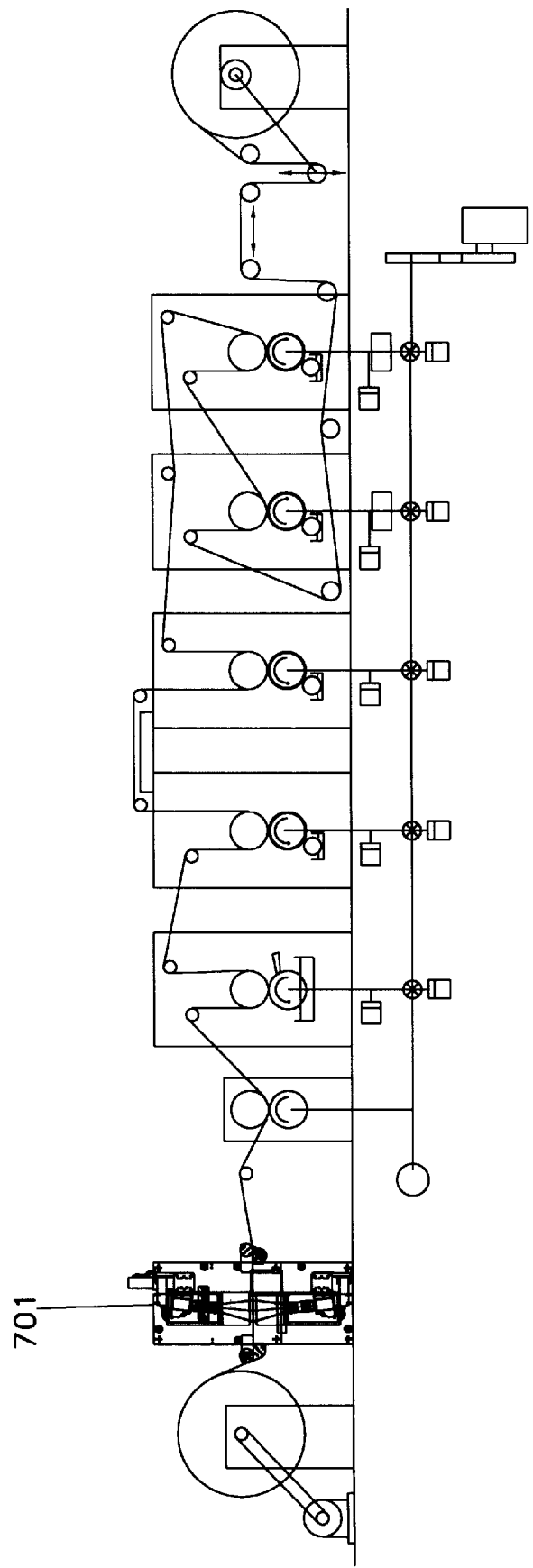
FIG. 7 illustrates application of an exemplary embodiment of the present invention in a general printing and coating machine.

FIG. 7 is the same machine as FIG. 1 but with the operator replaced by the two camera traversing mechanism (701) where images are obtained that are processed according to the teachings of the present invention.

Figure 8:
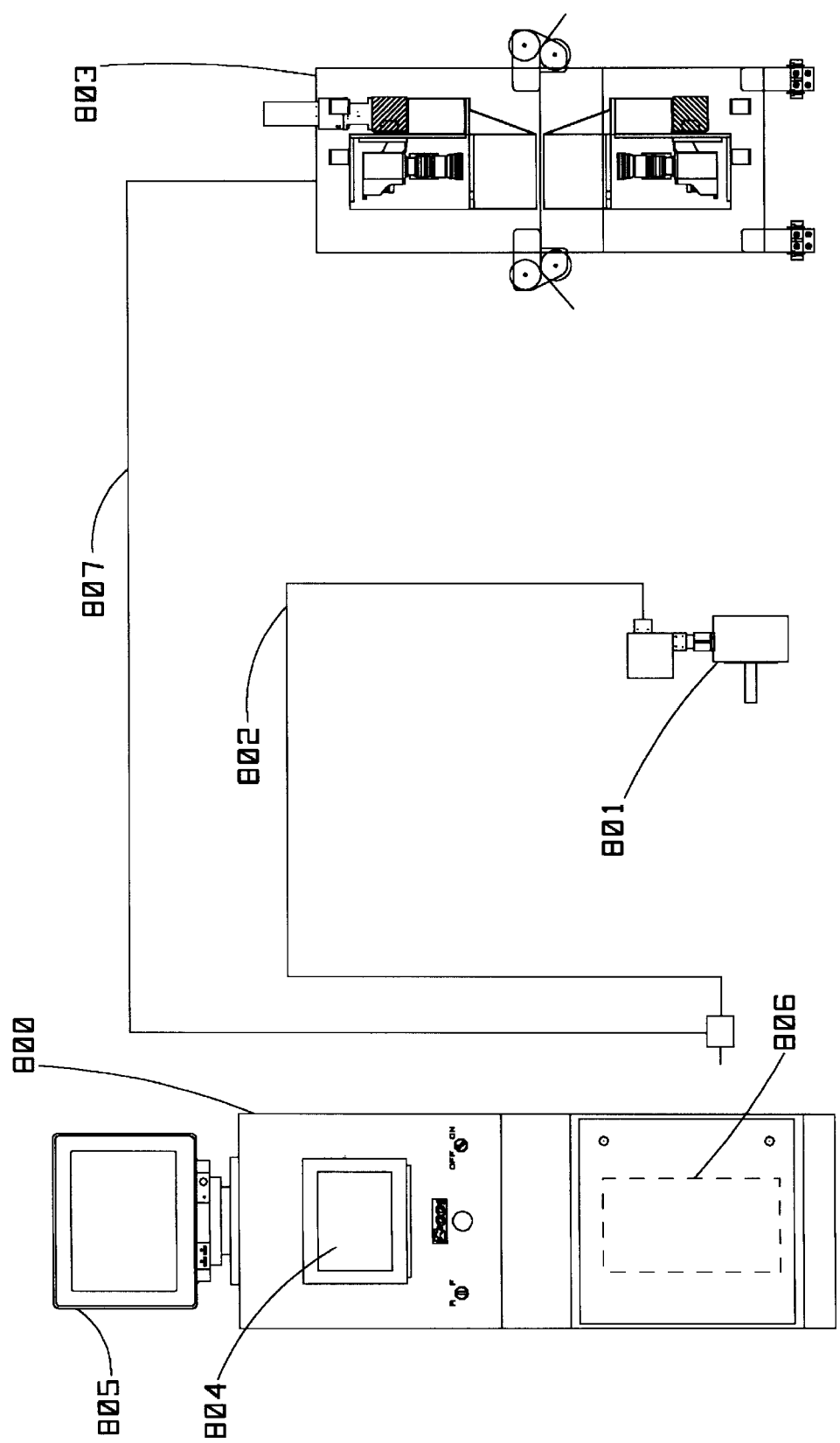
FIG. 8 illustrates a schematic of the major system components of an exemplary embodiment of the present invention.

FIG. 8 illustrates an exemplary embodiment of the typical components of a complete deposition monitoring system which includes a camera traversing mechanism (803) electrically connected to the console containing monitor (805) (RTP using Mitsubishi TRW91055KTK), touch screen (804) (RTP using Elographics 2740A-131), and image processing computer (806) (RTP using Avnet-Portland 266). Encoder (801) provides the information necessary to encode the circumference of the coating cylinder enabling images to be taken at any position around the circumference. A wide variety of encoders are available and suitable for this purpose.

Figure 5:
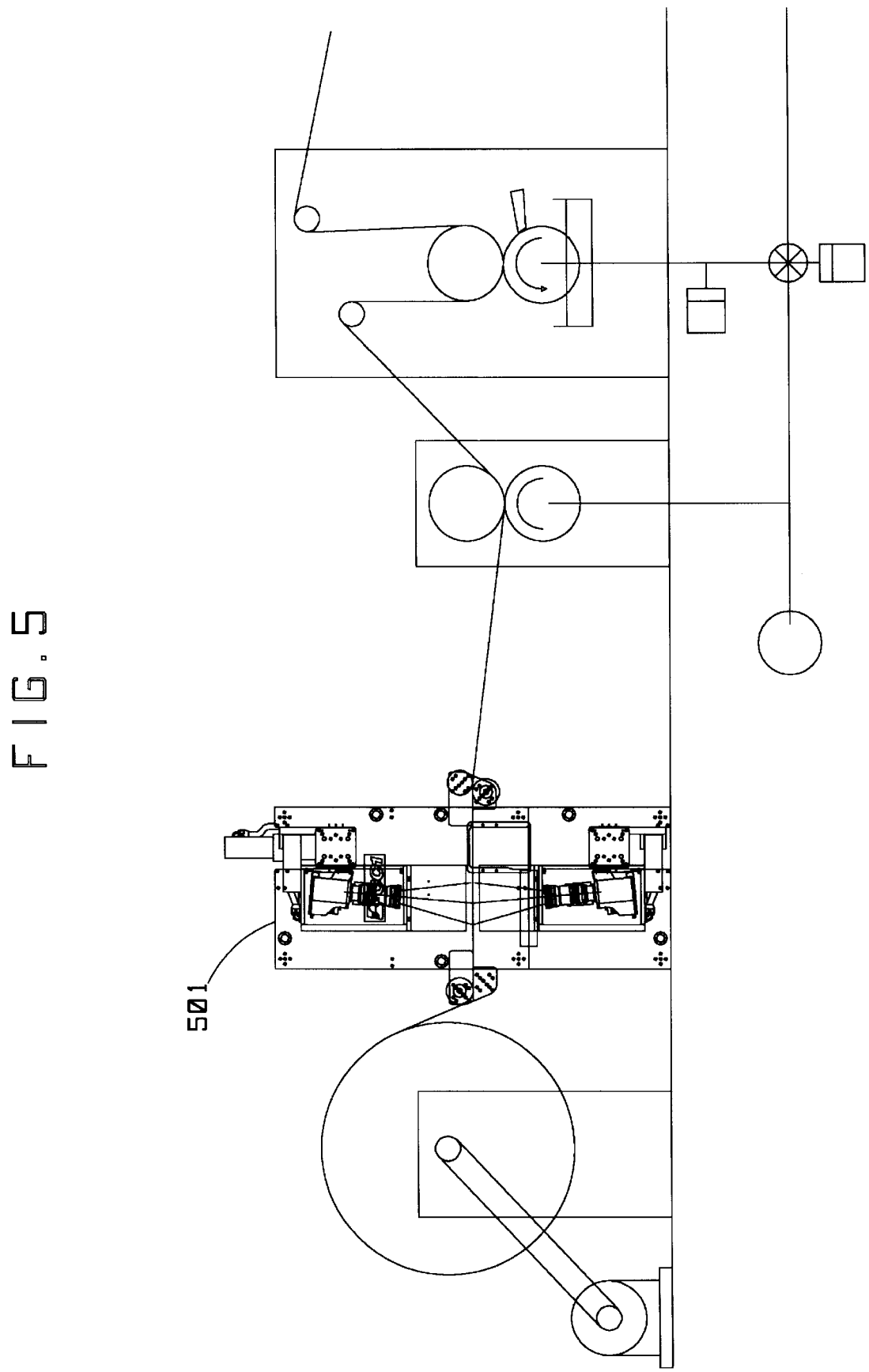
FIG. 5 illustrates replacement of the manual operator inspection with an exemplary embodiment of the automatic inspection system/method taught by the present invention.
Figure 9:
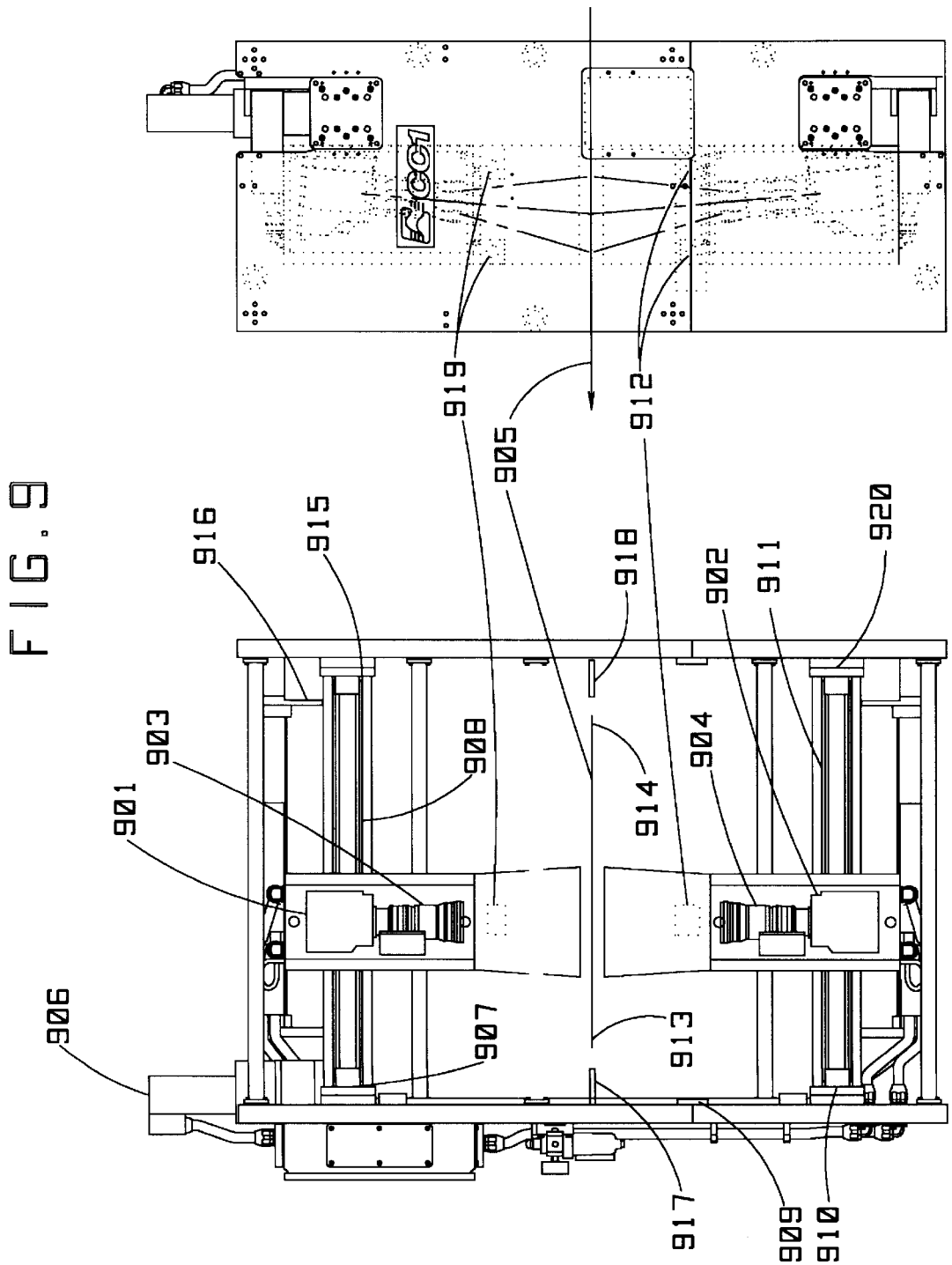
FIG. 9 illustrates a two camera traverse system used in an exemplary embodiment of the present invention.

FIG. 9 illustrates a more detailed drawing of an exemplary embodiment using a two camera system shown as (501) FIG. 5, (608) FIG. 6, (701) FIG. 7 and (803) FIG. 8.

Two cameras (901) and (902) are mounted for viewing either side of the printed or coated web substrate (905). Zoom lens (903) is attached to camera (901) and zoom lens (904) is attached to camera (902). The zoom lens may be a commercially available motorized unit such as manufactured by Fujinon (RTP using S16X6.7BMD-18) or Cannon (RTP using J10x10R-II) with a 16 to one zoom ratio. Note that other zoom ratios may also be used. The cameras (901, 902) are commercially available from a wide variety of manufacturers (RTP using DXC 950P). A DXC 950P camera is preferred in many embodiments as it is the highest resolution camera available using 3CCD chips which provide full RGB (Red, Green, Blue) color. Cameras (901) and (902) are mounted on traversing mechanisms (908) and (911). Each traverse includes a belt with a sprocket at each end. For traverse (908) the sprockets are shown as (907) and (915) for traverse (911) as (910) and (920). Both cameras can move laterally driven by motor (906) (RTP using Bison 507-01-106A) through drive shaft (909) which mechanically connects sprockets (907) and (910) allowing both cameras to be mechanically connected that is desirable when viewing front to back register on opaque substrates. While two motors could be supplied enabling each camera to be positioned separately, there are a number of advantages of mechanically linking both cameras which will become evident in this application.

Optical encoder (916) (RTP using DRC HD2F10E1B6SC-1024) is attached to sprocket (915). The number of counts per revolution of the encoder is selected at 1000 counts per revolution in many preferred embodiments which enables encoding the lateral position of the cameras to within 0.001 inch which is sufficient for this application. Of course, other encoding resolutions are well within the scope of the teachings of the present invention, as the encoder resolution is a function of the coating application to which the teachings of the present invention are applied.

In the exemplary embodiment of FIG. 9, the two cameras when connected to the computer to be described enables the cameras to be positioned through appropriate software to any lateral position over the entire range of the traverse to within 0.001 inch. For this application the lateral position will hereafter be represented by X with 0 starting from the left furthermost position of the traverse with the maximum travel of the traverse represented in thousandths of an inch (mils). These are fixed positions to which the traverse is always calibrated when power is applied.

Image Acquisition and Computer Interface

Figure 10:
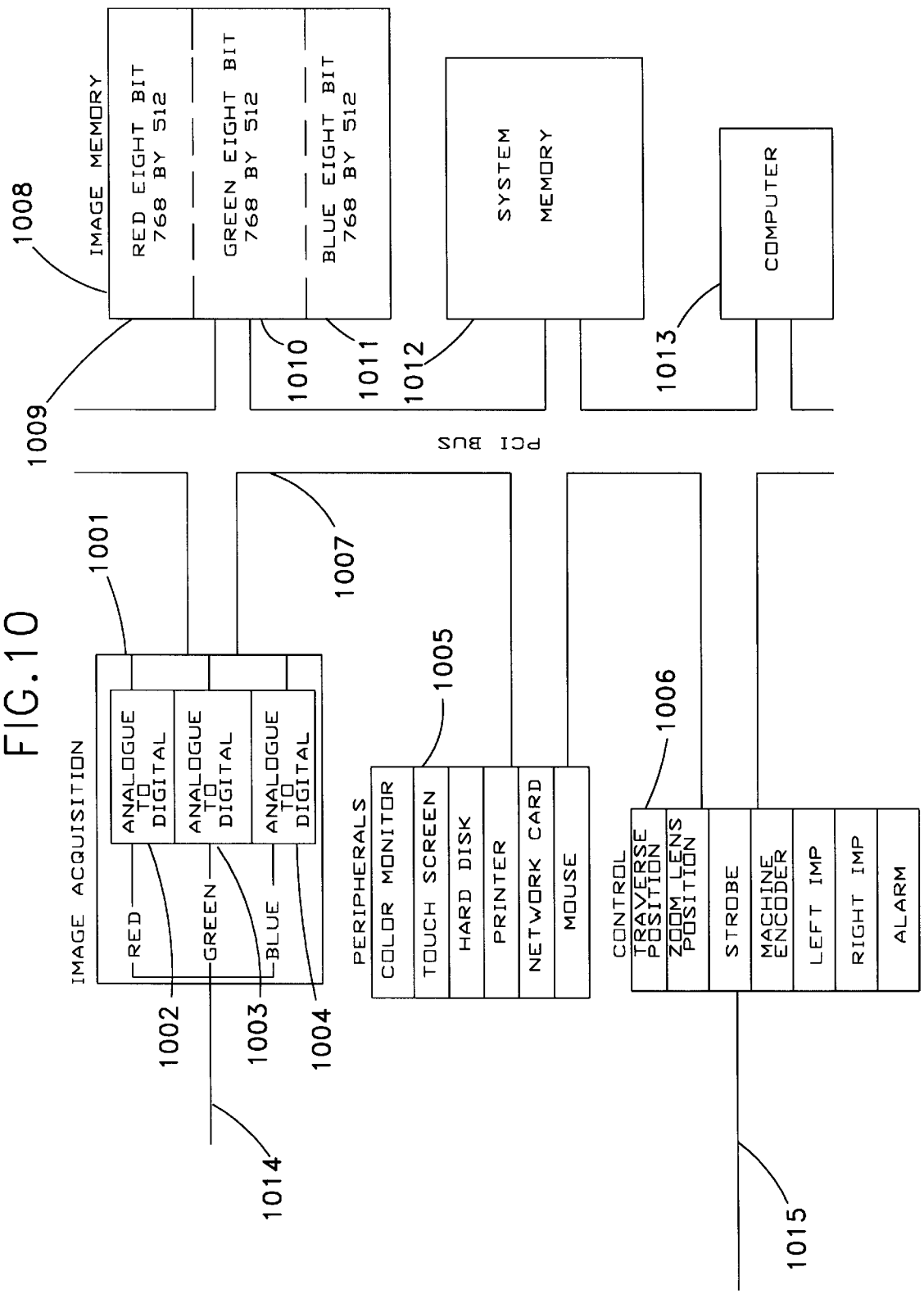
FIG. 10 illustrates a block diagram of the computer interface used in an exemplary embodiment of the present invention.

FIG. 10 is a schematic representation of the computer interface to all components associated with an embodiment of the invention which together provide
1. a means to obtain images at any zoom position in any areas of the complete repeat length as defined by the web width and cylinder circumference; and
2. a means to analyze these images for variations and potential defects in coating applications.

In a preferred embodiment of the present invention, the computer system illustrated in FIG. 10 is a standard personal computer (1013) (RTP using an Intel Corporation with a 233 MHz Pentium II MMX processor) operating on the high speed PCI bus (1007). While a wide variety of computer system hardware configurations are possible, many of the presently preferred embodiments utilize systems with significant main memory (RTP using 128 MB or more of system memory) to accommodate the large number of images which may be quite large (RTP using 768×512× 3×8-bit images which consume 1.2 MB per image). These large memory configurations in conjunction with a suitably fast processor enable 2–3 second processing times to determine whether voids are present in the captured image. This processing thruput is an important aspect of any practical automated void detection system, as web material (generally 4 feet wide) typically moves at a rate of 1000 feet/minute past the void detection station. Long processing delays in this situation can therefore result in significant material waste.

The computer processor (1013) controls all of the electromechanical components listed in (1006) which provide images as required for analysis. These controls are of conventional design including bus controlled stepper motor drivers for positioning the traverse, digital-to-analog (D-to-A) converters for positioning the zoom lens, machine encoder and strobe driver all controlled through the PCI bus from instructions stored in the hard disk of peripherals (1005). An image acquisition board (1001) (RTP using an IMAGING TECHNOLOGY of Bedford Mass. Model IMPCI with software ITEX-IPL) captures images, digitizes them and sends them into the computer image memory (1008) as Red, Green and Blue planes for processing.

System Overview

Figure 11:
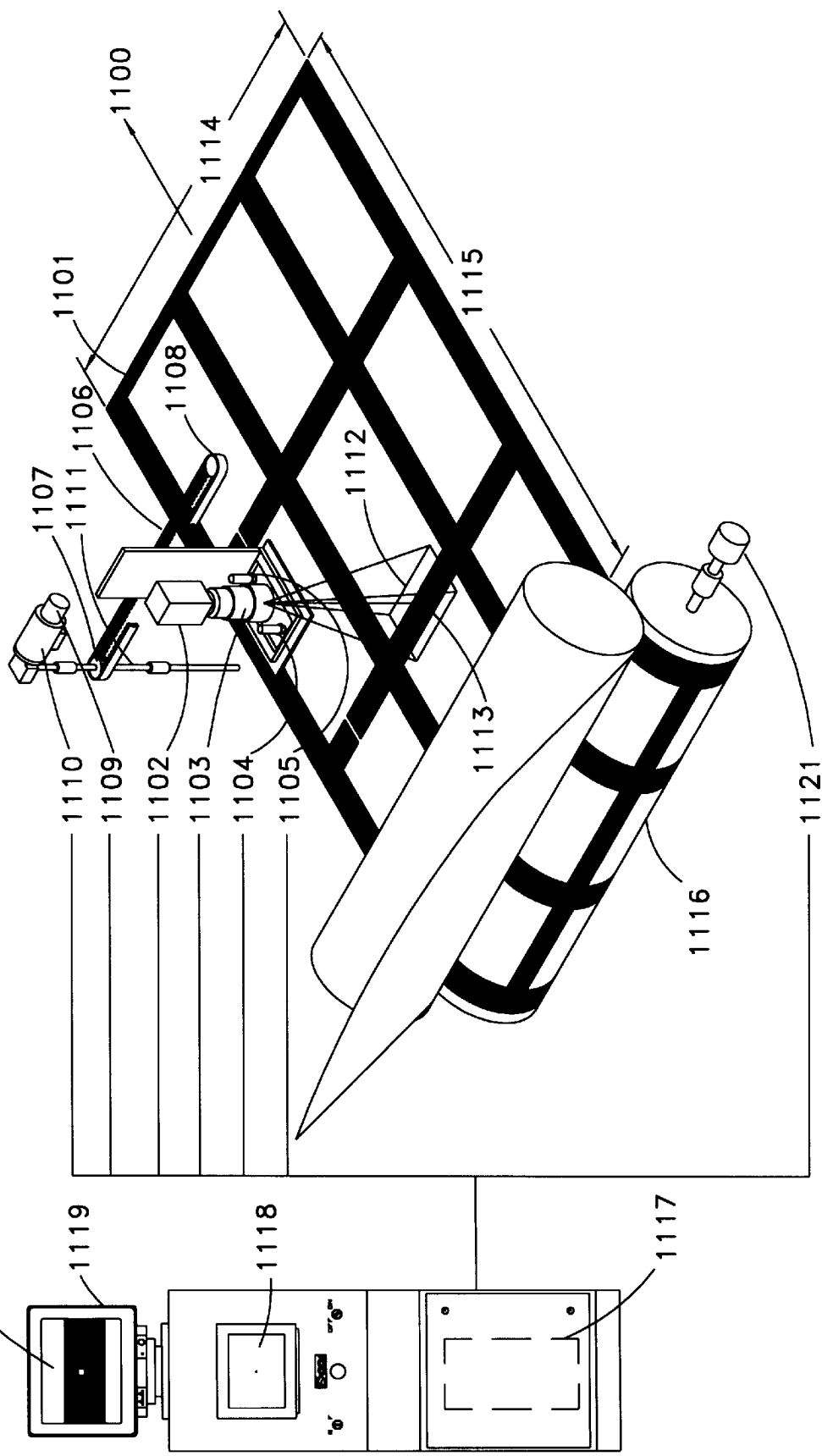
FIG. 11 illustrates an exemplary embodiment of the present invention applied to a tinted printing application.

FIG. 11 illustrates and exemplary embodiment of the present invention showing how the various components that have been described in detail operate together to implement some of the teachings of this disclosure. The tinted pattern coating (1100) (shown here as black) is deposited on a white substrate with a width (1114) and repeat length (1115) that is equal to (πxD) where D represents the diameter of the coating cylinder (1116). Note that while a white substrate is the focus of this example, nothing in the teachings of the present invention limits the application of the present invention to this specific type of substrate.

Traverse (1116) includes a camera (1102) (RTP using a 3-chip CCD camera), zoom lens (1003) and radiation source (1104) and (1105) (RTP using EG&G FXD-855 strobes). Traverse (1116) can move across the entire web width (1114) driven by motor (1109) with position encoder (1110) through timing belt (1106) and sprockets (1107) and (1108). Encoder (1121) provided the signal which triggers the radiation source (RTP using a strobe firing circuit) for a short duration at which time the radiation source is backscattered (RTP using strobe reflections) from the image impinges on the pixel elements of the red, green, and blue CCD devices in the camera and are represented by electrical charges or voltages. These charges are converted to digital numbers through A-to-D converters located on the image acquisition board (RTP using an IMAGING TECHNOLOGY of Bedford Mass. Model IMPCI). Once acquired, the backscattered radiation images are then stored in the computer for further processing on computer (1117). Image are displayed on monitor (1119) with image (1120) shown and taken by camera (1102) noted at (1112). Image (1120) shows the significance of the zoom lens which provides magnification clearly showing the void in the deposition process. Touch screen (1118) is the operator interface providing greatly simplified operation through a graphical interface.

Note the exemplary system embodiment as illustrated in FIG. 11 provides for the inspection of tinted cold seal as it may be implemented using conventional strobes, and a 3CCD color camera.

Coating Additives Which Provide Areas For Segmentation

The exemplary embodiment of FIG. 11 provides for the inspection of tinted cold seal as the system illustrated may be implemented using conventional strobes and a 3CCD color camera. In this exemplary embodiment the tinted cold seal provides a means for segmentation of only those areas where coating should be applied.

Tinting of the deposition coating material represents only one of many additives which may be incorporated into the coating material. There are other additives which when added to the coating material can provide a similar defined area for the segmentation methods taught by the present invention. One such additive is a chemical which when added to the coating material provides fluorescence when excited by certain incident radiation wavelengths. This fluorescence phenomenon occurs in both the UV and near IR range of the spectrum, and may be applied to other ranges of radiation as well. The technique of segmentation is the same for both UV and near IR with the light sources and filters being quite different for each application. For purposes of illustrating the teachings of the present invention, the following discussion will describe how the technique of segmentation is applied to coating material with optical brighteners that provides fluorescence when excited by UV light and near infrared. Of course, one skilled in the art will have no trouble applying these teachings to other radiation wavelengths.

UV Fluorescence

Figure 12:
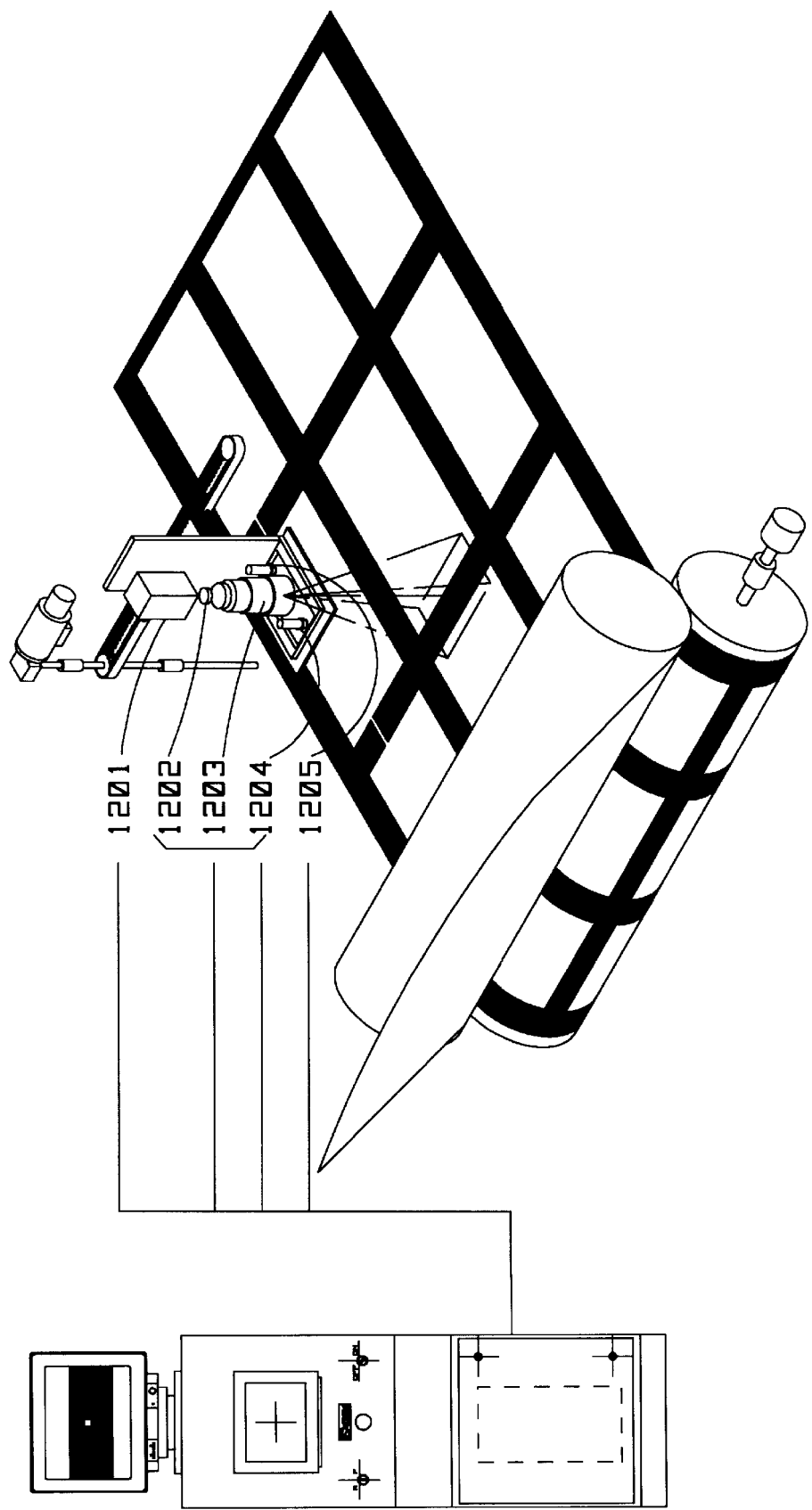
FIG. 12 illustrates an exemplary embodiment of the present invention applied to a printing application in which ultraviolet (UV) radiation is used as the illumination radiation source for clear printing.

Optical brighteners can be added to coating material that can be observed with a black light (UV light source from 320 to 380 nanometers. This method has been used in the past largely for visual inspection. FIG. 12 shows the system where the segmentation means of this disclosure can be used for automatic inspection in the same manner as with the system of FIG. 11 using tinting as the means to create an area of segmentation.

Figure 4:
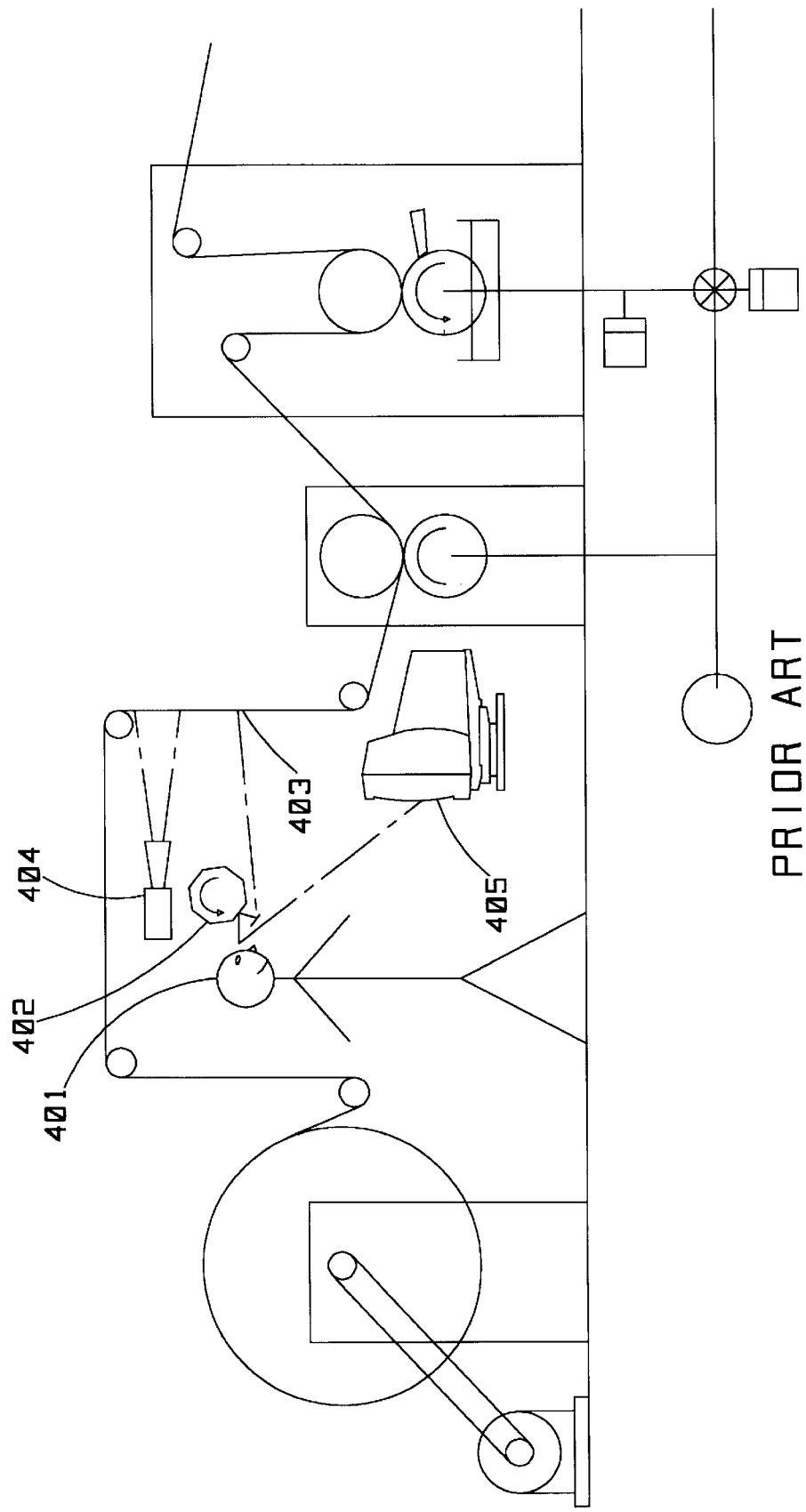
FIG. 4 illustrates a prior art manual visual inspection system for a general printing and coating machine augmented with a rotating mirror and video device.

The differences between FIG. 11 an FIG. 12 are the strobe tubes, camera and the addition of a filter. Specifically in FIG. 12 the 3CCD color camera (1102) of FIG. 11 has been replaced by a single CCD black and white camera (1201) (RTP using Sony Model XC-75CE). The strobe tubes (1104, 1105) illustrated in FIG. 11 4 have been replaced by the same tubes but with quartz glass enclosures (RTP using EG&G of Salem, Mass. model FXQ-855). Up to about 30 percent of the total light output from a quartz Xenon flash tube is in the 320 to 380 nanometer range. Each fluorescence optical brightener may will peak in a specific frequency requiring a bandpass filter centered at this frequency to magnify the affect of florescence. The filter shown in FIG. 12 (1202) is typically a bandpass filter from 360–520 nanometers which would cover the areas where fluorescence is most common (RTP using Oriel Corporation of Stratford, Conn. bandpass filter model numbers 51660-51725).

Near Infrared Fluorescence
Clear Coating Applications

There are coating applications where a clear cold seal coating is required for sealing. An example is when a cold seal is used on a clear plastic packaging material where tinting would be objectionable. For these clear coating applications there has until now been no solution for either manual visual viewing or automatic inspecting on a moving web. The solution to this problem is taught by another embodiment of the present invention which utilizes coating additives which are clear when exposed to visible light, but which may be excited to emit visible light when radiated with other forms of radiation.

Exemplary Coating Additive

An embodiment of the present invention utilizing this technique has been demonstrated using a commercial clear coating additive (RTP using Eastman Chemical company of Kinsport, Tenn. additive sold under their trade name NIRF 1100 Dispersion). When added in small quantities to the coating material, it will fluoresce at a wavelength centered around 720 nanometers when illuminated with a light source centered around 680 nanometers. This range is well within the sensitivity of a CCD camera enabling the use of one of the methods of segmentation taught by the present invention.

Exemplary Embodiment

Figure 13:
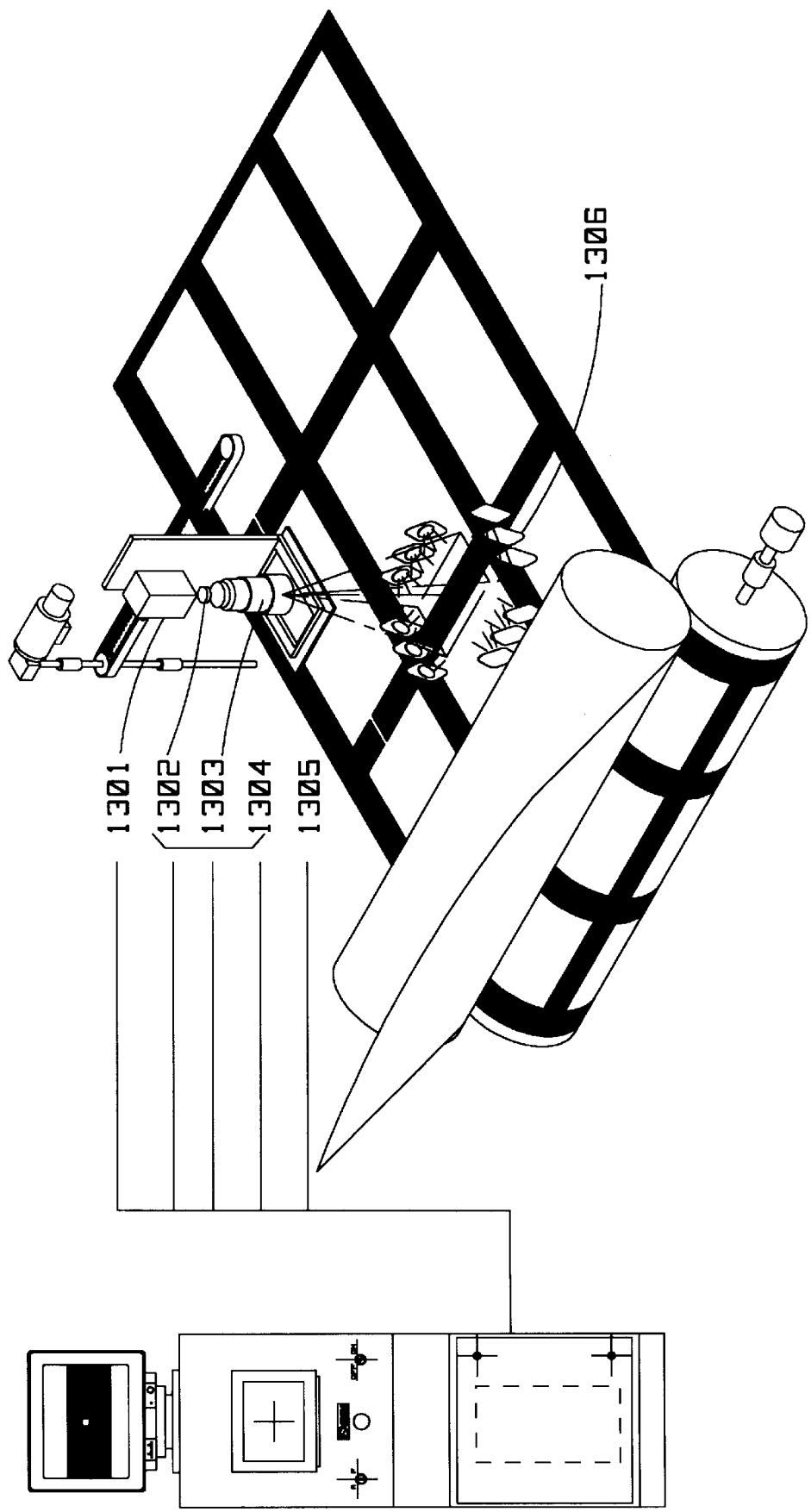
FIG. 13 illustrates an exemplary embodiment of the present invention applied to a printing application in which infrared (IR) radiation is used as the illumination radiation source for clear printing.

FIG. 13 illustrates an embodiment of a system where the segmentation means taught by the present invention can be used for automatic inspection in the same manner as with the system of FIG. 11 using tinting as the means to create an area of segmentation. Camera (1301) (RTP using Sony Model XC-75CE) is typically implemented as a single CCD chip black-and-white camera. Infrared (IR) light emitting diodes (LEDs) (1305) are used as the radiation source and may be obtained from a variety of manufacturers (RTP using Opto Technology Co. of Wheeling Ill. their Model OTL680A-9-4-66-E). Filter (1302) is manufactured by Oriel Instruments of Stratford, Conn. their model 51340 which has a cut-on wavelength of 695 nanometers. Thus, light at the excitation frequency of 680 manometers will excite the molecules of the coating additive (RTP using Eastman Chemical NIRF 1100 Dispersion). This will fluoresce the coating a frequency of 715 manometers. The cut-on filter allows only radiation above 695 manometers and providing a gray scale image with the fluoresced areas that are also coated brighter enabling segmentation and automatic inspection according to teachings of the present invention.

IR LED Pulsed Radiation Source

Figure 14:
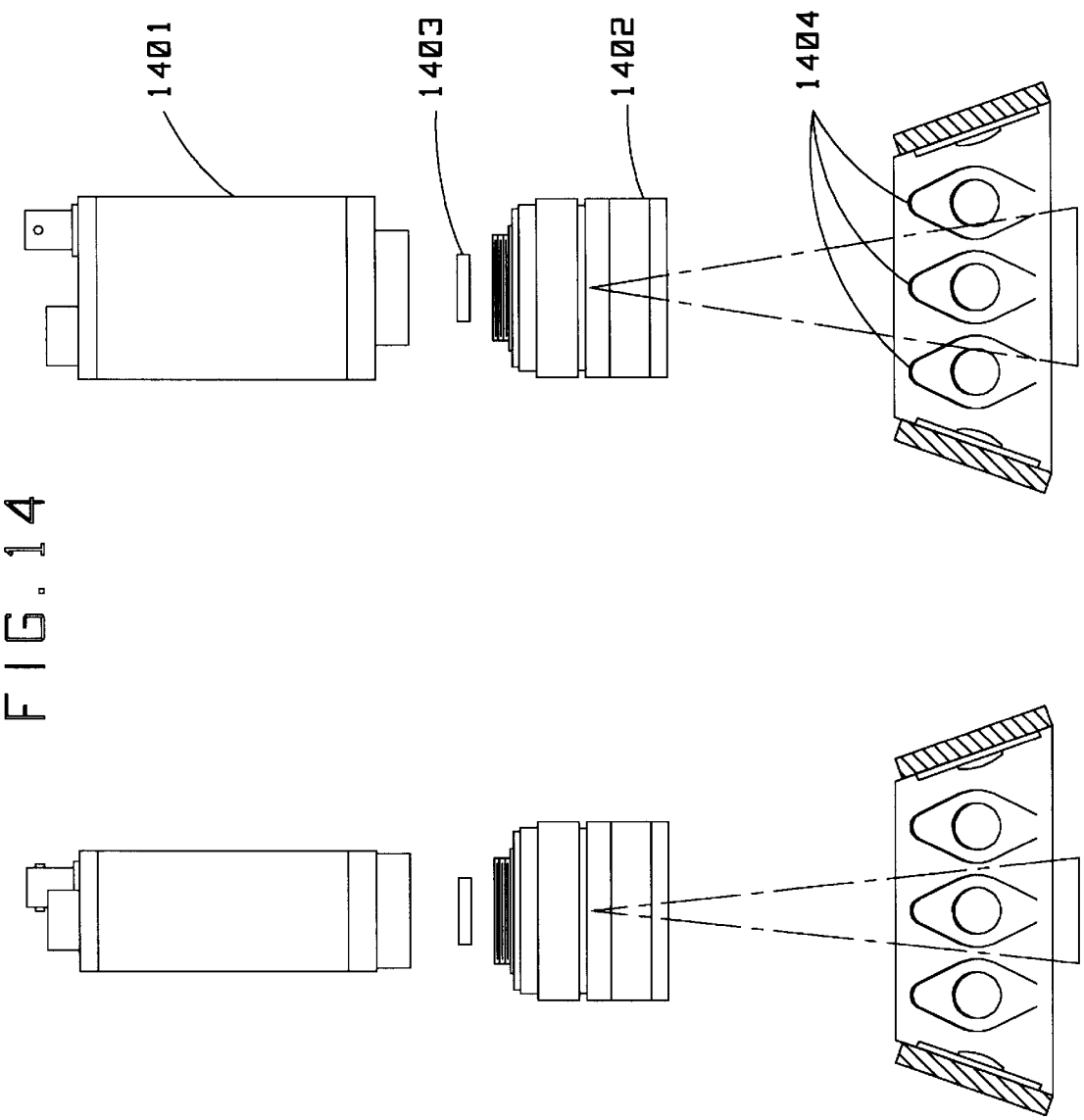
FIG. 14 illustrates a side view of the camera, lens, filter, and IR illumination array used in an exemplary embodiment of the present invention.

The pulsed LED radiation source (1306) illustrated in the exemplary embodiment FIG. 13 is quite different from a Xenon flash tube as is the circuitry required to energize the LEDs. FIG. 14 shows the camera (1401), filter (1403), lens (1402) and one assembly of three LED radiation sources (1404). Three of the LED radiation sources are arranged on each side and surround the field of view for a total of 12 LED radiation sources (RTP using a quadrature lighting arrangement).

Figure 15:
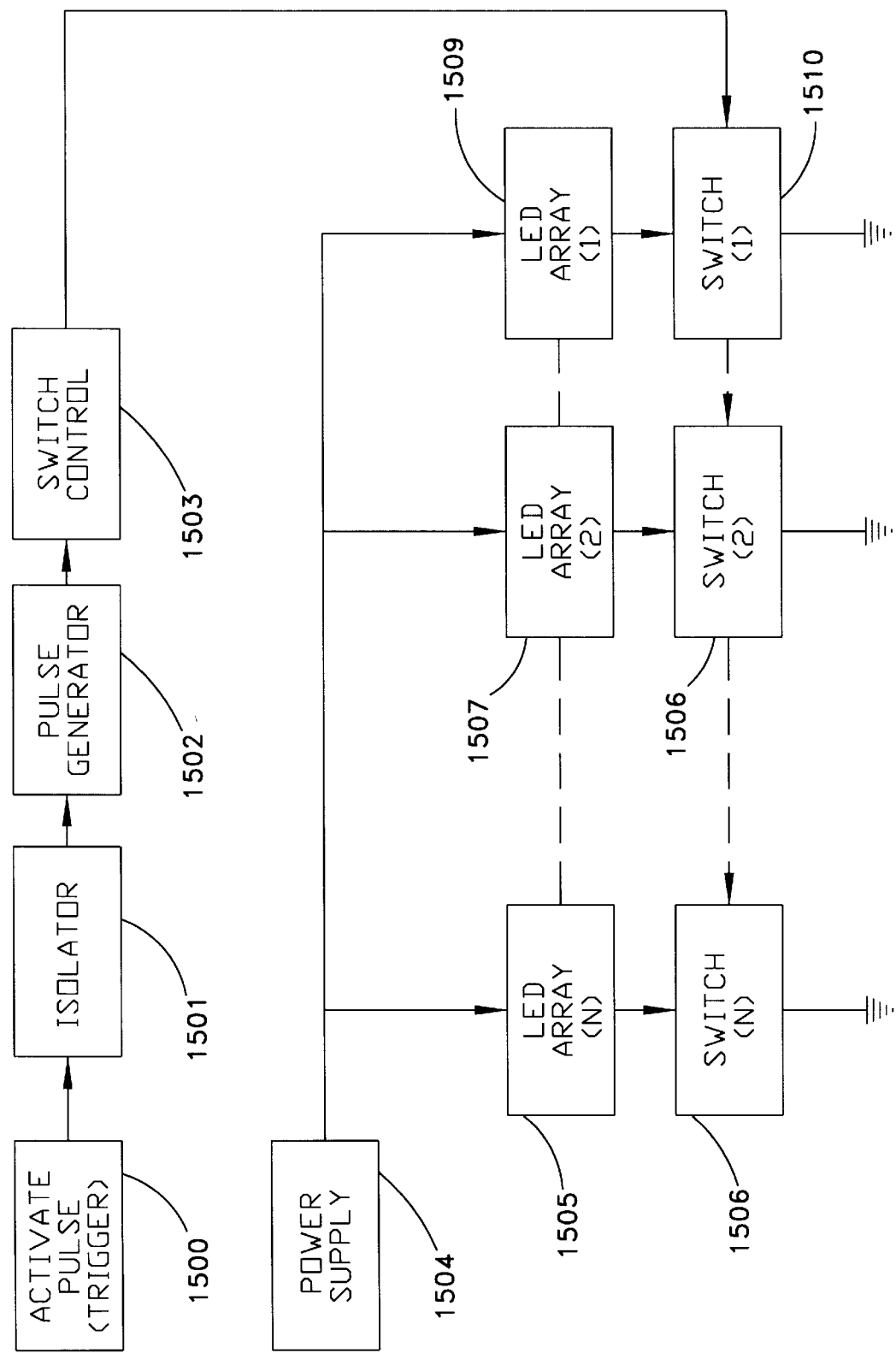
FIG. 15 illustrates a system block diagram of an exemplary embodiment of the IR LED illumination circuitry used in an exemplary embodiment of the present invention.

FIG. 15 is a schematic representation of the procedure to energize the LED radiation sources. An activation pulse (1500) is first generated from an encoder signal that indicates when the LED's should be energized. This pulse goes through an optical coupler (1501) (RTP using Motorola MOC8030) to isolate the pulse circuitry from the firing circuitry. The output of (1501) energizes a pulse for a predetermined length which is the on time of the LED sources. Any number of LED arrays can be energized from the output of switch control (1503). Power supply (1504) provides the power required to obtain the pulsed light.

Figure 16:
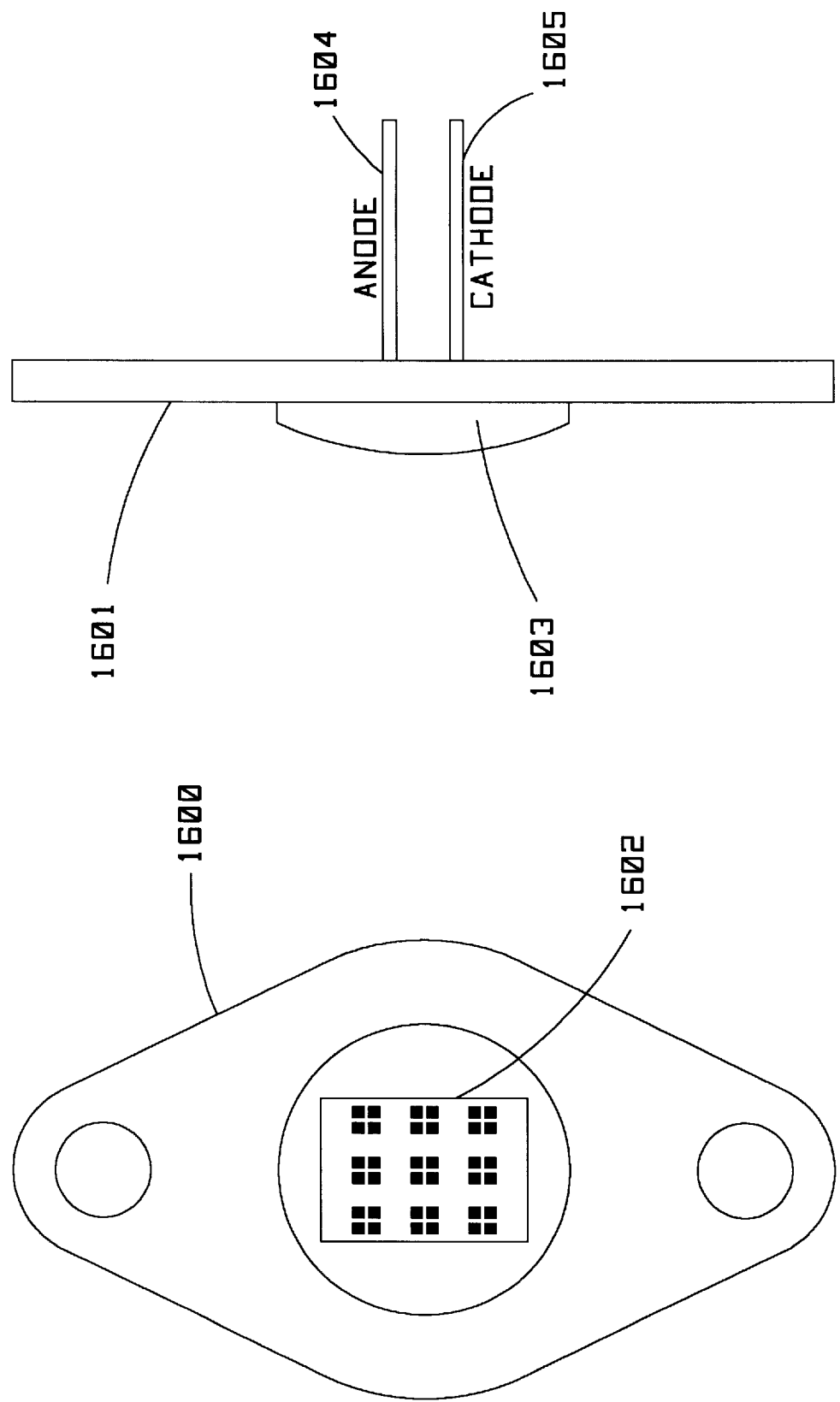
FIG. 16 illustrates an exemplary embodiment of the IR LED illumination source used in an exemplary embodiment of the present invention.

FIG. 16 illustrates a preferred embodiment of a LED radiation source (RTP using Opto Technology, Inc. model OTL680A-9-4-66-E). The device is typically mounted in a TO-3 package (1600) or the like. In a presently preferred embodiment, 36 high efficiency gallium aluminum arsenide infrared emitting diodes (1602) are contained within a TO-3 case (1601). An IR light window (1603) permits the IR radiation to be emitted external to the package (1601). Typical configurations of such a multi-emitter array may use rows and columns of LEDs, and in this embodiment four diodes spaced in three columns by three rows for a total of 36 LEDs is used. All the diodes are connected in series with the positive excitation voltage applied to the anode (1604) and the negative excitation voltage applied to the cathode (1605). Multiple numbers of devices as illustrated in FIG. 16 may be used to illuminate arbitrarily large areas, and the total number of devices used is application dependent. Additionally, the use of near-infrared radiation sources which emit some visible light may be suitable for many embodiments of the present invention.

Exemplary Schematic of LED Energizer

Figure 17:
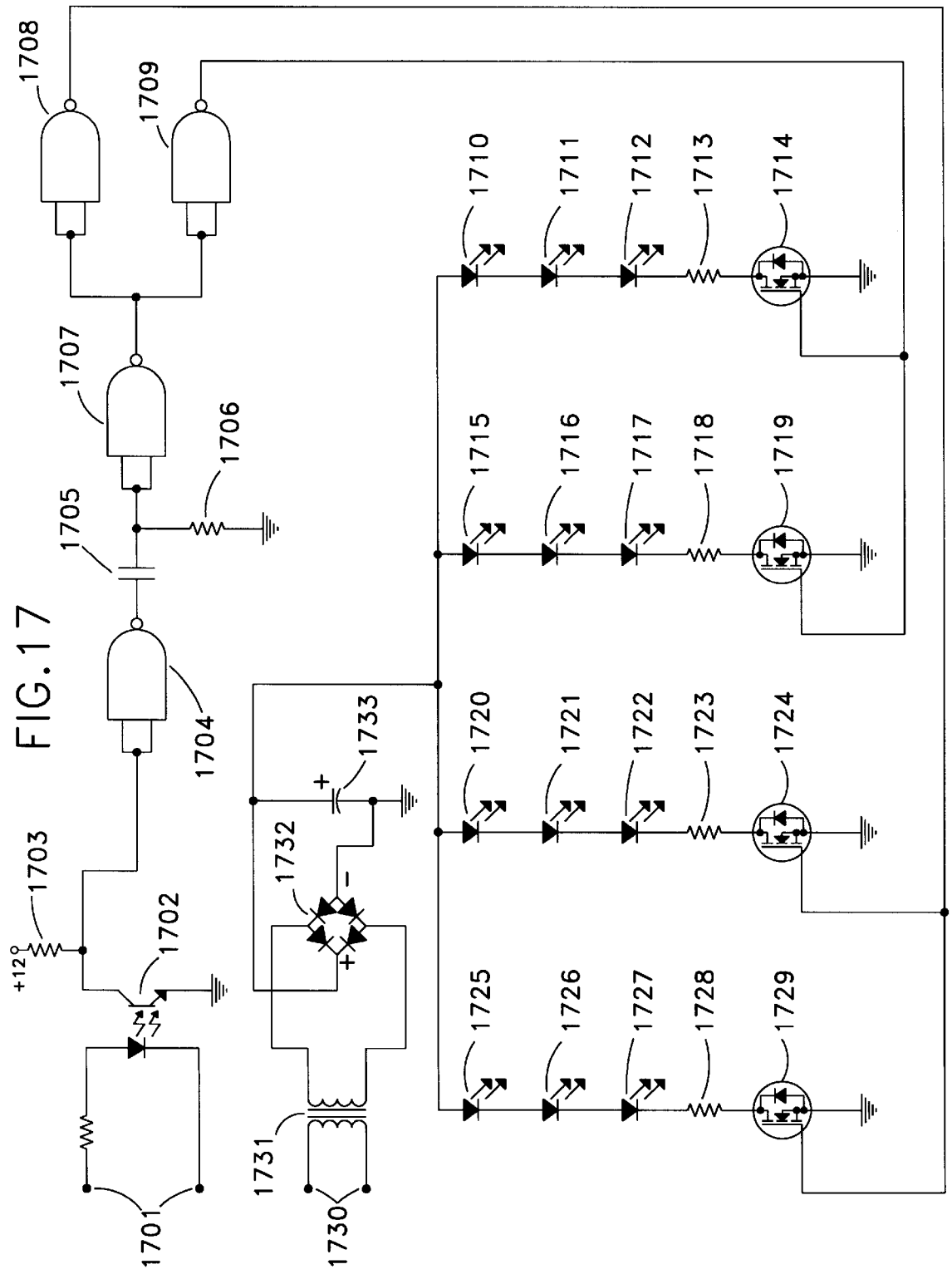
FIG. 17 illustrates a schematic of an exemplary embodiment of the IR LED illumination circuitry used in an exemplary embodiment of the present invention.

FIG. 17 illustrates a schematic of one exemplary implementation of energizing the LED assemblies according to the method block diagram described in FIG. 15. The activate pulse trigger (1701) energizes the optical coupler (1702) which through resister (1703) provides a negative going pulse at the input of gate (1704) (RTP using National Semiconductor CD4093BM). The output of gate (1704) provides the excitation for differentiator (1705/1706) to generate a pulse width duration of the time constant of capacitor (1705) and resister (1706) (RTP using a time constant of 10 microseconds). This short pulse energizes gate (1707) input which in turn provides a momentary negative-going pulse to gates (1708) and (1709), which then generate a momentary positive-going pulse at the output of gates (1708) and (1709).

The output of gate (1709) energizes N-channel MOSFET device (1714) and (1715) for the duration of the pulse coming from the output of (1707). Each MOSFET (1714, 1718, 1724, 1729) (RTP using International Rectifier IRFU220) will switch a maximum of ten amps for the duration of the LED excitation pulse, thus permitting full IR illumination to be generated by the LED device assemblies (1710, 1711, 1712, etc.).

The LED device assemblies (1710, 1711, 1712, etc.) are typically constructed of the form illustrated in FIG. 16 and exemplary of a typical illumination configuration as further illustrated in the system embodiment of FIG. 13 (1306). Note that the present embodiment utilizes four sets of LED device assemblies. It is significant to note that the number of LED assemblies required will be highly application dependent. The configuration illustrated in FIG. 13 and embodied in FIG. 17 is exemplary of only one possible embodiment of the invention that has been reduced to practice and should not be limitive of the teachings of the present invention.

Power for this exemplary embodiment is provided by an AC power source (1730) which excites a transformer (1731)

(RTP using Stancor model P-6411). The secondary winding of this transformer is rectified by bridge rectifier (1732) and filtered by capacitor (1733). With a nominal 120 volt AC input, the filtered voltage will be approximately 120 $\sqrt{2}=170V$.

Exemplary Software

Overview

While the teachings of the present invention may be implemented using a wide variety of methods, several of the preferred embodiments of the present invention have associated with them significant software subsystems. The following sections will detail the operation of these software embodiments and provide one skilled in the art sufficient detail to implement the teachings of the present invention in a wide variety of embodiments.

Operator Interface

While the teachings of the present invention may be embodied in a wide variety of forms, many of the preferred embodiments make use of operator interface display screens to aid in the setup and operation of various aspects of some invention embodiments. To aid the reader in understanding how these interfaces may be constructed, an exemplary command structure overview is provided in FIG. 54, with exemplary screen interface displays presented in FIGS. 55–59. Note that these screen interfaces will vary widely with the type of computer system platform on which the invention is embodied, and are provided as a guide to the reader rather than as any limitation on the scope and range of the teachings of the present invention.

Figure 54:
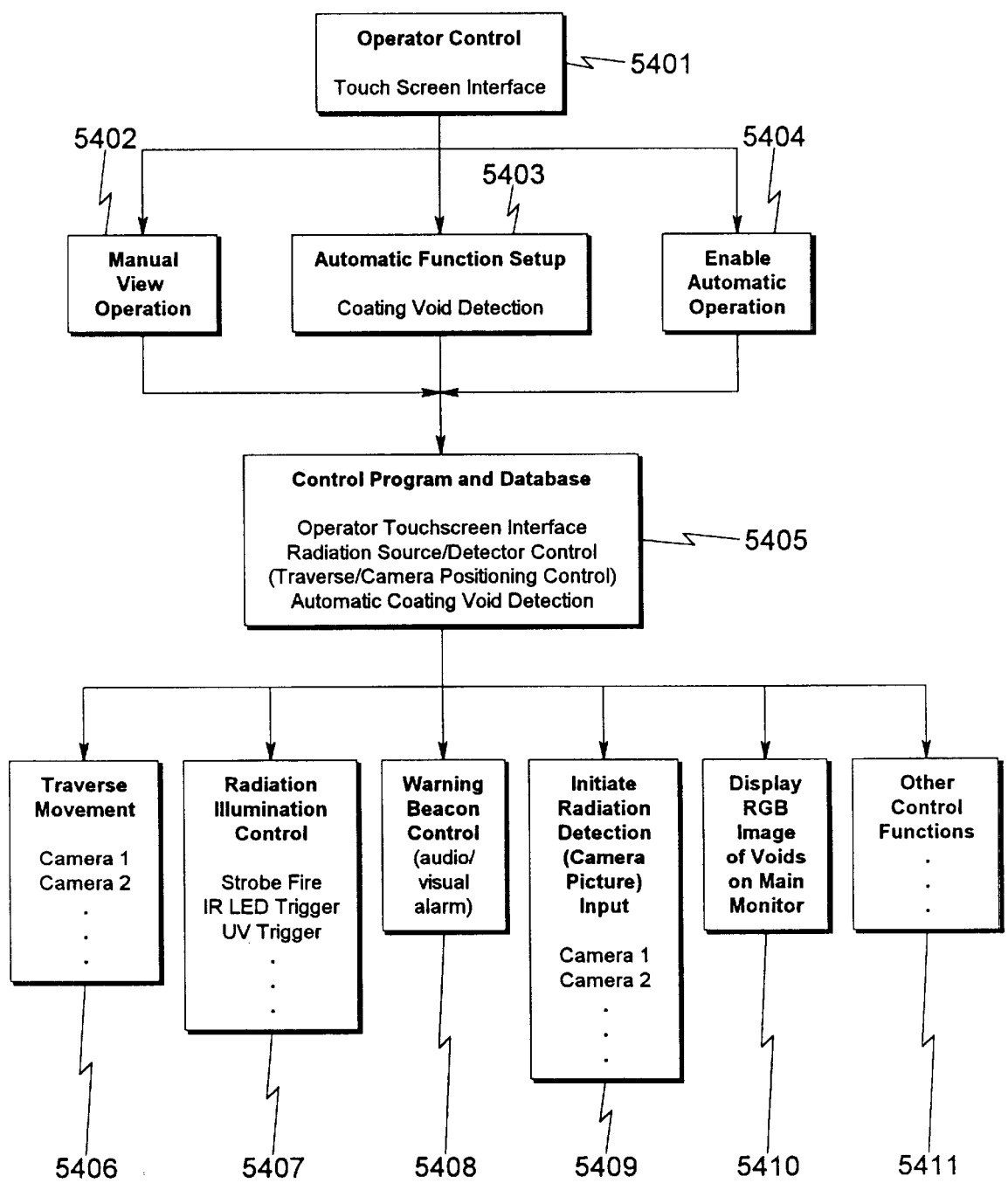
FIG. 54 illustrates an overview flowchart of an exemplary operator function control interface used to combine manual and automatic void detection systems within an integrated void detection and coating control printing system.
Figure 55:
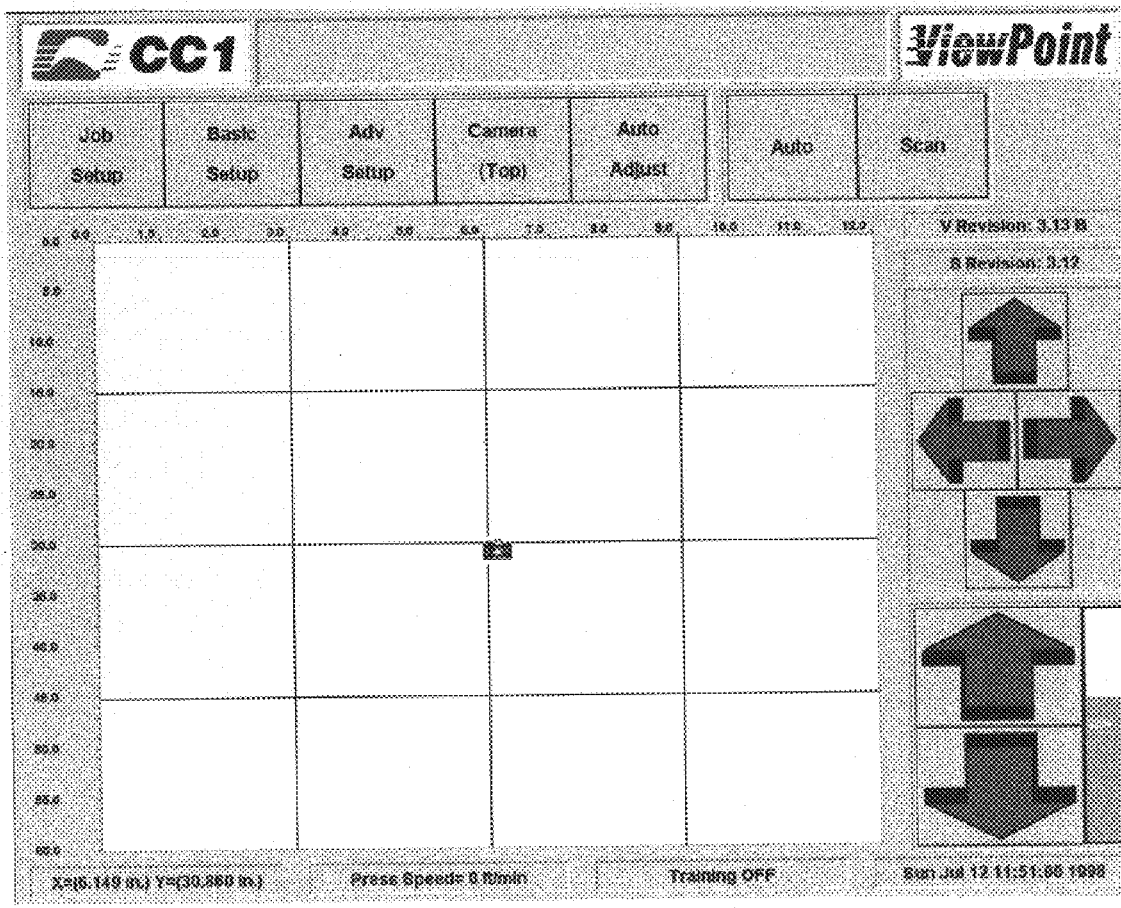
FIG. 55 illustrates an exemplary operator screen interface used in conjunction with the exemplary control system illustrated in FIG. 54.
Figure 56:
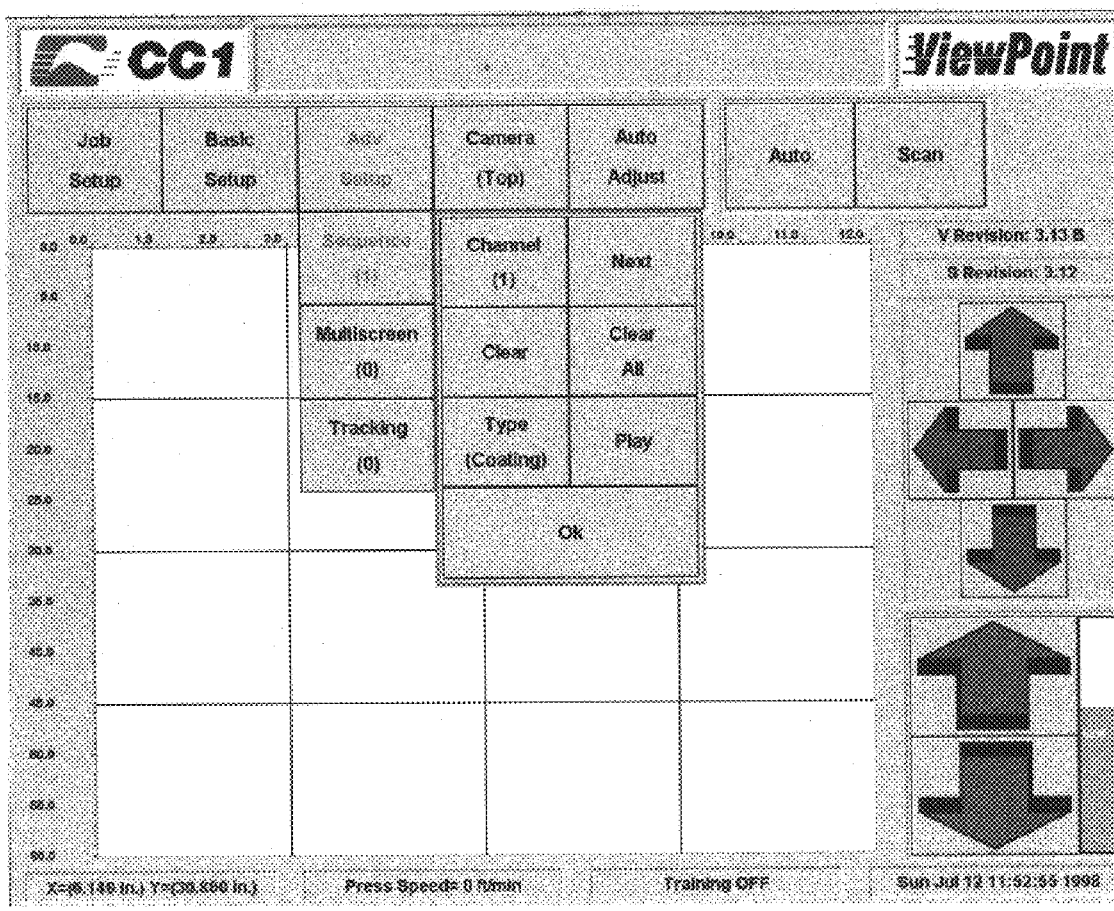
FIG. 56 illustrates an exemplary operator screen interface used in conjunction with the exemplary control system illustrated in FIG. 54.
Figure 57:
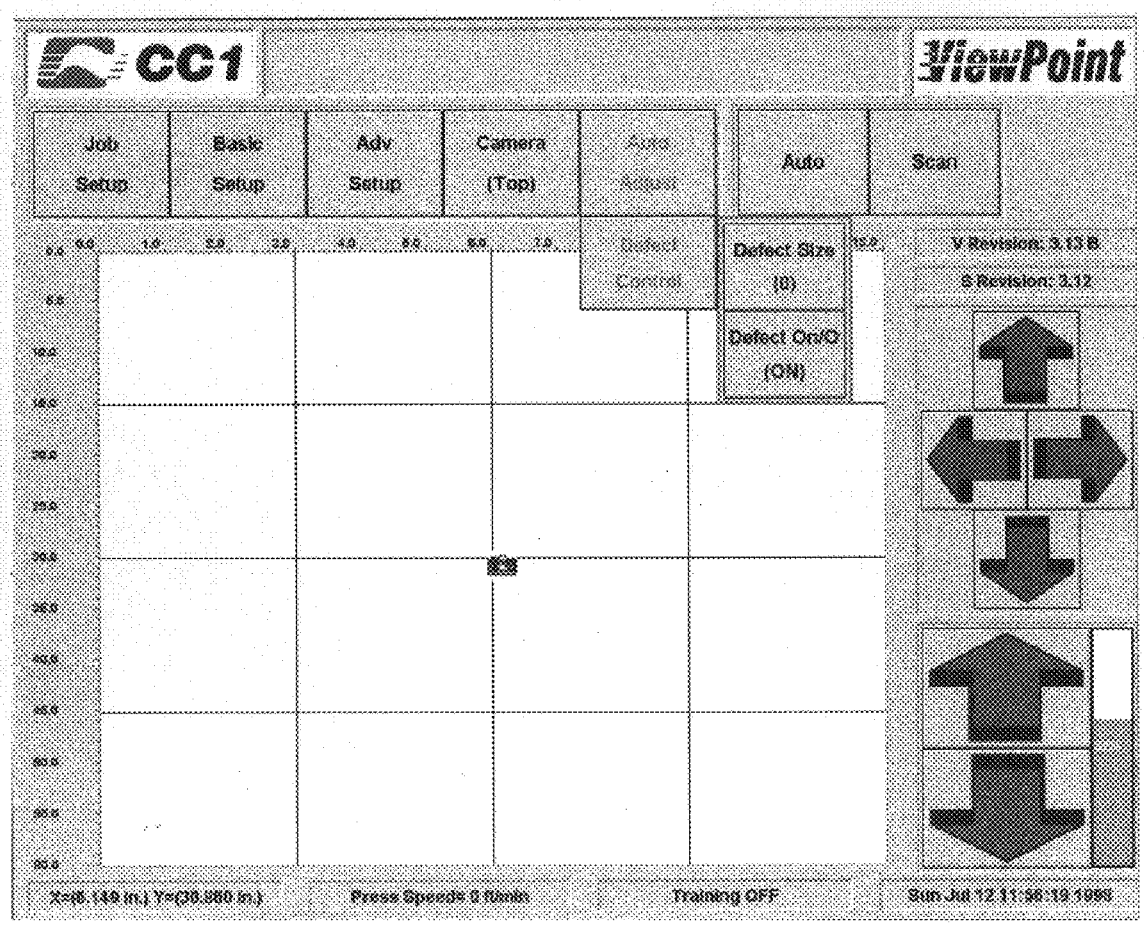
FIG. 57 illustrates an exemplary operator screen interface used in conjunction with the exemplary control system illustrated in FIG. 54.
Figure 58:
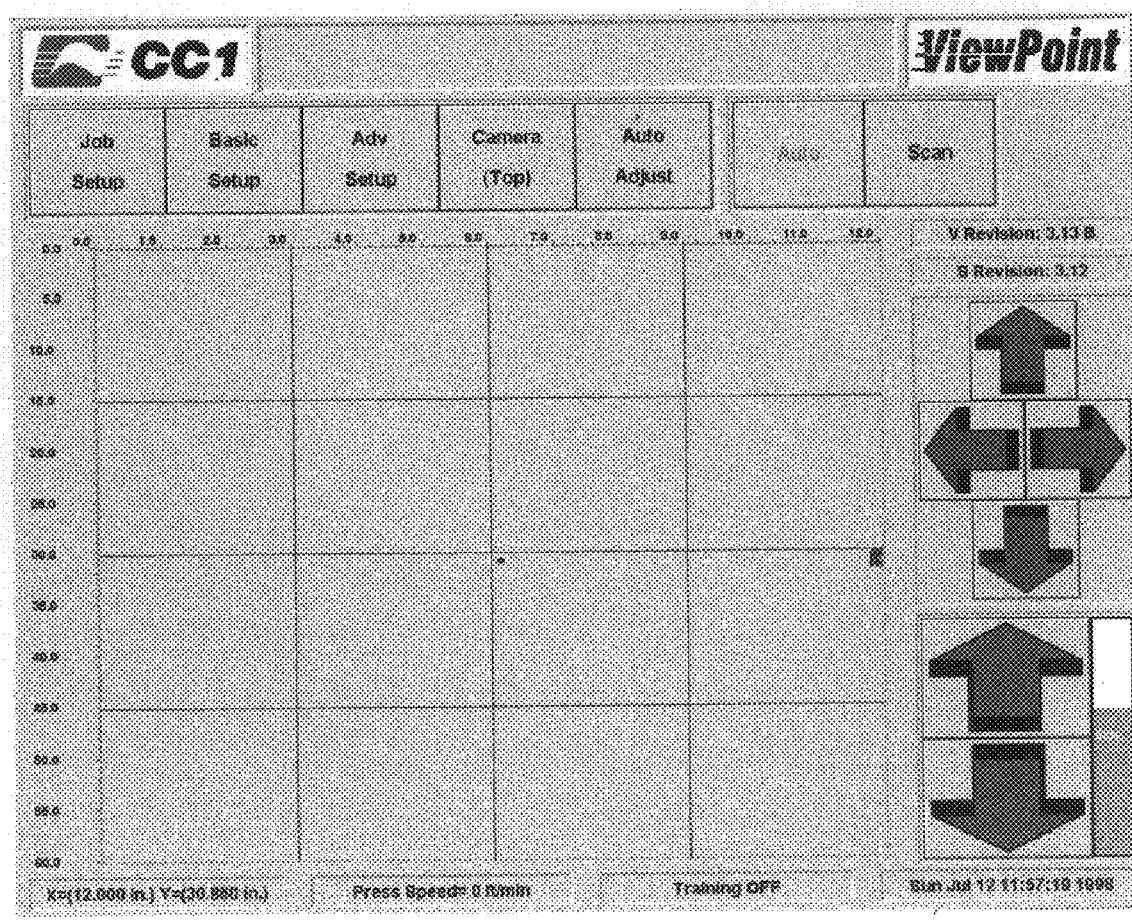
FIG. 58 illustrates an exemplary operator screen interface used in conjunction with the exemplary control system illustrated in FIG. 54.
Figure 59:
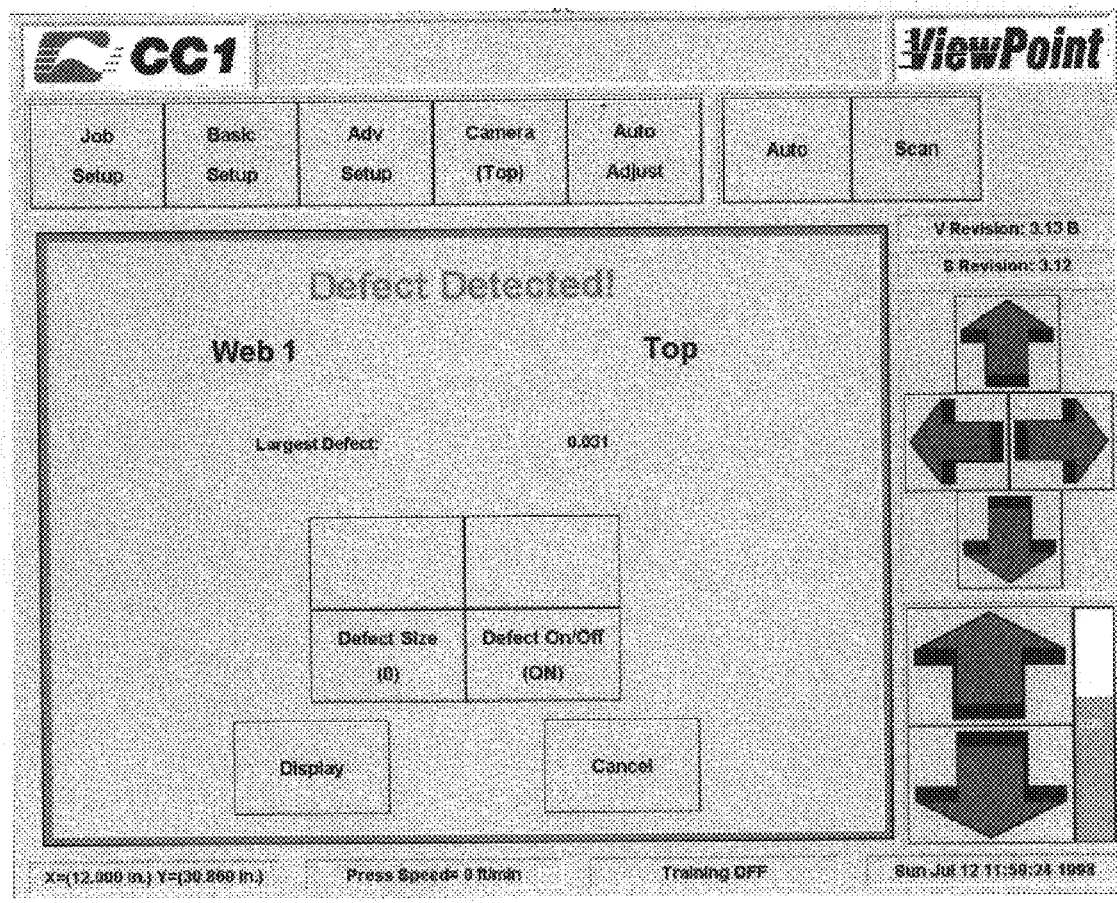
FIG. 59 illustrates an exemplary operator screen interface used in conjunction with the exemplary control system illustrated in FIG. 54.

Referencing the exemplary operator interface of FIG. 54, one preferred method of interfacing to the operator is via the use of a touch screen display (5401). From this input device, the system may be operated in a manual inspection mode (5402), or coating voids may be automatically detected after the operator performs a setup configuration operation (5403) and subsequently enables automatic void detection operation (5404). These steps configure a void detection control program database (5405) which acts as data input to the various hardware task controls in the system (5406, 5407, 5408, 5409, 5410, 5411).

The hardware task controls of the exemplary system may control a plethora of tasks within the context of void detection. Some exemplary embodiments of these may include traverse movement of the radiation detector (5406), radiation illumination control (5407), activation of a warning beacon (5408), initiation of backscatter radiation detection (5409), display of image voids in RGB format on a display monitor (5410), or other system control functions (5411). As will be known by one skilled in the art, this command structure is amenable to expansion to support other hardware control functions and thus the present invention specifically anticipates that other process monitoring and control functions will be integrated into this process flow in many embodiments of the present invention.

Coating Detection Setup

Figure 18:
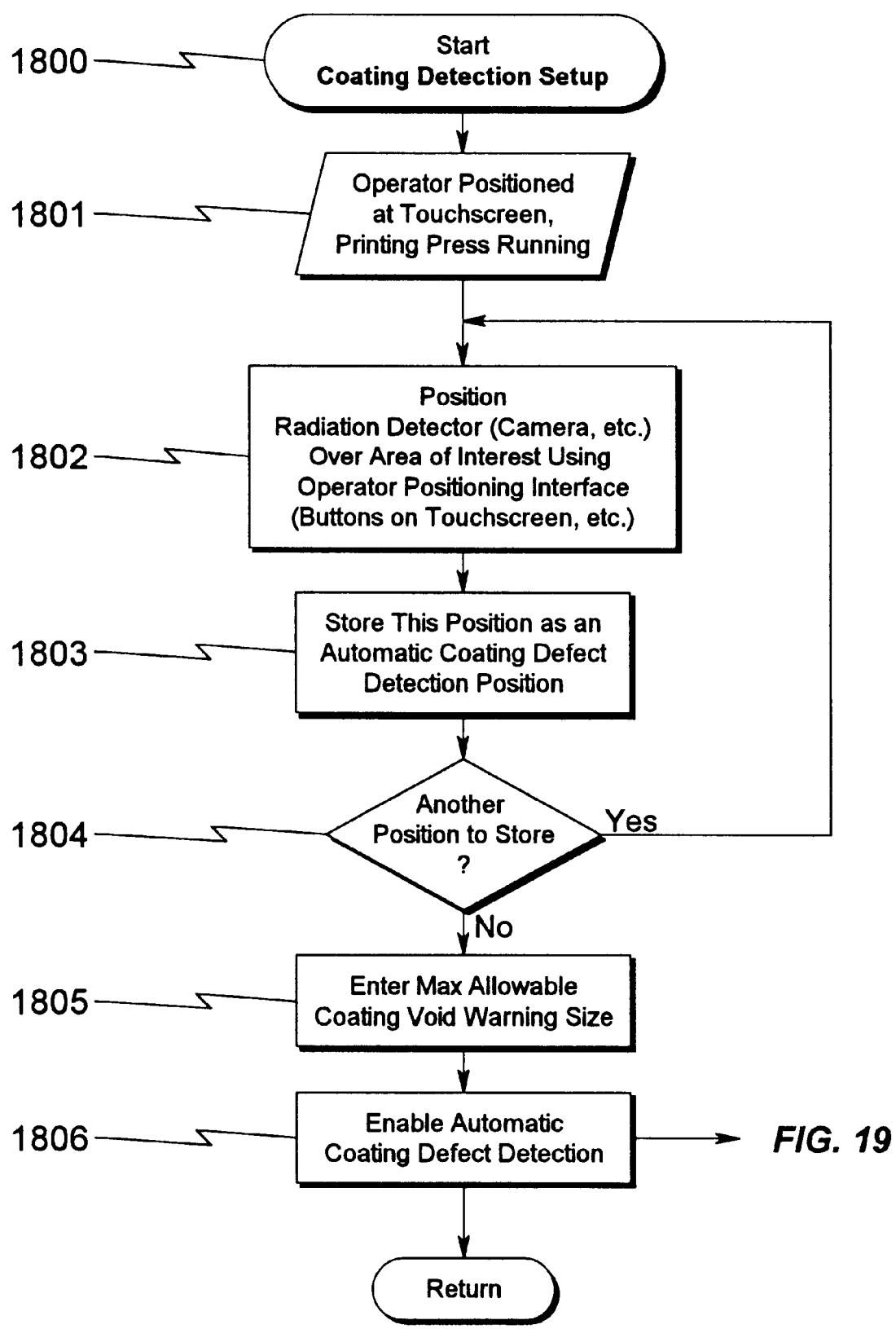
FIG. 18 illustrates an overview flowchart of an exemplary embodiment of the coating detection setup method taught by the present invention.

Setup of a typical coating deposition and void detection application as taught by embodiments of the present invention is detailed in the exemplary process flowchart of FIG. 18 starting with an initial entrypoint (1800). To setup the machine, the printing press must be running and the operator must be positioned before the display monitor and touchscreen (1801). First the operator will position the camera over the web to a position of interest where the coating can be automatically viewed for proper laydown (1802). The operator can use positioning arrow buttons on the touchscreen for camera positioning and camera zoom. Alternately, the digitizer interface can be used. The digitizer is an area on the touchscreen which represents a repeat of the web. By moving his finger across the digitizer, the operator can position the camera to an area of interest. The digitizer and camera positioning arrows are illustrated in the touch screen illustration FIG. 55. When the camera is properly positioned, the operator stores this position as a coating defect analysis position (1803). An exemplary embodiment of this interface is shown in the screen illustration of FIG. 56. If the operator wishes to store another position for analysis (1804), he can position the camera as already described and store another position (1802). When all analysis positions have been entered, the operator next enters the Maximum Allowable Coating Void Warning Size (1805) using the entry screen illustrated in FIG. 57. Lastly, the operator enables automatic void detection by touching the automatic enable button (1806) illustrated in FIG. 58.

Automatic Coating Detection Operation

Figure 19:
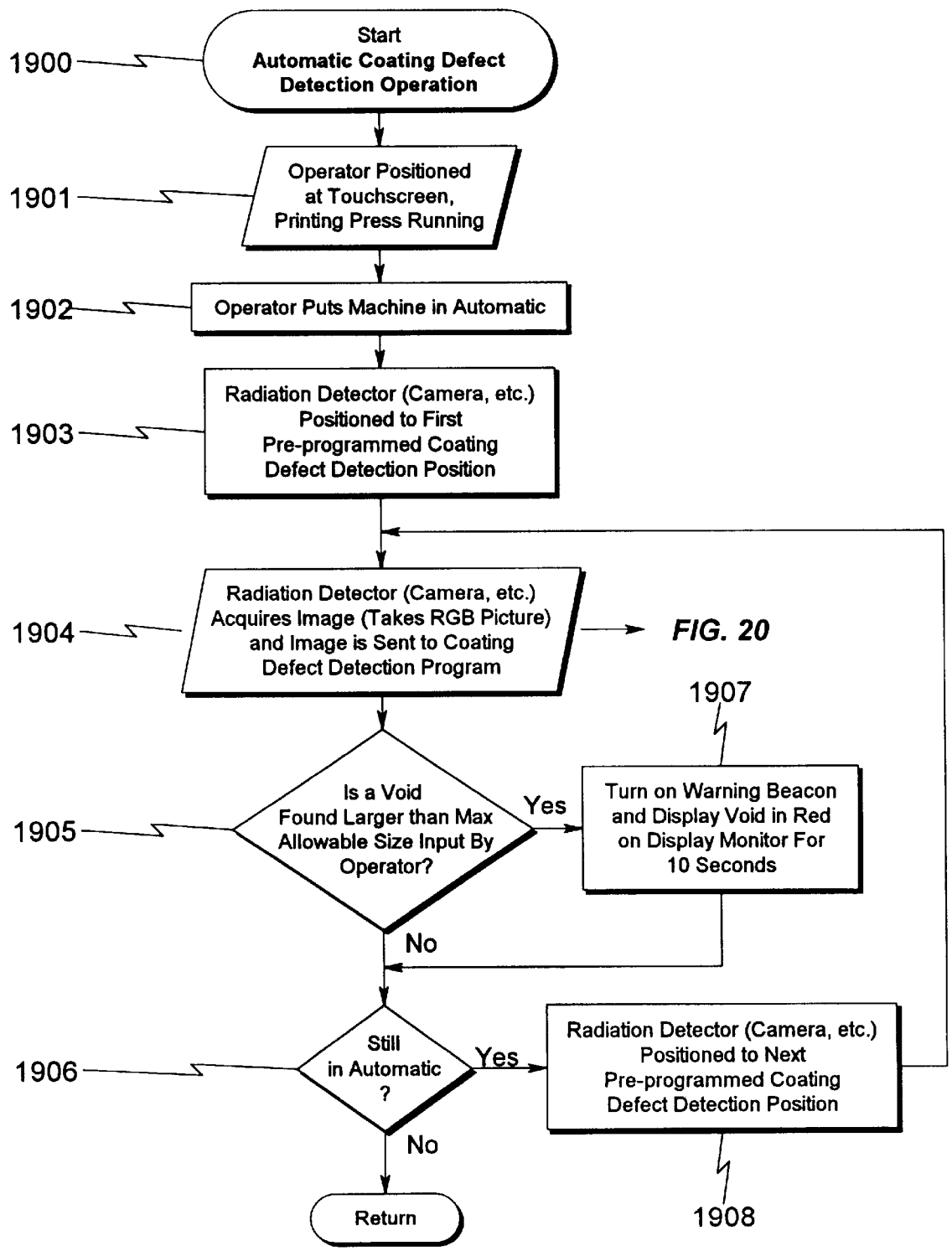
FIG. 19 illustrates an overview flowchart of an exemplary embodiment of the automatic coating defect detection method taught by the present invention.

Operation of Automatic Coating Detection is performed as described in the exemplary process flowchart of FIG. 19. Start of the procedure is shown in entrypoint (1900). The operator is positioned before the display monitor at the touchscreen with the printing press running (1901). The Operator puts the machine in automatic by touching the AUTO button (1902), illustrated on the exemplary embodiment of the touchscreen illustration in FIG. 58. At this point the control program takes over and positions the camera at the first inspection point (1903). The control program takes a picture at this position (1904) and passes this RGB image and control to the coating defect detection algorithm described later. If the Coating Defect Detection algorithm finds a void larger than the operator entered maximum allowable size (1905) then the warning beacon is turned on and the void(s) is/are displayed on the monitor for 10 seconds (1907) along with an error display as illustrated by the exemplary screen image in FIG. 59. If no defect was found or at the conclusion of the warning display, the coating defect algorithm releases control to the control program which checks to see if the machine is still in automatic (1906). If the machine is still in automatic, the next inspection point is found and the camera is positioned to it (1908), the camera takes a picture as before (1904) and operation continues in automatic as described above. If the machine is no longer in automatic, the control program enters a wait state waiting for operator input.

Coating Defect Detection Process

The purpose of the coating defect application software is two-fold:
1. To find or segment areas of coating from non-coating on the input image, and
2. To find voids or "holes" within homogeneous areas of the coating.

The segmentation step is dependent on the type of coating to be analyzed. This method of coating defect detection can be applied to any coating applied to a homogeneous substrate by illuminating (with suitable radiation) the coating and/or substrate additives to permit visual differentiation so that successful segmentation can be performed. Two exemplary segmentation methods will be detailed here:
1. Tinted Coating. This method has a color additive which give the coating a slight tint, different from the flat, colorless background.
2. Fluorescing Coating. This method uses a clear (invisible) coating with an additive that causes it to emit visible light when illuminated with radiation from the non-visible portion of the spectrum.

Here it must be noted that these two categories are simply variations on the more general teaching of the present invention that a coating medium may be irradiated with some radiation source and the backscattered radiation detected with some suitable sensor detector array. The result of this sensor detection may be analyzed to determine the presence of voids in the material coating. Whether the radiation source is visible is completely arbitrary, and dependent on the coating application. Similarly, the use of fluorescing coatings is simply a modification of the type of backscattered radiation to which the sensor array is to be tuned to detect.

Once the areas of coating/non-coating are determined, the coating area can be analyzed for defects. In general, satisfactory coating laydown is homogeneous and covers large areas. Therefore, there should be no small "holes" or voids in the coating area. If small holes are found, it can be assumed that the coating laydown is deteriorating and that adjustments in the printing/manufacturing process are warranted.

Void Detection Process

Figure 20:
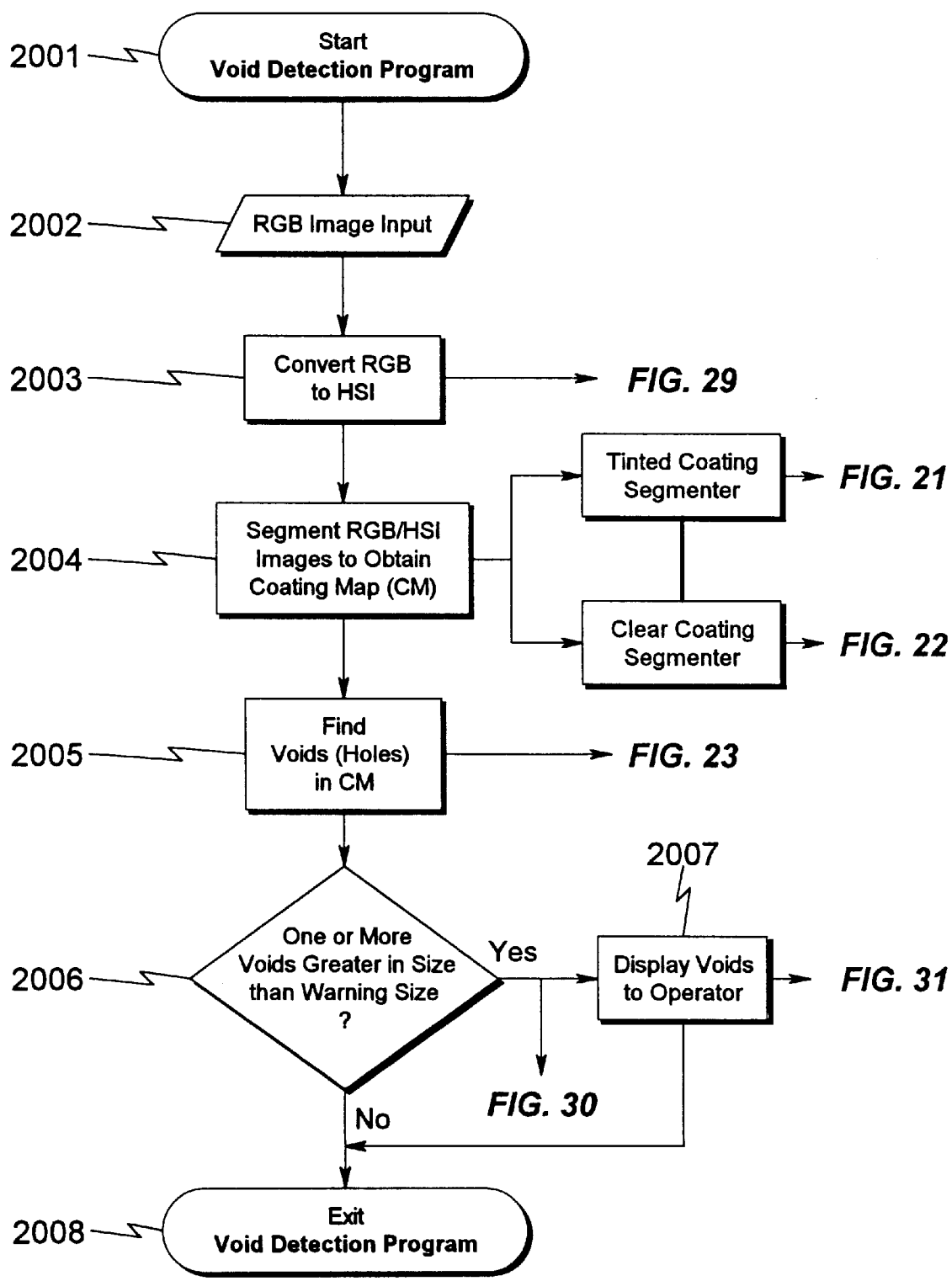
FIG. 20 illustrates an overview flowchart of an exemplary embodiment of the void detection method taught by the present invention.
Figure 29:
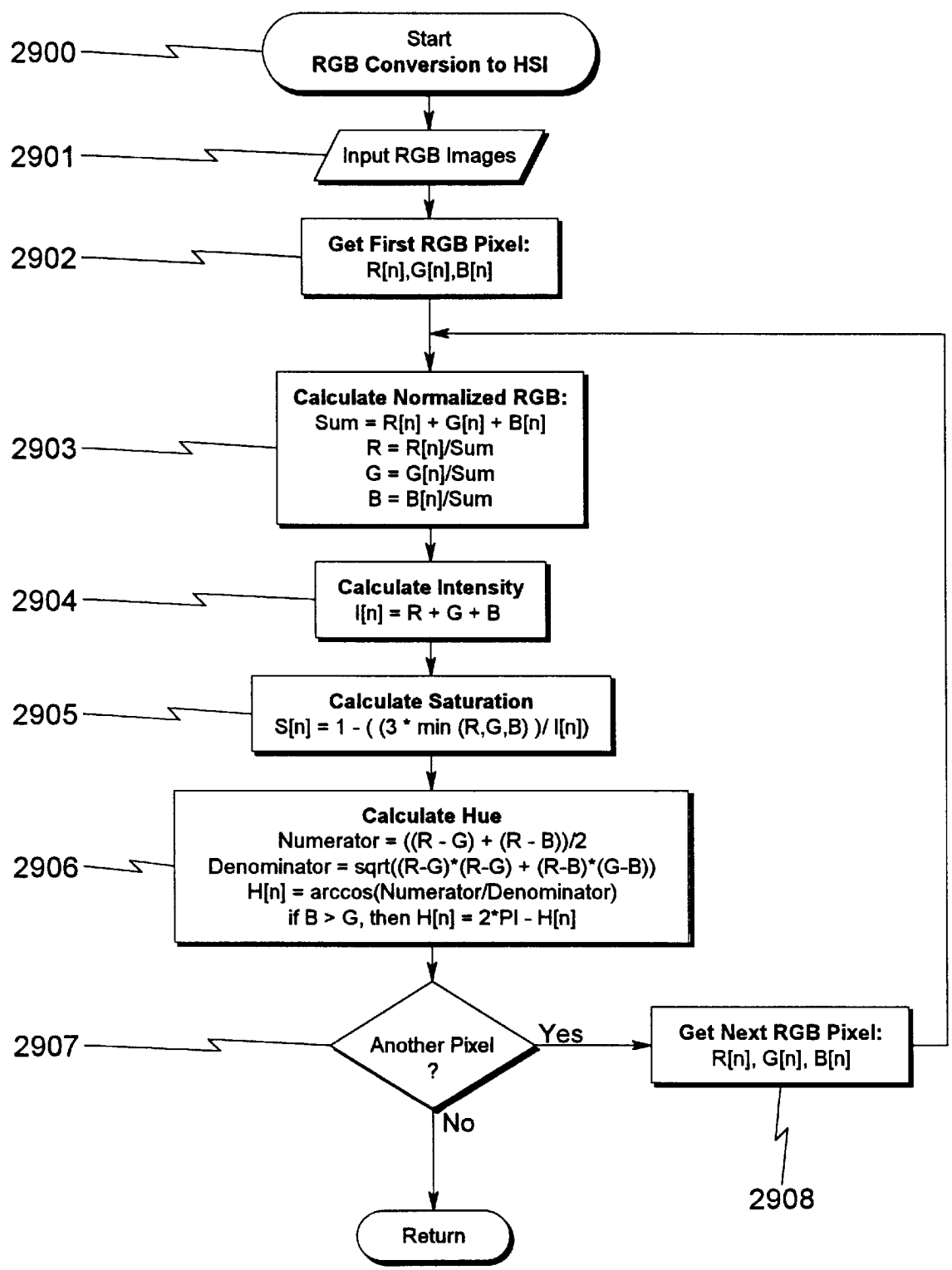
FIG. 29 illustrates an overview flowchart of an exemplary embodiment of an RGB-to-HSI conversion method taught by the present invention.

FIG. 20 is a flowchart of the overall process of void detection of a coating process. The defect detection process begins when the control program passes a Red-Green-Blue (RGB) image to the detection program (2001). Each color plane (Red, Green, and Blue) is a gray level image digitized to 8 bits (2002). The input Red-Green-Blue (RGB) images from the coating application are first used to calculate corresponding Hue-Saturation-Intensity (HSI) images (2003). These calculations are performed on a pixel by pixel basis. The formulas for HSI calculations are detailed in the exemplary process flowchart of FIG. 29 in steps (2900, 2901, 2902, 2903, 2904, 2905, 2906, 2907, and 2908). These six separate images are used as input to the segmentation process (2004).

The segmentation process is application specific and may be embodied by a wide variety of systems and methods. Two exemplary embodiments of the methods taught by the present invention will be considered here:
1. tinted coating segmentation (detailed by the exemplary flowchart illustrated in FIG. 21), and
2. clear coating segmentation using IR illumination (detailed by the exemplary flowchart illustrated in FIG. 22).

The result of the segmentation operation is the Coating Map (CM). The CM is a monochrome image where every pixel set to 0 corresponds to a non-coating (or substrate) location on the image and every pixel set to 1 corresponds to coating locations.

Referencing FIG. 20, the next step is to analyze the CM for voids (2005). This process is detailed in the exemplary process flowchart of FIG. 23. Voids (or holes) within homogeneous areas of coating will correspond to small groups of black pixels (pixels set to 0) within large groups of white pixels (pixels set to 1) or coating areas in the CM.

The purpose of this application is to measure the size of each of these voids in terms of black pixel area (2006). The void measurement process is detailed in the exemplary process flowchart of FIG. 30. If the largest measured void is larger than an operator entered maximum allowable void size, a warning is sent to the calling program which causes a visual beacon to be lighted as well as display warnings on viewing and control monitors (2007). The error display function is detailed in the exemplary process flowchart of FIG. 31. If the largest measured void is less than an operator entered maximum allowable void size, the void detection program exits with no action (2008).

Segmentation

Two specific forms of segmentation will be discussed in the context of the present invention embodiments:

Tinted Coating Segmentation (FIG. 21); and
Clear Coating (FIG. 22) Segmentation.

Note however, that the present invention teachings are applicable to a wide variety of coating applications and should not necessarily be limited to the two exemplary embodiments discussed.

Image Pixel Notation

Note that in this and other discussions of the image pixel plane processing, a linear indexing structure may at times be used to describe the orientation of a given pixel P[n] to the eight neighbor pixels which surround it:

| $P[n-4]$ | $P[n-3]$ | $P[n-2]$ | (1) |
|---|---|---|---|
| $P[n-1]$ | $P[n]$ | $P[n+1]$ | |
| $P[n+2]$ | $P[n+3]$ | $P[n+4]$ | |

Figure 27:
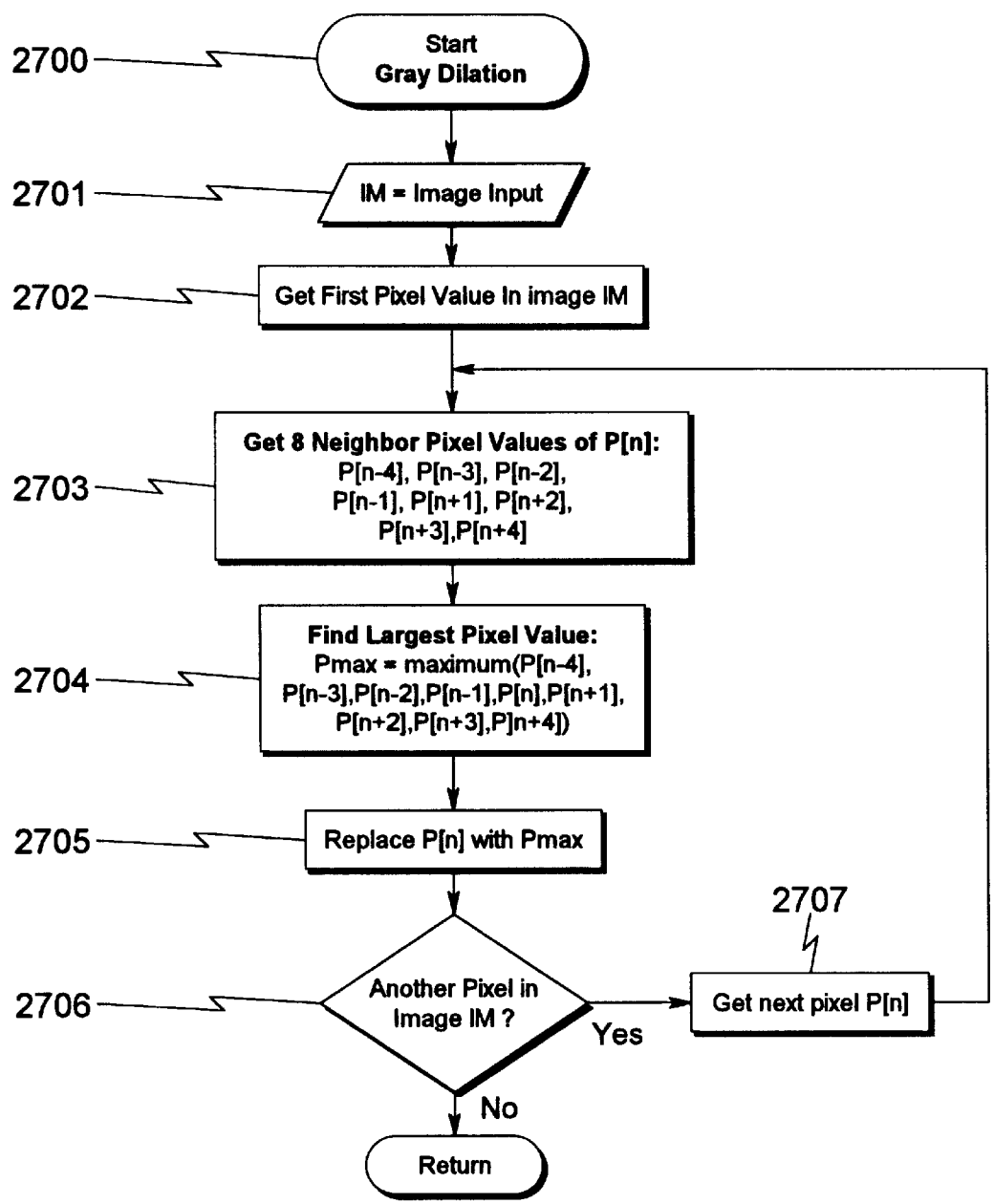
FIG. 27 illustrates an overview flowchart of an exemplary embodiment of a method taught by the present invention to perform gray dilation.
Figure 28:
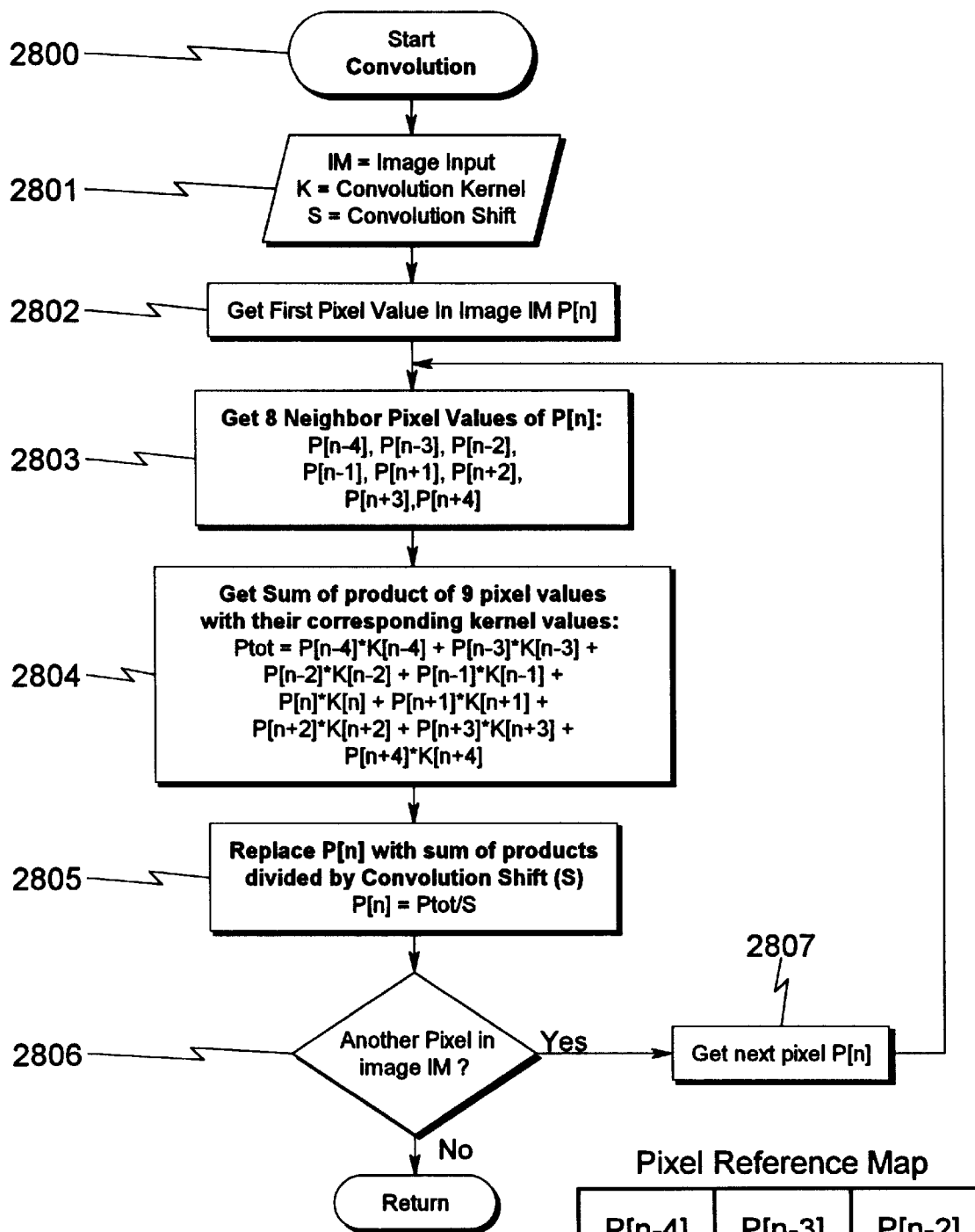
FIG. 28 illustrates an overview flowchart of an exemplary embodiment of a method taught by the present invention to perform image convolution/filtering.
Figure 32:
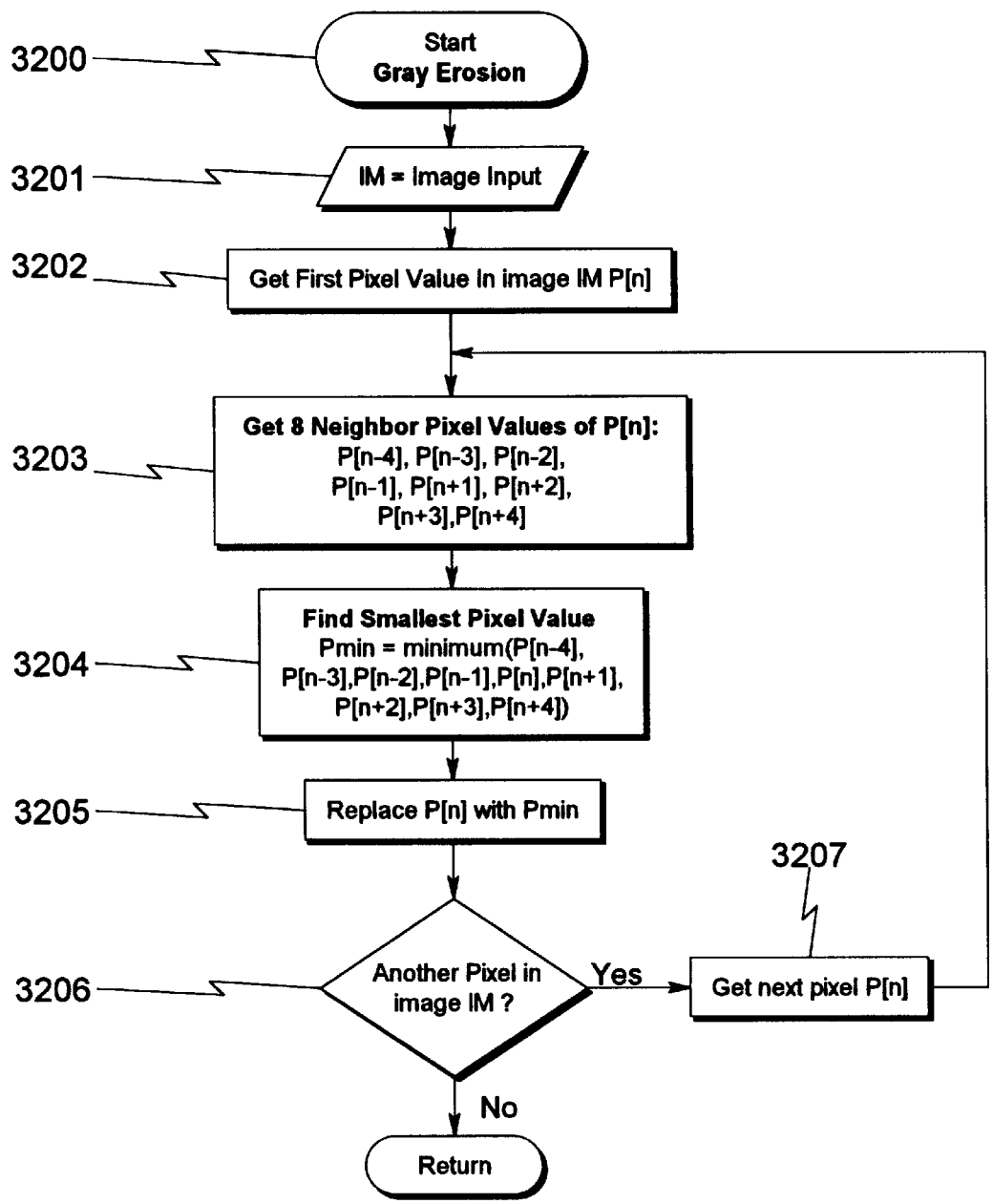
FIG. 32 illustrates an overview flowchart of an exemplary embodiment of a method taught by the present invention to perform gray erosion.

This notation is indicated where appropriate in the exemplary process flowcharts of FIG. 27, FIG. 28, and FIG. 32

Tinted Coating Segmentation

Figure 21:
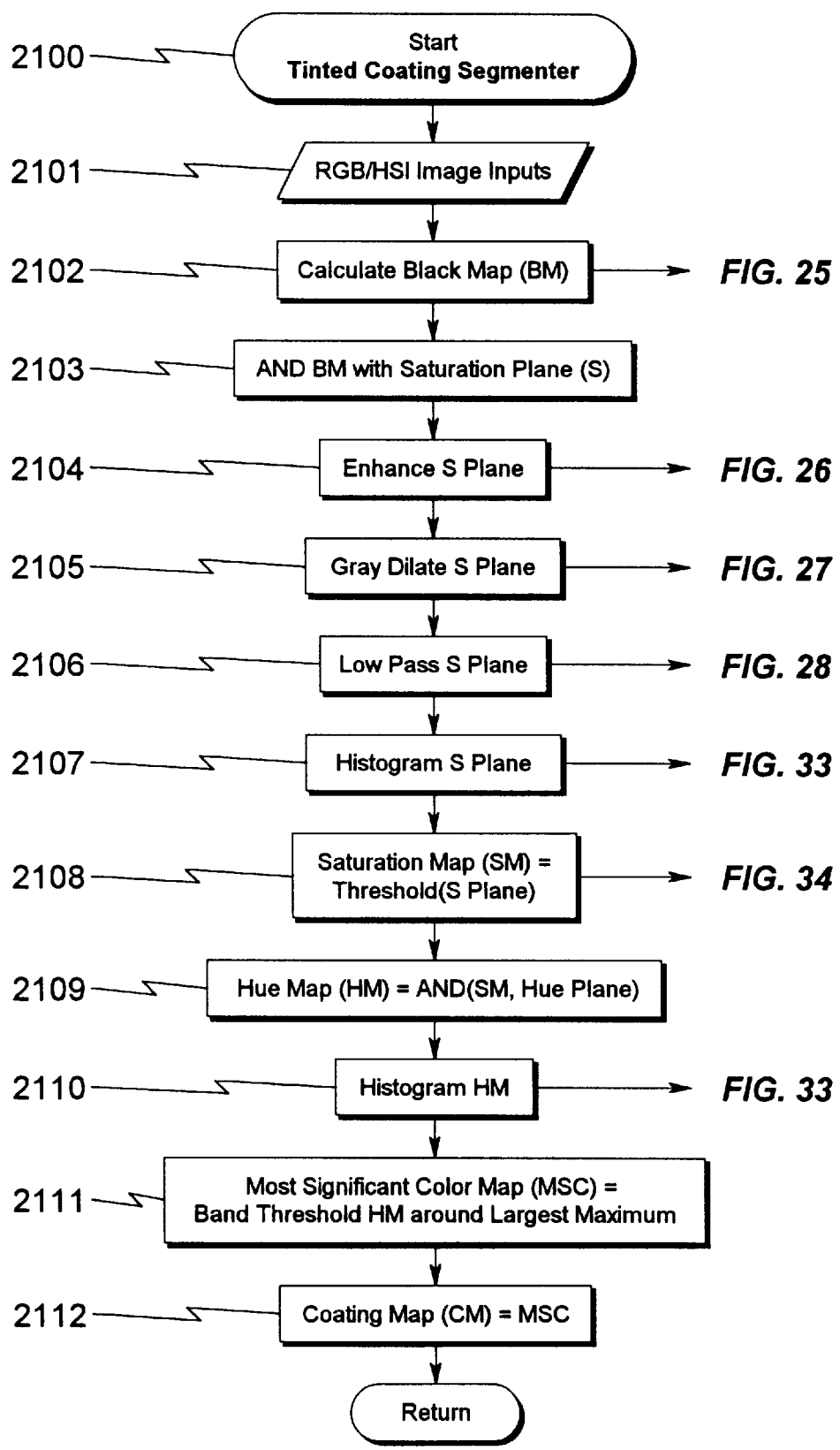
FIG. 21 illustrates an overview flowchart of an exemplary embodiment of the tinted coating segmenter method taught by the present invention.
Figure 36:
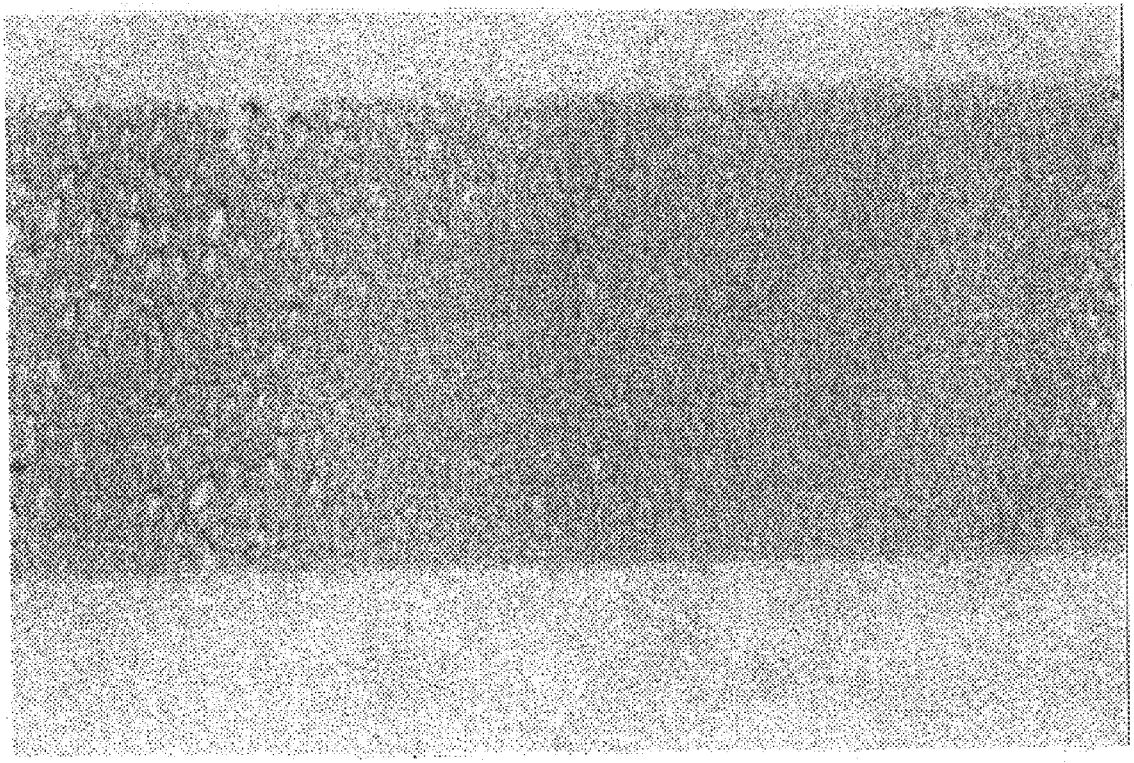
FIG. 36 illustrates in a tinted coating application an exemplary input RGB image used in tinted and clear coating void detection.

The basic idea behind segmenting a tinted coating from a flat substrate is color saturation. The saturation of a color is a measure of how "rich" or strong it looks. Pure white, black, and all the gray values between have a color saturation of 0; they have no color. The darker and richer a color is, the higher is it's saturation value. An RGB image of tinted coating is illustrated in FIG. 36. The segmentation method described here uses the saturation plane to find the tinted coating in the input images. Referring to FIG. 21, tinted coating segmentation starts (2100) with the input RGB images and the input HSI images (2101) of the current image to be checked for voids. The first step in segmenting the tinted coating is to remove any black from the image (2102). Black would most likely come from the edge of the web.

Black Map Segmentation

Figure 25:
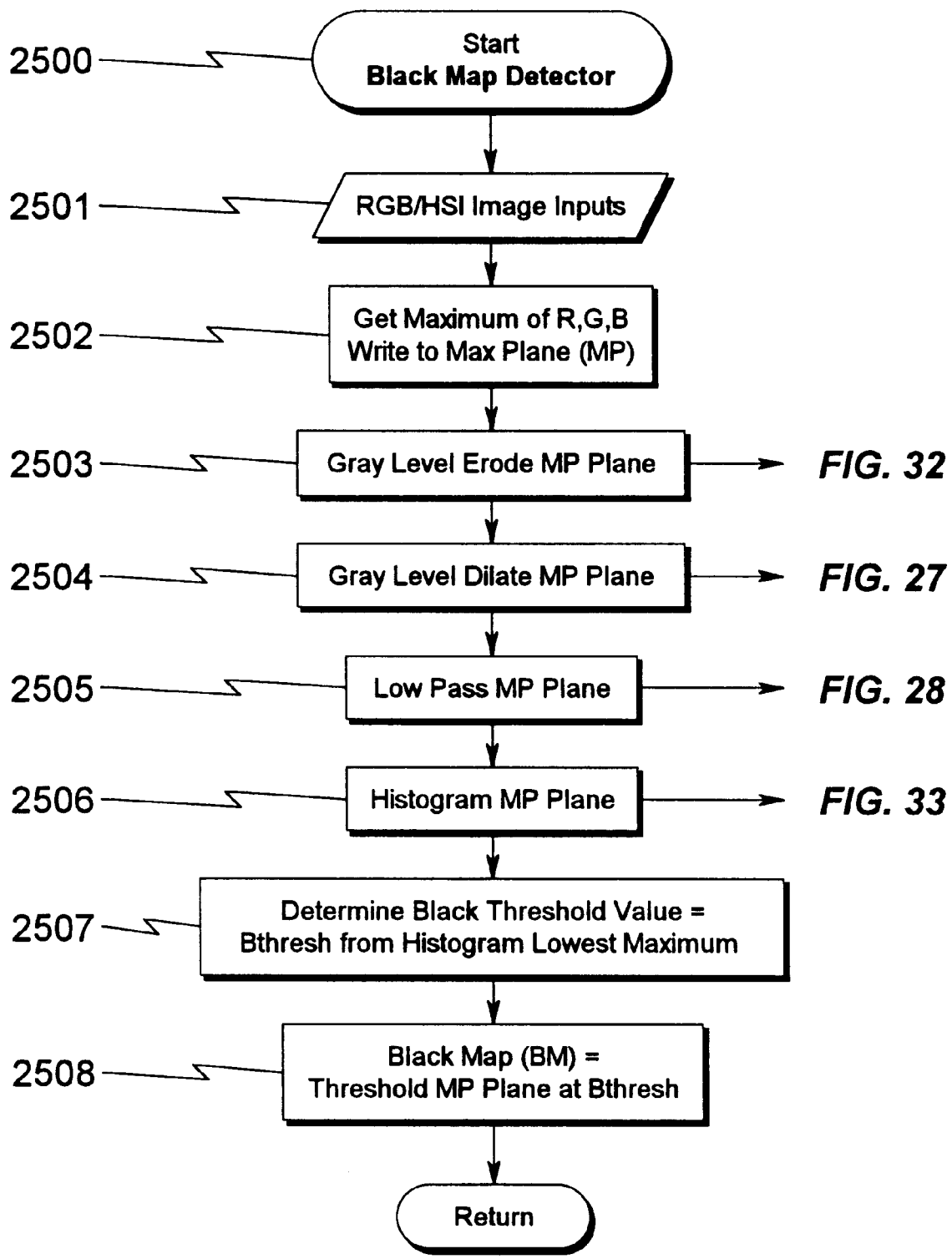
FIG. 25 illustrates an overview flowchart of an exemplary embodiment of a method taught by the present invention to map black thresholds.

Black Map Segmentation is detailed in the exemplary process flowchart of FIG. 25. Upon entry to the subroutine (2500), the RGB and HSI are passed to the routine (2501) for analysis. First, the maximum of the RGB planes is determined (2502). This is done by comparing the Red, Green, and Blue planes on a pixel by pixel basis. Thus for a particular pixel position in each of the RGB planes: Pr, Pg, Pb, the maximum valued pixel is found and written to a Max Plane (MP) as follows:

$$MP(x,y) = \max(P_R(x,y), P_G(x,y), P_B(x,y)) \qquad (2)$$

This is done for every corresponding pixel in the RGB planes.

The resulting MP plane is now gray level eroded (2503). This process is detailed in the exemplary process flowchart of FIG. 32. The process begins at (3200) when the subroutine is called. Any input image can be eroded. In this case, the MP plane is the input plane to be eroded and is set equal to the IM plane (3201). Every pixel in the IM plane is considered in gray erosion. The first pixel P[n] is first acquired (3202) and then the eight neighboring pixels are inspected to find the minimum pixel value as follows:

$$P[n] = \min(P[k]_{k=n-4}^{k=n+4}) \qquad (3)$$

as detailed in (3203). The minimum pixel value of these 9 pixel values is determined (3204), that is the smallest pixel value in this group of 9 is determined and then replaces pixel P[n]. If there is another pixel to be analyzed (3206), the next pixel in IM is then acquired (3207), set to P[n] and program control goes back to (3203) where the eight neighbor pixels are determined. This process continues until all pixels in IM (MP) have been analyzed.

Referencing the exemplary process flowchart of FIG. 25, the gray eroded MP plane is now gray dilated (2504). This process is detailed in the exemplary process flowchart of FIG. 27. The process begins at (2700) when the subroutine is called. Any input image can be dilated. In this case, the MP plane is the input plane to be dilated and is set equal to the IM plane (2701). Every pixel in the IM plane is considered in gray dilation. The first pixel P[n] is first acquired (2702) and then the eight neighboring pixels P[n−4], P[n−3], P[n−2], P[n−1], P[n+1], P[n+2], P[n+3], P[n+4] (2703). The maximum pixel value of these 9 pixel values is determined (2704), that is the largest pixel value in this group of 9 is determined and then replaces pixel P[n]. If there is another pixel to be analyzed (2706), the next pixel in IM is then acquired (2707), set to P[n] and program control goes back to (2703) where the 8 neighbor pixels are determined. This process continues until all pixels in IM (MP) have been analyzed.

Referencing the exemplary process flowchart of FIG. 25, the gray dilated MP plane is now low pass filtered (2505). This process is detailed in the exemplary process flowchart of FIG. 28. The process begins at (2800) when the subroutine is called. Image filtering in general is called convolution. Convolution requires an input image (IM) on which to perform the convolution, an input 3×3 convolution kernel (K) which specifies the type of filtering to perform on IM and the convolution shift value (S) which is the divisor for each sum of product operation in the convolution. S normalizes the resulting or convolved image. Referring to FIG. 28, the input image is the MP plane, which is set equal to IM for this operation (2801), K is set to a 3×3 convolution kernel of all 1's which is a low pass filtering operation, and S is set to 9 which results in a convolved image with the same intensity range as the input image. To begin the low-pass filtering operation the first pixel, P[n], is retrieved from the input image IM (2802). Next, the eight neighbors of P[n]: P[n−4], P[n−3], P[n−2], P[n−1], P[n+1], P[n+2], P[n+3], and P[n+4] are retrieved (2803). Next, the sum of products of these pixel values with their corresponding kernel values (2804) is calculated a follows:

$$P_{TOT} = \sum_{i=-4}^{i=+4} P[i]K[i] \quad (4)$$

Since this is a low pass filtering operation, Ptot is the sum of the nine image pixels P[n−4] . . . P[n+4] since the kernel values are all 1. Next, the original input pixel P[n] is replaced with the normalized sum of products (2805). Ptot is divided by the convolution shift value, K=9 in this case and P[n] is replaced with the result. Next, the input image is checked to see if there is another pixel that can be processed (2806). If there is another pixel, it is read and set to P[n] (2807). Next, P[n]'s eight neighbors are read as before (2803) and the next normalized sum of products is calculated. The subroutine is exited when all pixels in the image have been processed.

Figure 33:
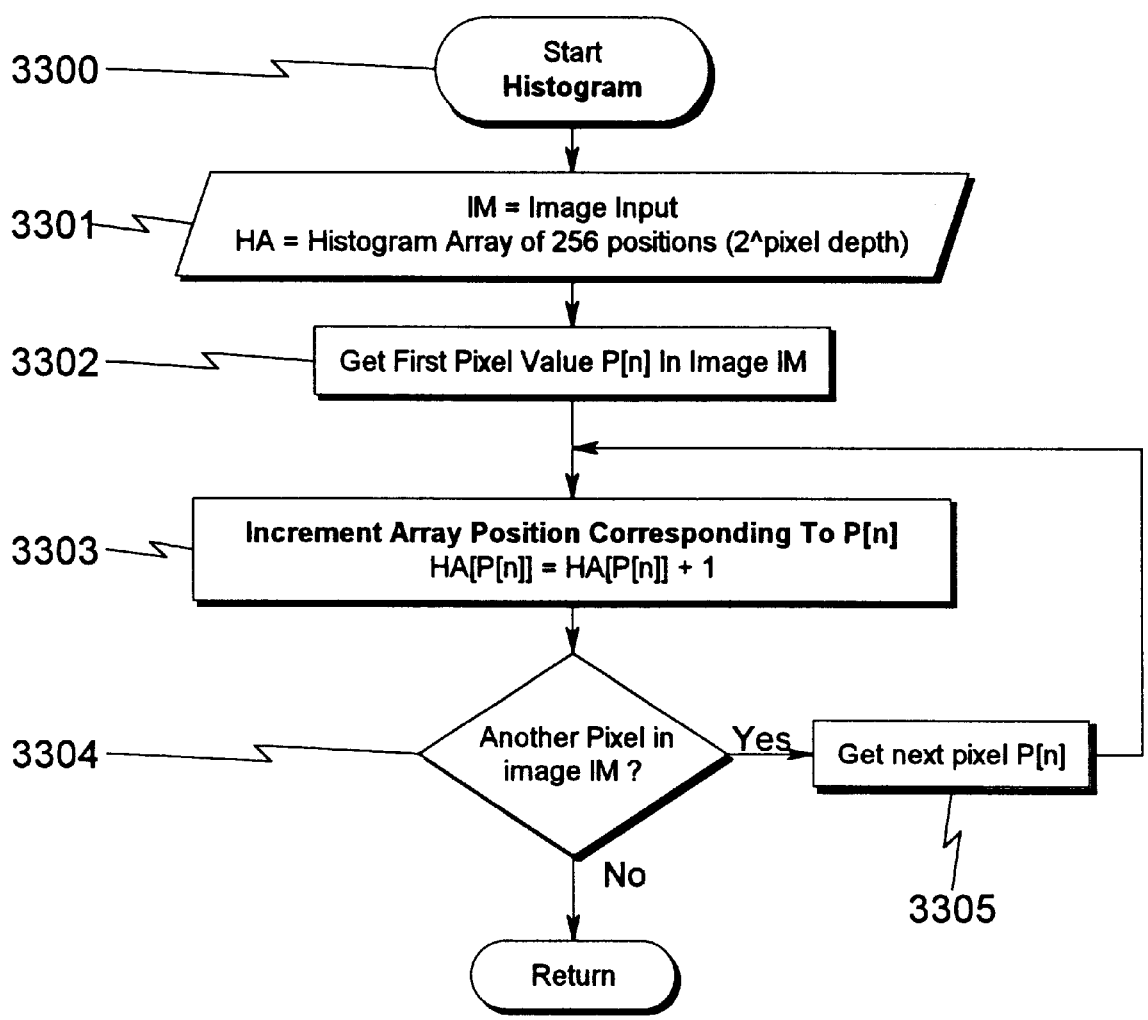
FIG. 33 illustrates an overview flowchart of an exemplary embodiment of a method taught by the present invention to generate image histograms.

Referencing the exemplary process flowchart of FIG. 25, with a low pass filtered MP plane, the MP plane is now histogrammed (2506). This process is detailed in the exemplary process flowchart of FIG. 33. The process begins at (3300) when the subroutine is called. Histogramming is a method of determining the pixel intensity value distribution in an image. First the input image MP is set to the subroutine input image IM and an array of 256 integer values, 1 value for each possible intensity value in an image is created (3301). Next the first pixel (P[n]) in the input image (IM) is obtained (3302). The value of P[n] serves as the address into the Histogram Array (HA). The integer value stored at this address is incremented by 1 (3303). Next the image is checked to see if there is another pixel that can be processed (3304). If there is, the next pixel value P[n] is obtained (3305) and this new pixel value serves as the address into the HA as before (3303). If there are no more pixels to process in IM, the routine is exited with the HA returned.

Referencing the exemplary process flowchart of FIG. 25, with a histogram of the MP plane, the next step is to determine the threshold value for black in the image and threshold the MP plane using this value (2507). This is accomplished as follows: the HA array is analyzed to find the first maximum or "bump". If this maximum is below the intensity mid-point of 128 (assuming an 8-bit pixel value), it is assumed to be black in the image. The half power point of this maximum is then determined by finding the right-hand valley corresponding to this maximum, this is the black threshold value (Bthresh). Then the MP plane is thresholded such that all pixel values in MP that are less than Bthresh are set to 0 and all pixel values greater than or equal to Bthresh are set to 1 (2508). The result of this operation is the Black Map (BM) which has a pixel value of 0 wherever there is black in the input image and 1 wherever there is coating or substrate which should be analyzed for voids.

Tinted Coating Segmentation

Figure 37:
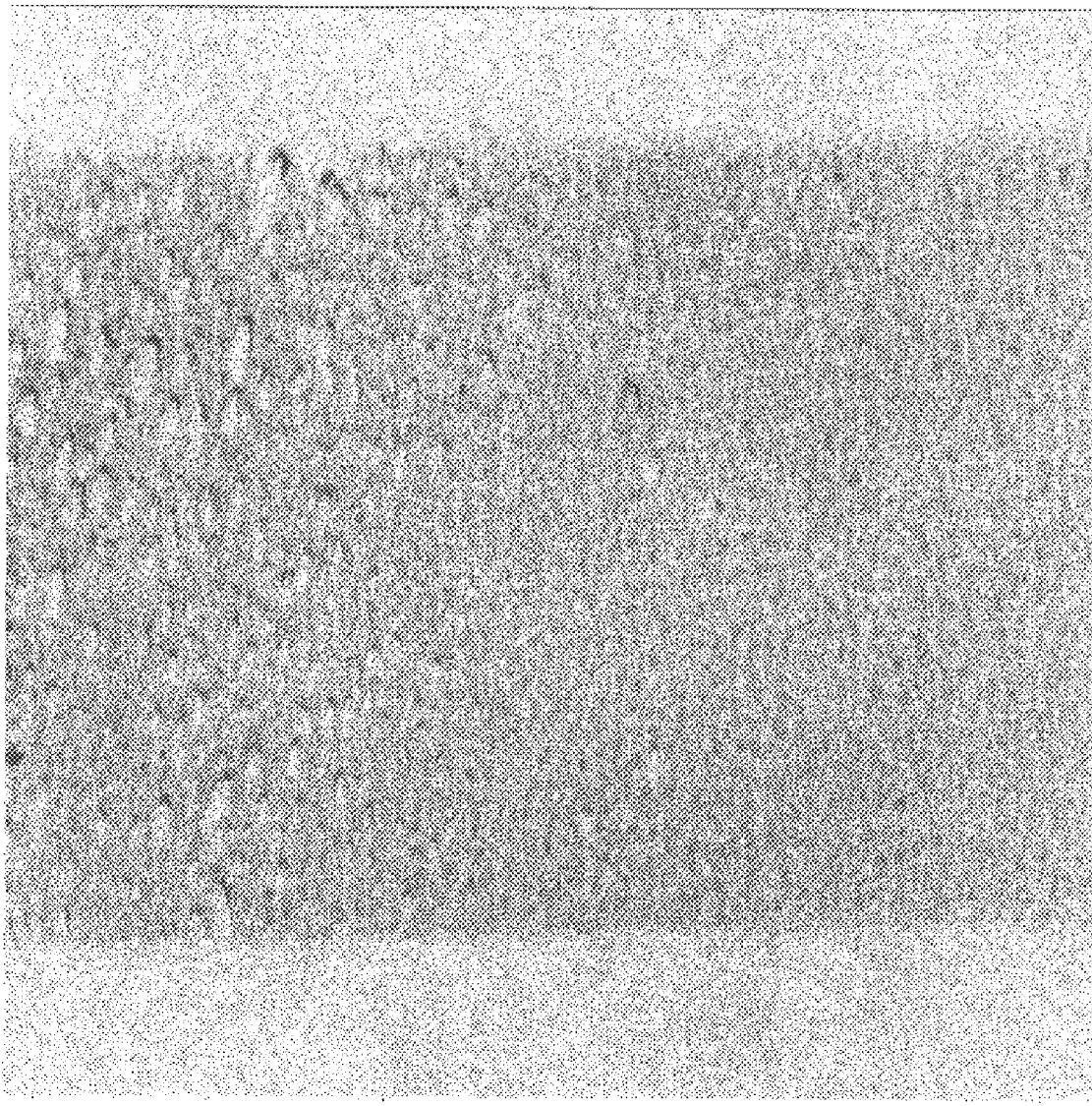
FIG. 37 illustrates in a tinted coating application an exemplary monochrome image obtained from the exemplary input RGB image of FIG. 36.

Referencing the exemplary process flowchart of FIG. 21, the result of the black map segmentation is a mask image which has a pixel value of 0 where black is and a pixel value of 1 everywhere else. This black map (BM in FIG. 21) is logically ANDed with the saturation (S) image (2103). The result of the AND operation is to set pixels in the S plane to 0 or leave them alone if the corresponding value of the BM is 0 or 1 respectively. This leaves the S image only with coating and substrate information. An exemplary monochrome image of the tinted coating is illustrated in FIG. 37.

Figure 26:
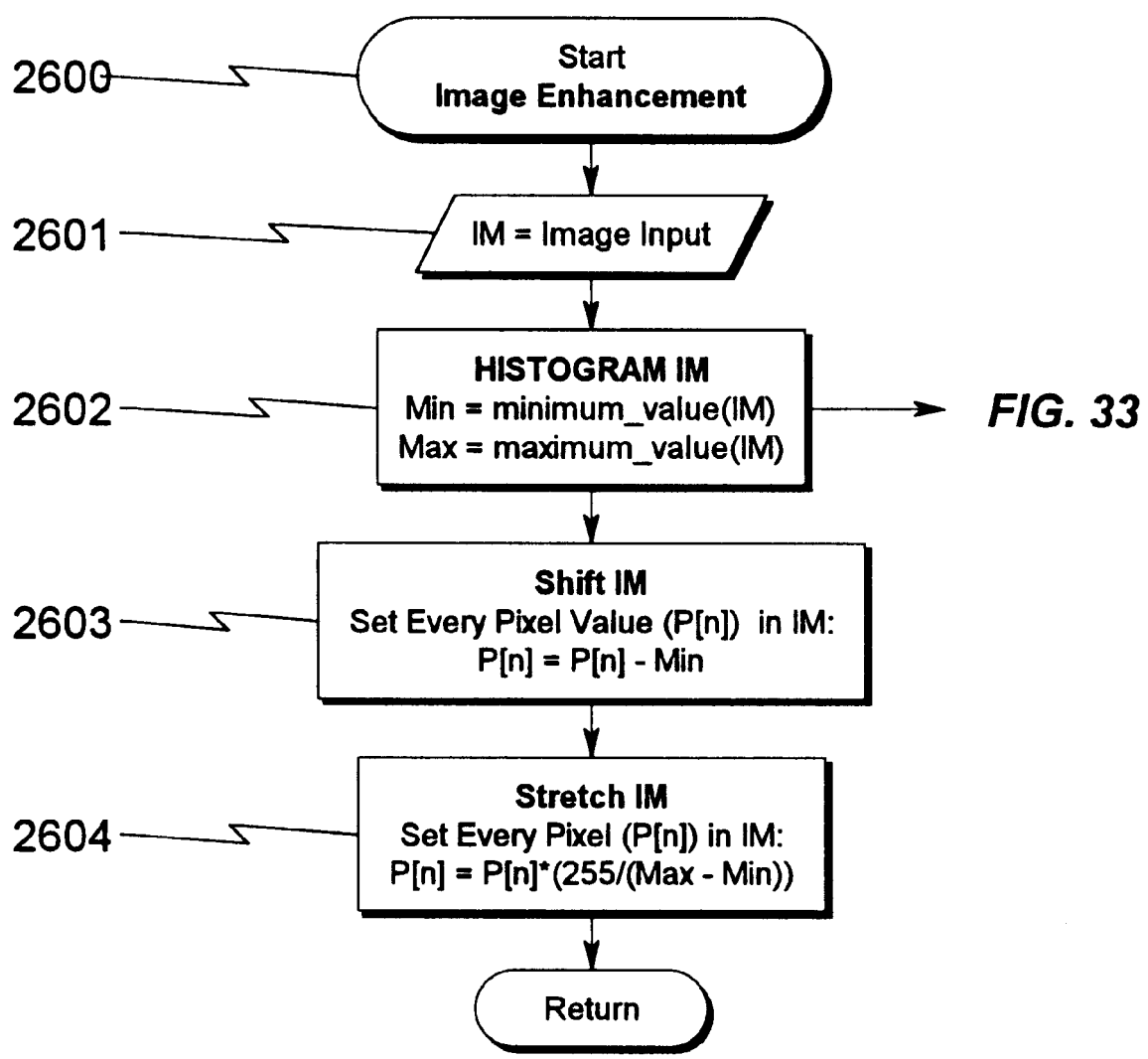
FIG. 26 illustrates an overview flowchart of an exemplary embodiment of a method taught by the present invention to perform image enhancement.
Figure 38:
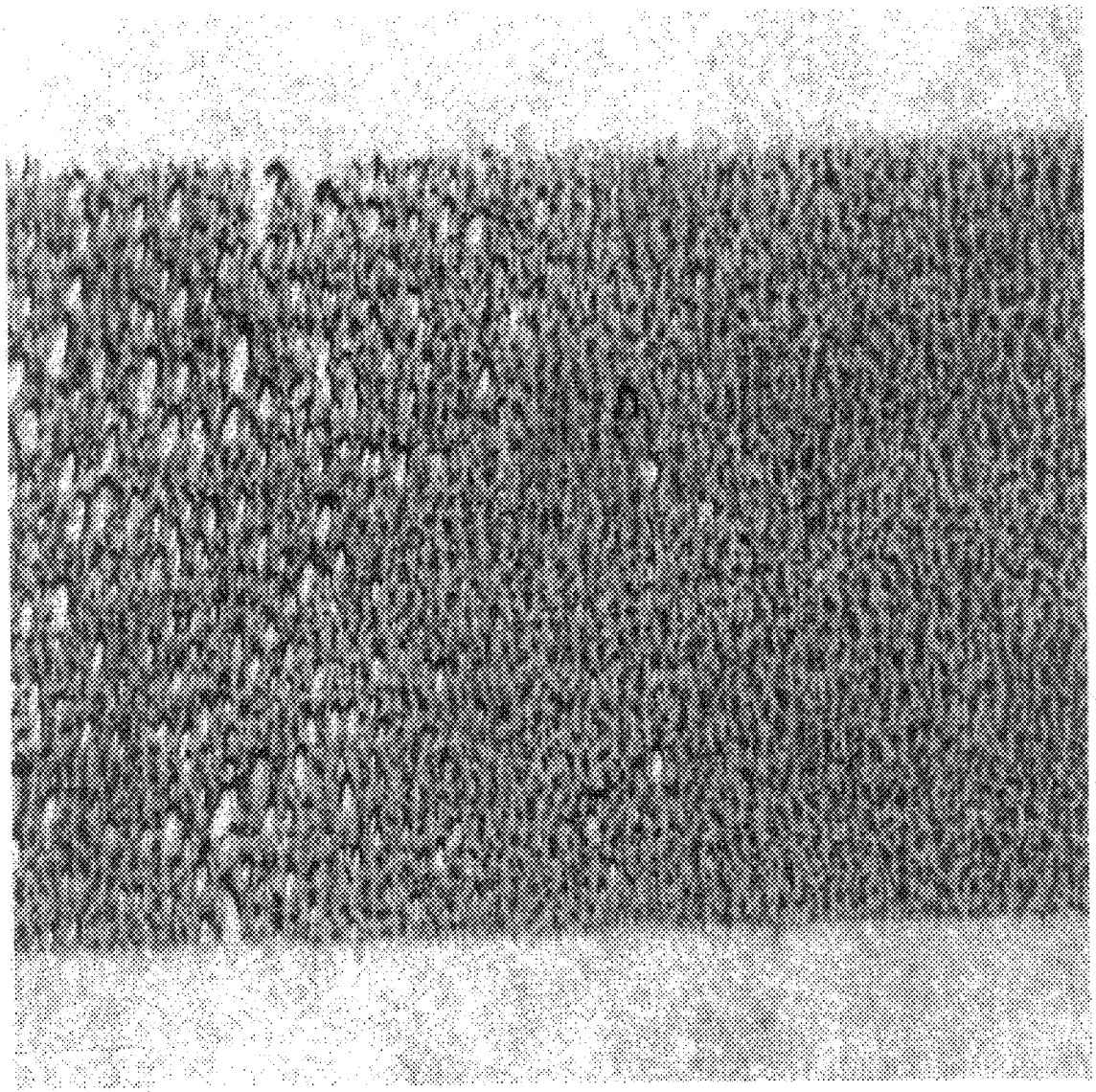
FIG. 38 illustrates in a tinted coating application an exemplary enhanced monochrome image obtained from the exemplary monochrome image of FIG. 37.

The S image is now enhanced (2104). This is accomplished as shown in FIG. 26. The idea is to find the actual difference between the lightest and darkest pixels in the S image and "stretch" this range through the entire range of possible values which is 256 because is pixel is digitized to 8 bits. The subroutine is entered (2600) and the input image (IM) is set to the S plane (2601). Next, the IM is histogrammed (2602) in the same manner as already detailed in the exemplary process flowchart of FIG. 33. From the histogram the maximum and minimum pixel values Max, and Min are obtained. The histogram shift is performed by subtracting Min from every pixel in IM (2603). The histogram stretch is performed by multiplying every pixel in IM by 255/(Max−Min) (2604). The result of these two operations result in IM being contrast enhanced, that is accentuating the difference between the darker pixel values and the lighter pixel values. An image of the enhanced S plane is illustrated in FIG. 38.

Figure 34:
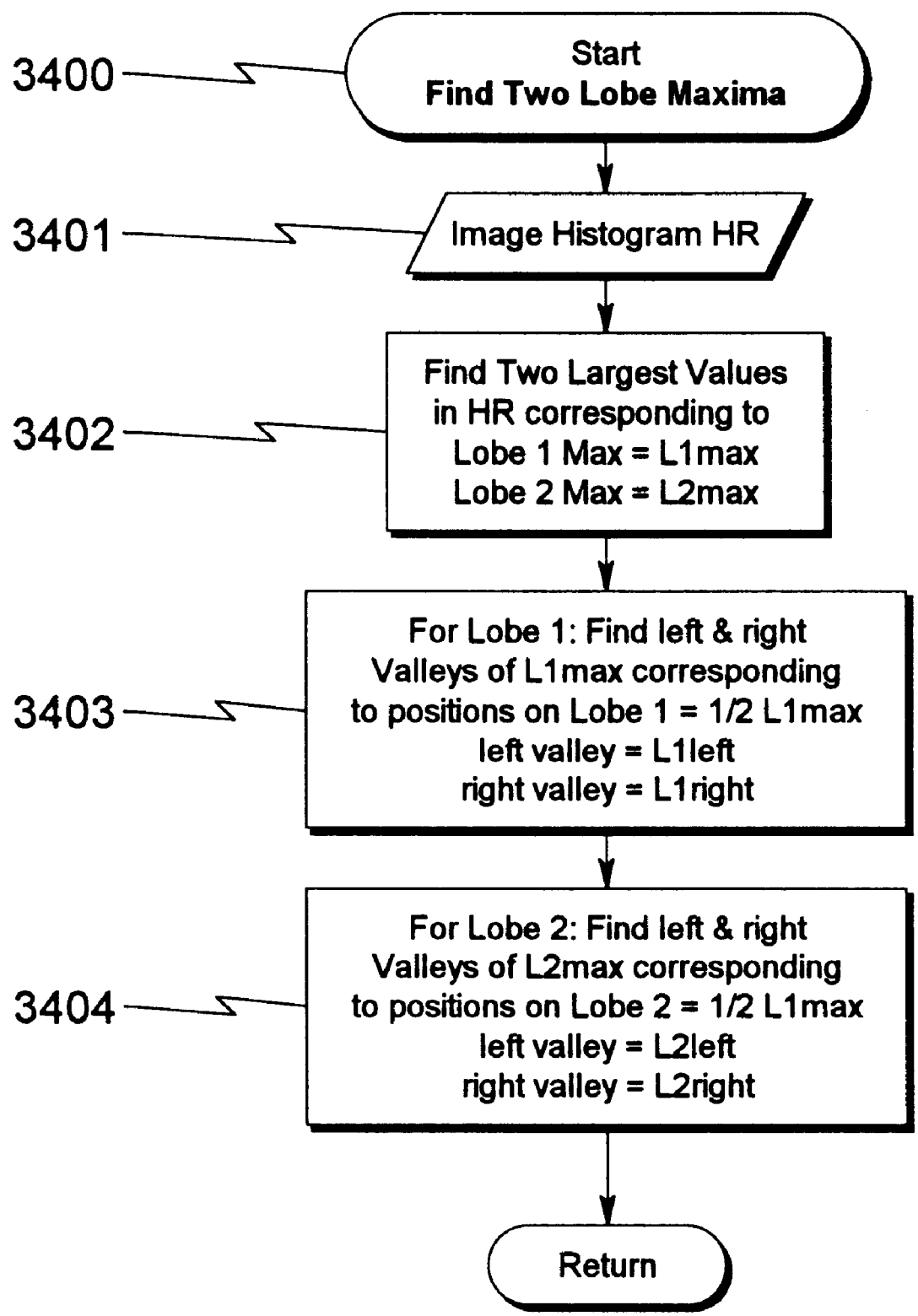
FIG. 34 illustrates an overview flowchart of an exemplary embodiment of a method taught by the present invention to calculate lobe maxima within histograms.
Figure 35:
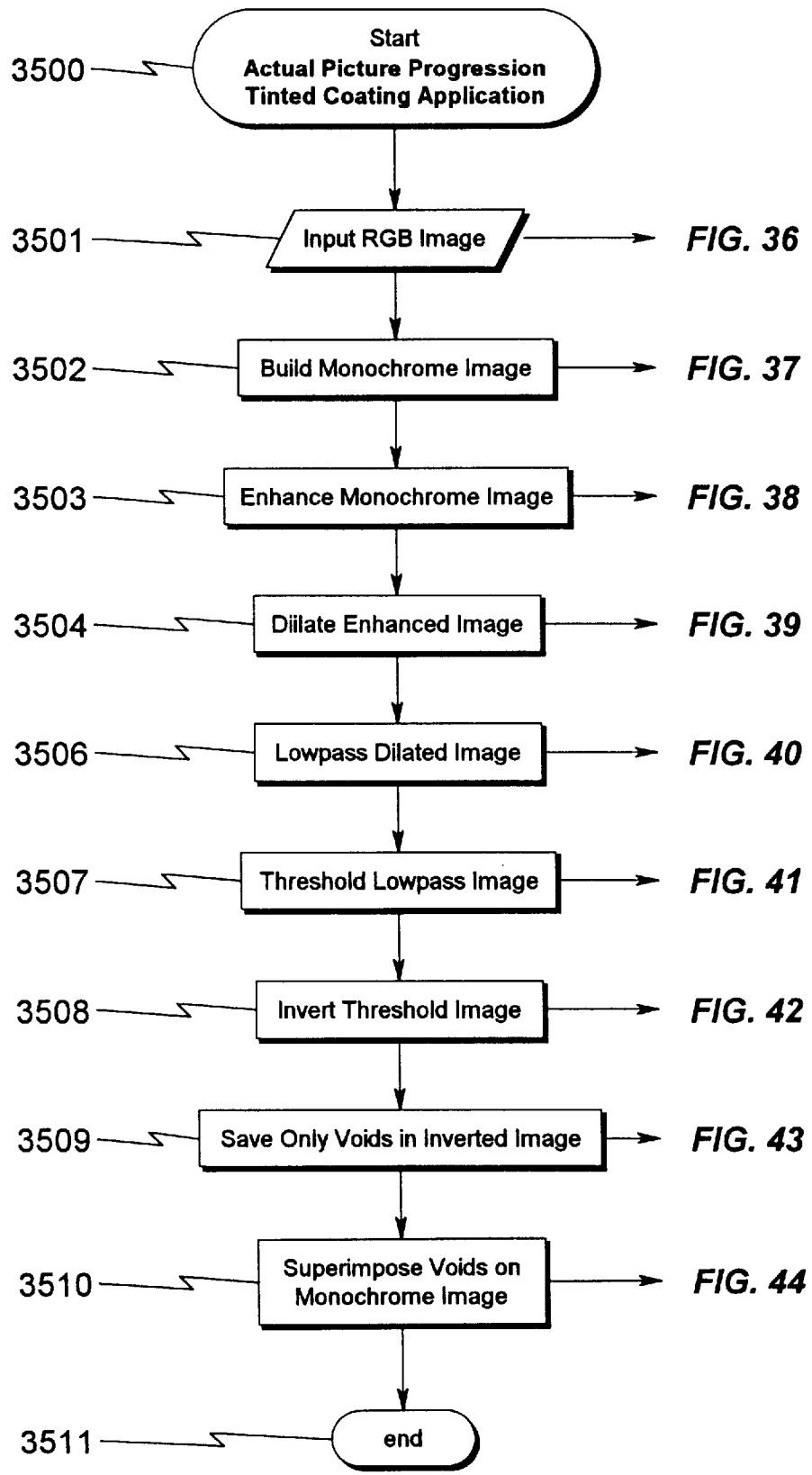
FIG. 35 illustrates an overview flowchart of an exemplary experimental image capture sequence used by a method taught by the present invention to detect voids within tinted coating applications.
Figure 39:
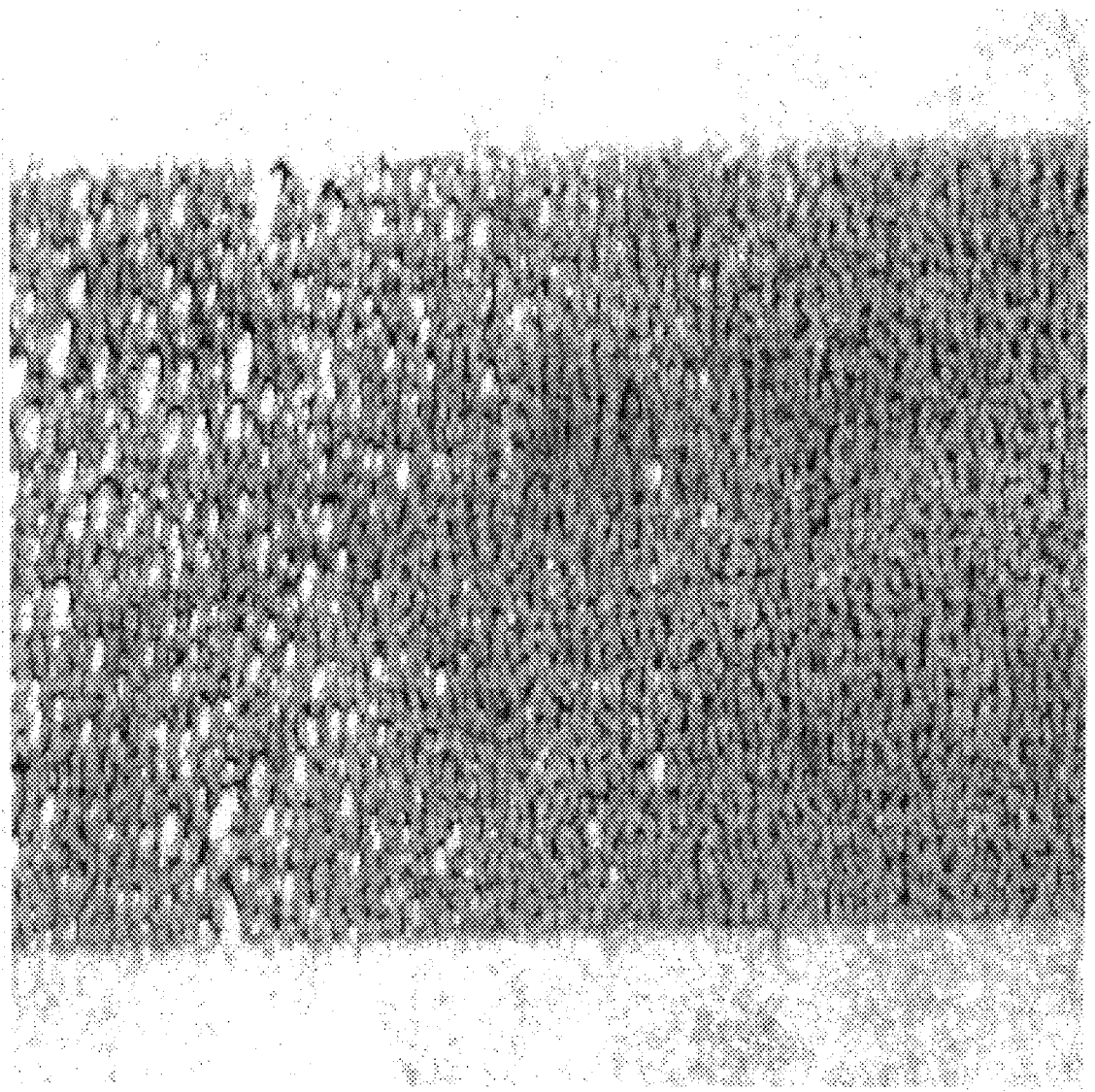
FIG. 39 illustrates in a tinted coating application an exemplary dilated image obtained from the exemplary enhanced image of FIG. 38.
Figure 40:
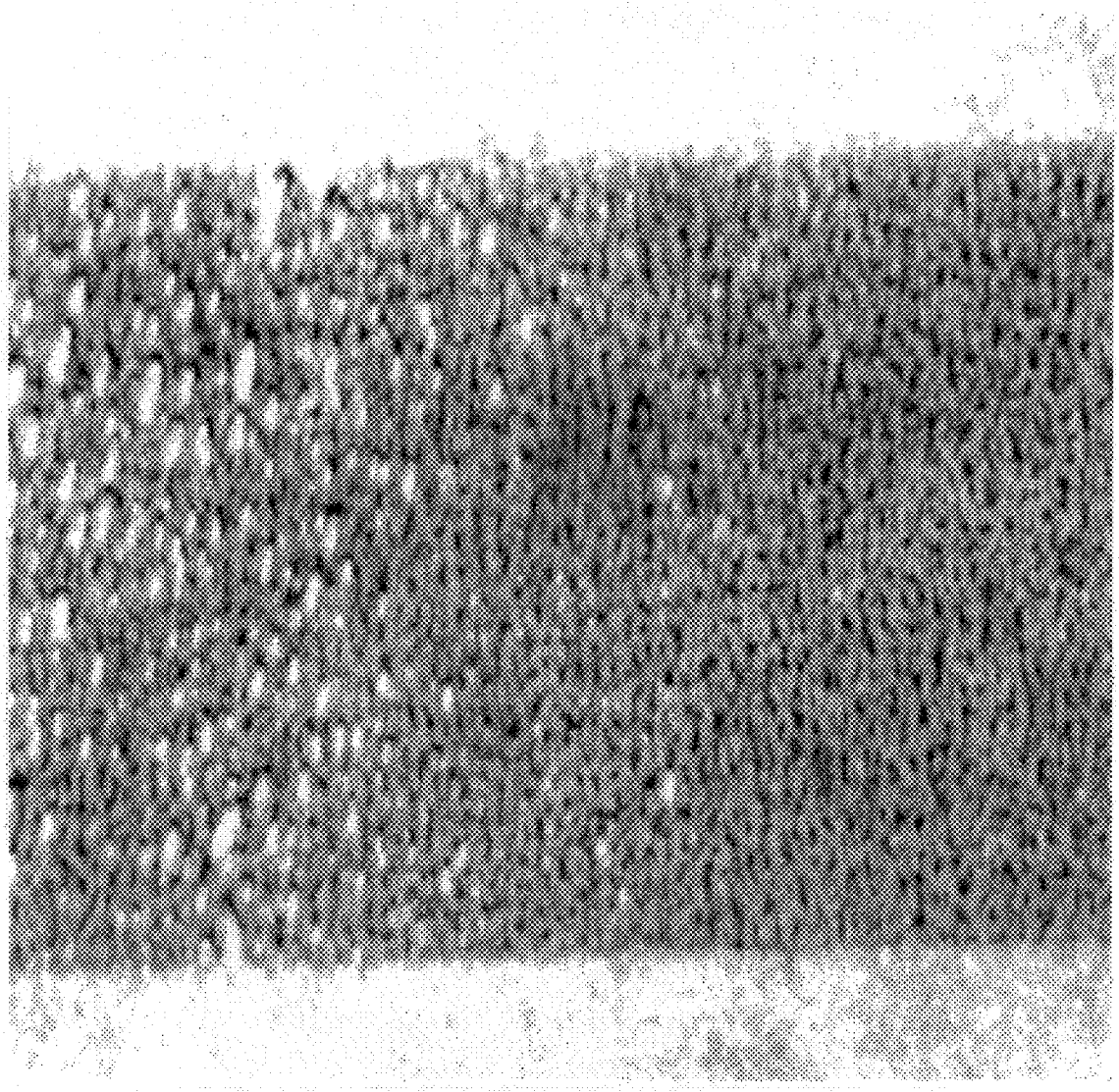
FIG. 40 illustrates in a tinted coating application an exemplary lowpass image obtained from the exemplary enhanced image of FIG. 39.
Figure 41:
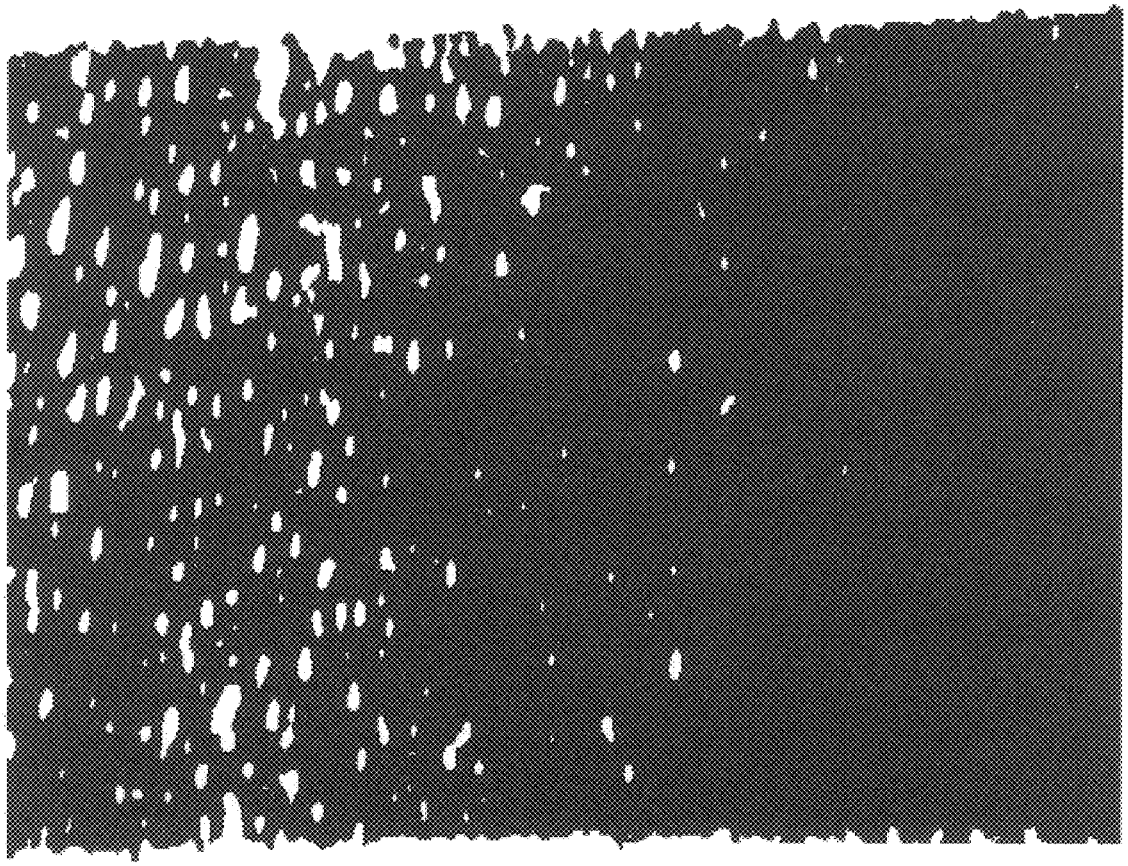
FIG. 41 illustrates in a tinted coating application an exemplary thresholded image obtained from the exemplary lowpass image of FIG. 40.
Figure 42:
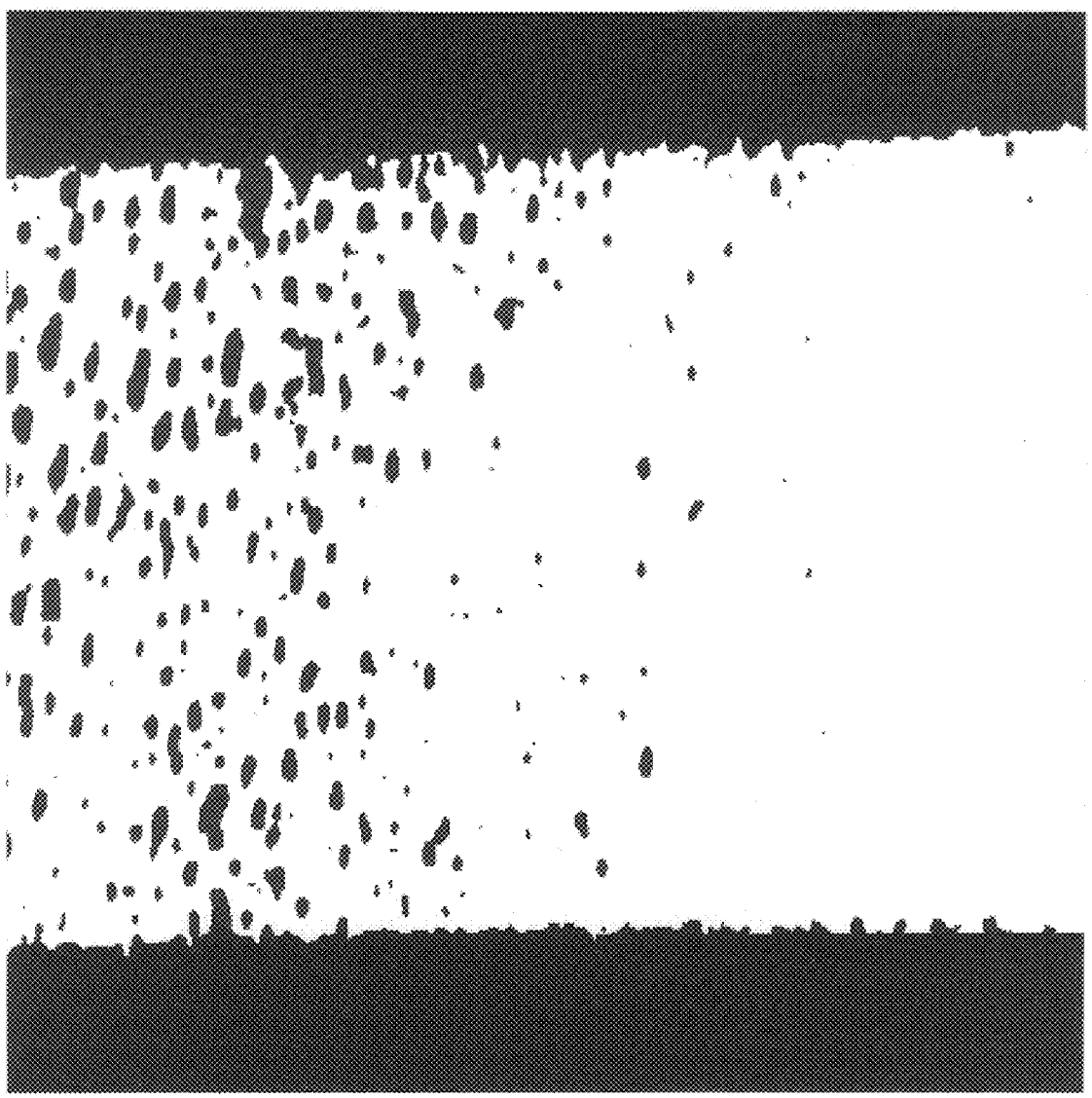
FIG. 42 illustrates in a tinted coating application an exemplary inverted image obtained from the exemplary thresholded image of FIG. 41.

Next, the enhanced S plane is dilated (2105). This process has already been detailed in the exemplary process flowchart of FIG. 27. The effect of the process is to group lighter valued pixels together thus making a lighter coating area more homogeneous. An image of the dilated S plane is illustrated in FIG. 39. Next, the S plane is low pass filtered (2106). This process has already been detailed in the exemplary process flowchart of FIG. 28. For a low pass filter operation a 3×3 kernel of all 1's and a shift value of 9 is used. This operation results in all pixels in the image being replaced by the average of those pixels and their 8 neighbors thus "blurring" or low-passing the images. This process has the effect of making the lighter and darker areas in the image even more homogeneous. An image of the low passed S plane is illustrated in FIG. 40. Next, the S plane is histogrammed (2107). This process has already been detailed in the exemplary process flowchart of FIG. 33. Because the input image, the S plane, is an image of a tinted coating on a flat background, a histogram with two major lobes will be obtained. The lobe closer to the maximum (256) will correspond to the tinted coating because the tinted coating will have a higher color saturation than the flat background. The lobe coordinates are calculated as shown in FIG. 34. First the two lobe coordinate calculation subroutine is entered (3400) with the results of the just performed histogramming operation (HR) (2401). The two largest values in the HR array are found (2402), these values are the maxima of each of the two lobes representing the substrate and the coating (L1max, L2max). Next the left and right valleys corresponding to half-power points of each lobe are calculated. This results in the values (L1left, L1right) for the lobe closest to zero (0) in the histogram array (3403) and the values (L2left, L2right) for the lobe closest to the histogram bin count (RTP using 256 levels) in the histogram array (3404). Referencing the exemplary process flowchart of FIG. 28, the next step is to threshold the S plane (2108) to obtain the saturation map (SM). The threshold value (Tv) is set to a value midway between the two lobes: Tv=L1right +(L2left−L1right). For every pixel value in the S plane less than Tv the corresponding pixel value in CM is set to zero (0). For every pixel value in S greater or equal to Tv the corresponding pixel value in CM is set to one (1). At this point the CM has a white pixel wherever there is coating and a black pixel where there is no coating. An image of the thresholded S plane is illustrated in FIG. 42 and an inverted image of the thresholded S plane is illustrated in FIG. 41.

One more check at this point is performed to insure that the tinted coating ONLY is being examined by insuring there is only one hue value in the coating map. First the CM is ANDed with the Hue plane (H) (2109). This leaves hue values corresponding to the coating in the hue plane and eliminates all others. There should be only one approximate hue value left in the image. This is guaranteed by histogramming the H plane (2110) (detailed by the exemplary process flowchart of FIG. 33) and finding the largest lobe in the histogram along with this lobes left and right valley points, Hmin and Hmax. This process has been detailed previously in the exemplary process flowchart of FIG. 34. The H plane is now band thresholded by setting all pixel values in the hue plane above and below Hmin and Hmax to 0, and all pixel values between or equal to Hmin and Hmax to 1 (2111). The resultant H plane is the checked coating map CM (2112) which will be used as input to the void detector. An exemplary image of the CM map for the tinted coating application is illustrated in FIG. 42.

Clear Coating Segmentation

Figure 22:
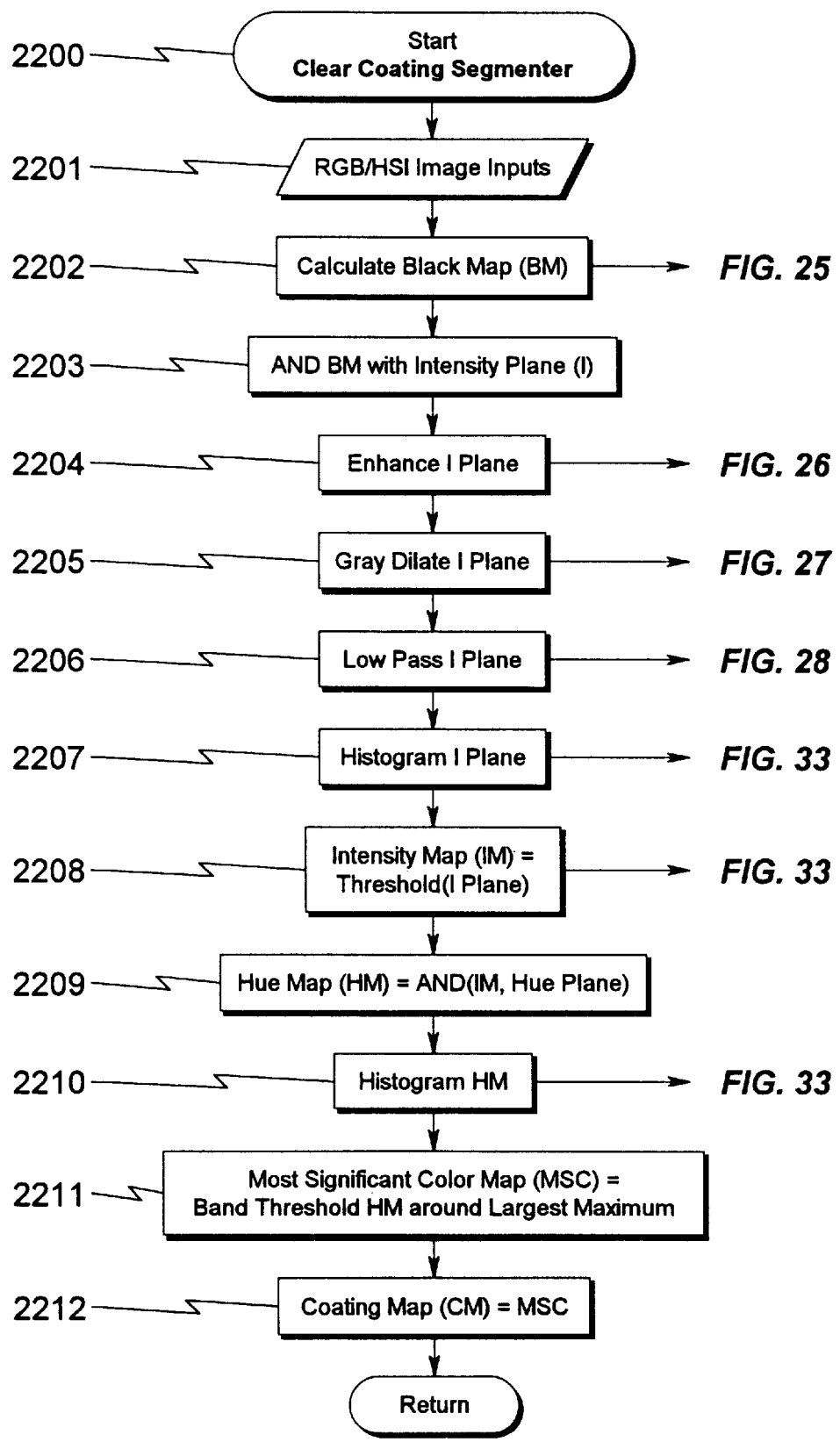
FIG. 22 illustrates an overview flowchart of an exemplary embodiment of the clear coating segmenter method taught by the present invention.
Figure 46:
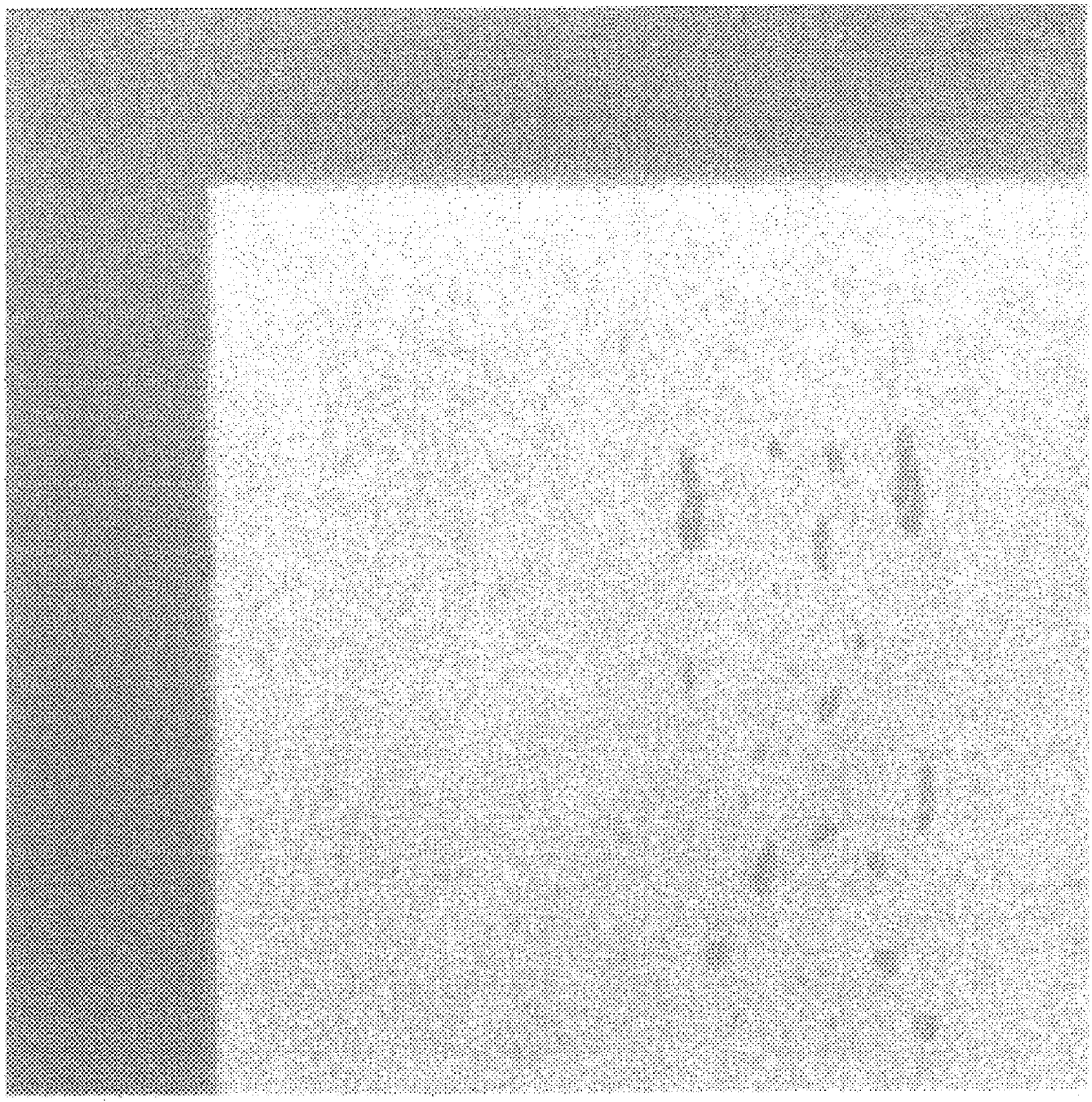
FIG. 46 illustrates in a clear coating application an exemplary intensity image obtained from the exemplary input RGB image of FIG. 36.
Figure 47:
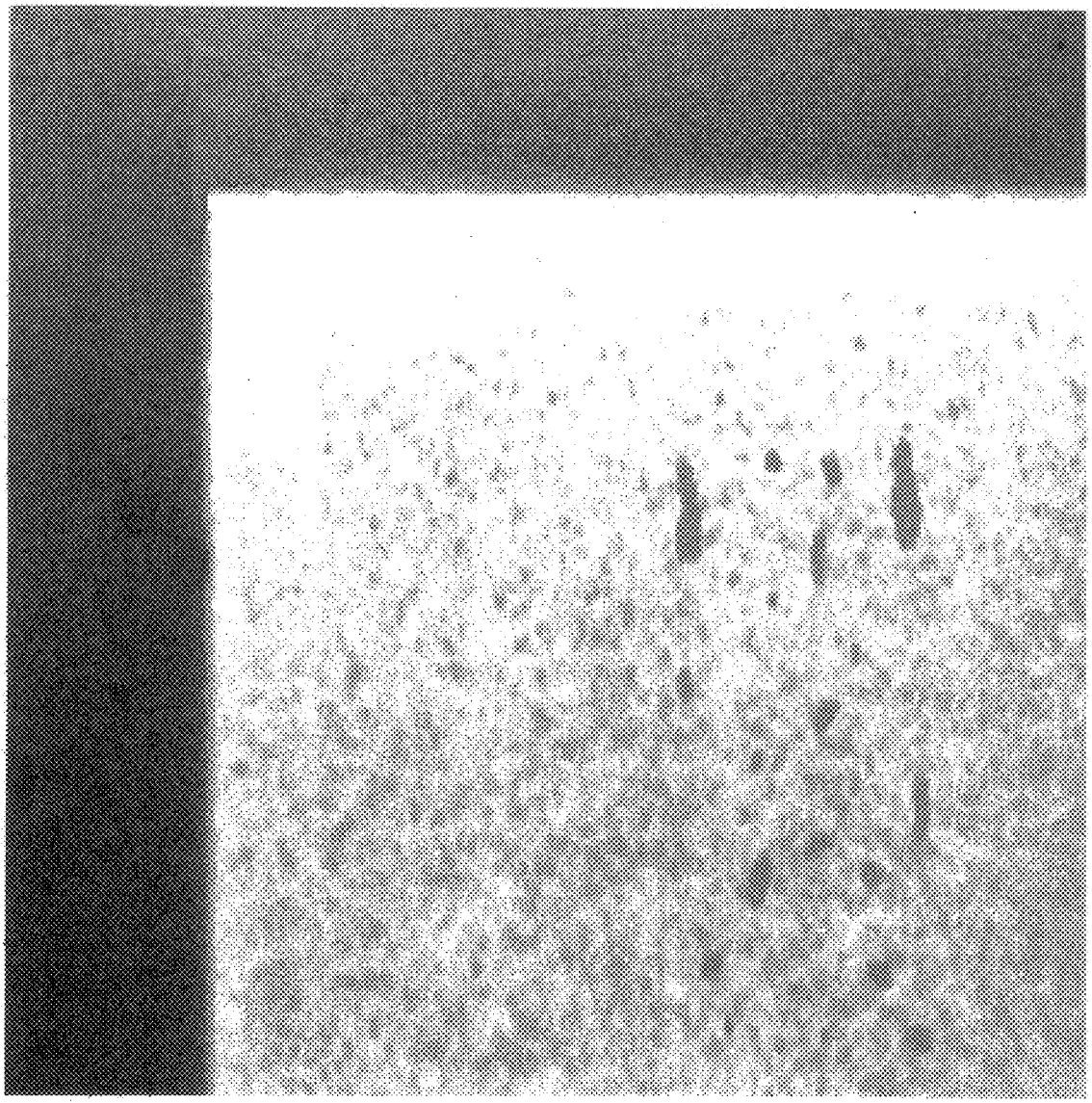
FIG. 47 illustrates in a clear coating application an exemplary enhanced intensity image obtained from the exemplary intensity image of FIG. 46.

The other specific segmentation to be considered here is Clear Coating Segmentation (FIG. 22) which uses many of the same techniques. The basic idea here is that the clear coating may have an additive which causes it to fluoresce when illuminated with a suitable source. The substrate will not fluoresce so the image obtained will have light valued pixels where there is coating and dark valued pixels for substrate. In this case, the intensity plane (I) will primarily be used for segmentation purposes. An exemplary monochrome image of a clear coating IR application is illusrated in FIG. 46. Referring to FIG. 22, clear coating segmentation starts (2200) with the input RGB images and the input HSI images (2201) of the current image to be checked for voids. The first step in segmenting the clear coating is to remove any black from the image by getting the black map (BM) (2202). Black would most likely come from the edge of the web. Black Map Segmentation has already been detailed in the exemplary process flowchart of FIG. 25. The BM is ANDed with the I plane (2203) to remove black pixels due to the edge of the web and then enhance the I plane (2204). The enhancement process has already been described in FIG. 26. An image of the enhanced I plane is illustrated in FIG. 47.

Figure 48:
FIG. 48 illustrates in a clear coating application an exemplary dilated image obtained from the exemplary enhanced image of FIG. 47.
Figure 49:
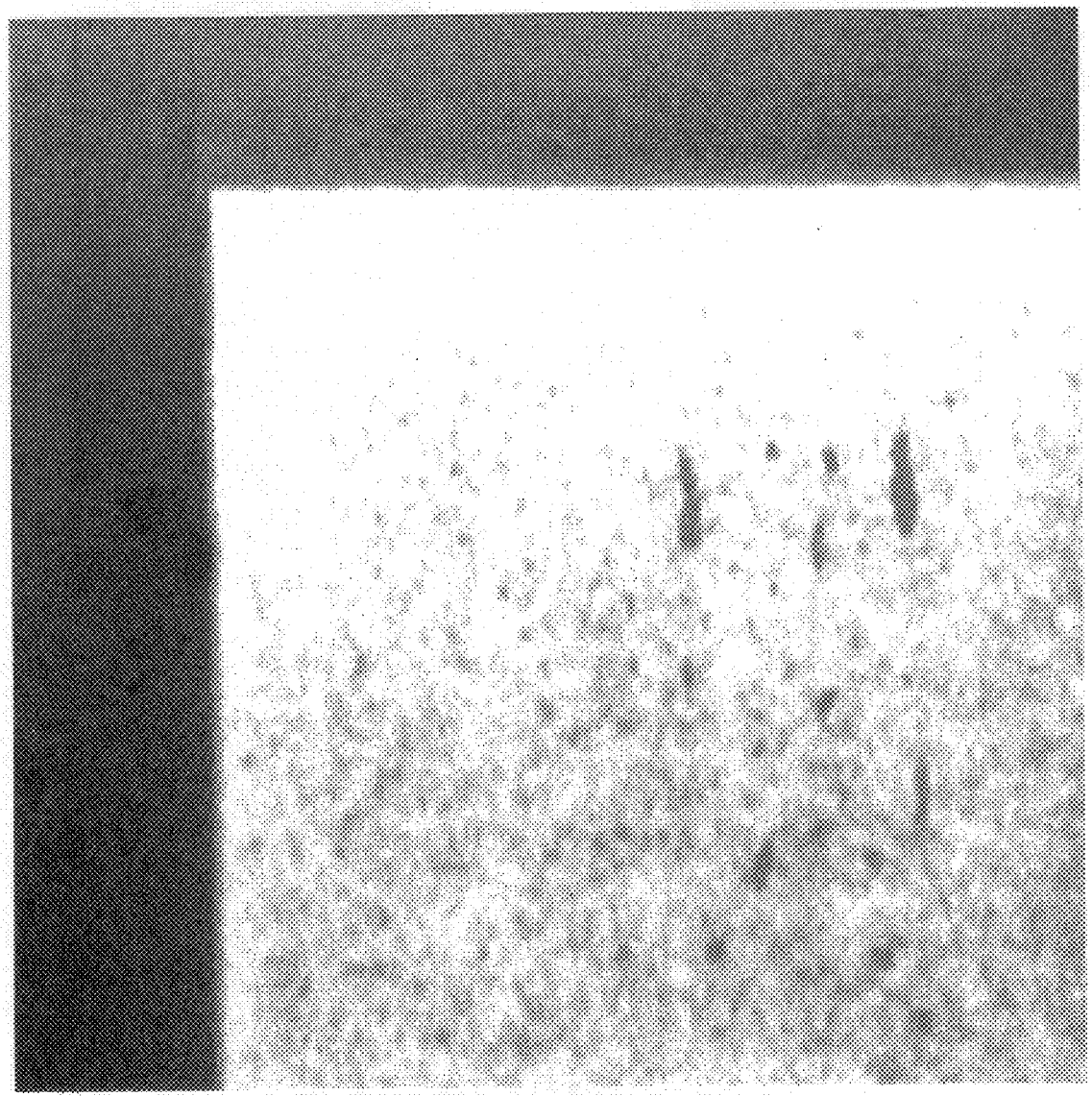
FIG. 49 illustrates in a clear coating application an exemplary lowpass image obtained from the exemplary enhanced image of FIG. 48.

Next, the I plane is gray dilated (2205) as already described in FIG. 27. An image of the dilated I plane is illustrated in FIG. 48. Next, the I plane is low-pass filtered (2206) as already described in FIG. 27. An image of the low-passed I plane is illustrated in FIG. 49. Next, the I plane is histogrammed (2207) as already detailed in the exemplary process flowchart of FIG. 33.

Figure 50:
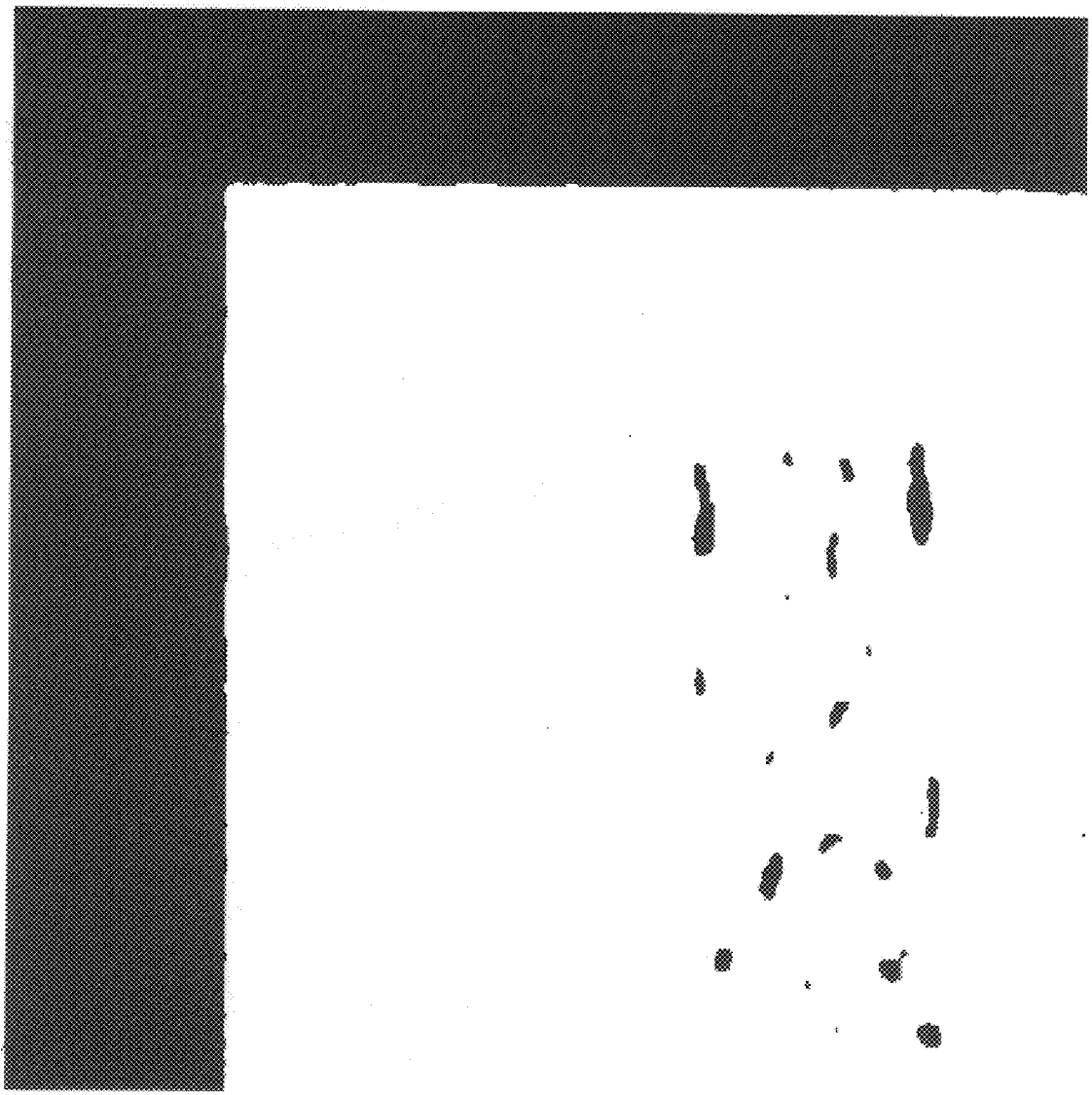
FIG. 50 illustrates in a clear coating application an exemplary thresholded image obtained from the exemplary lowpass image of FIG. 49.
Figure 51:
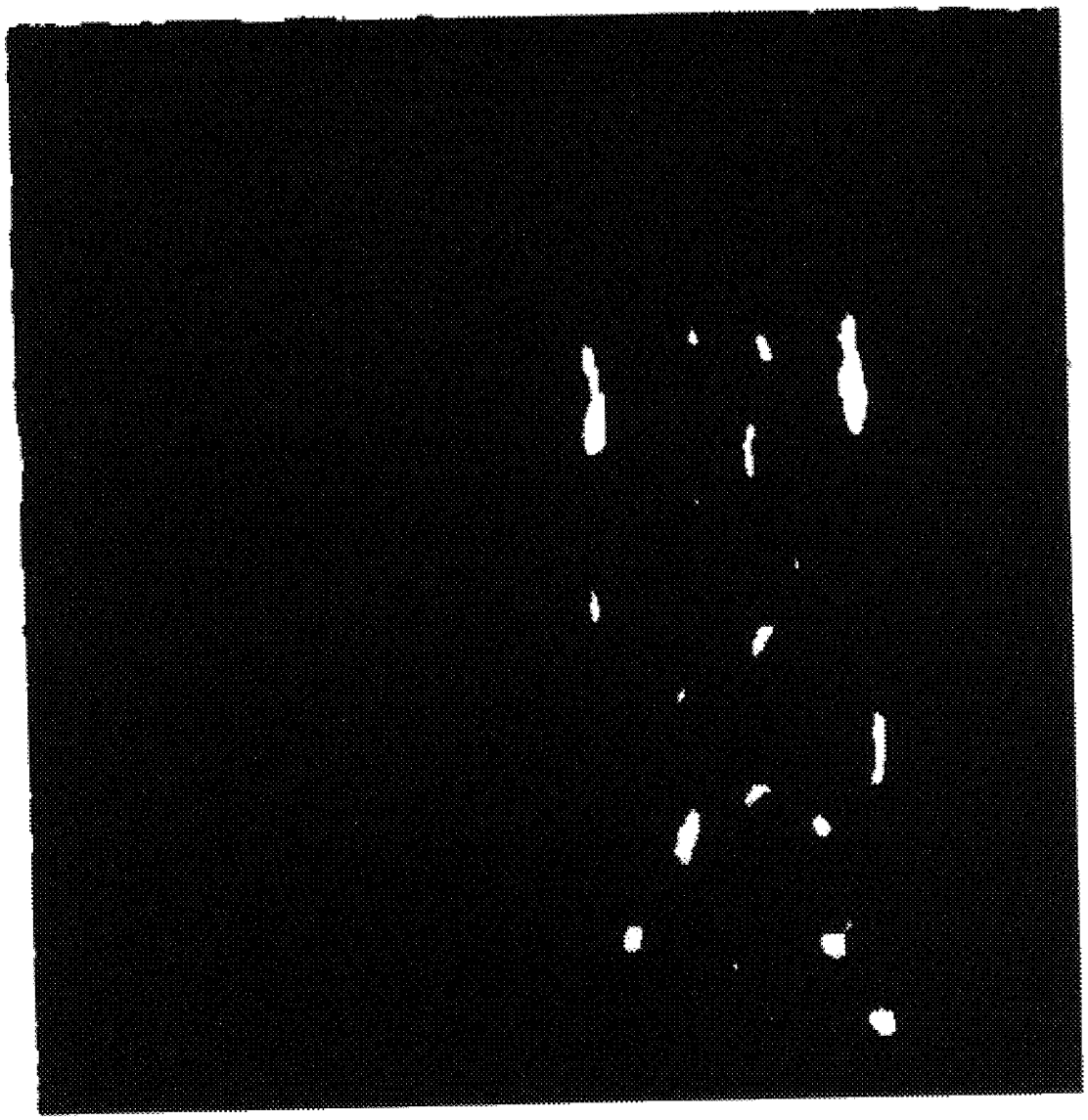
FIG. 51 illustrates in a clear coating application an exemplary inverted image obtained from the exemplary thresholded image of FIG. 50.

Next, the I plane is thresholded (2208). As in the tinted coating segmentation, a two-lobed (bimodal) histogram of the processed I plane is obtained. The upper lobe will correspond to the lighter, fluorescing coating while the lower lobe will correspond to the substrate. A threshold value Tv is determined as already described in FIG. 34. All pixel values in the I plane below Tv are set to 0 (non-coating) and all the pixel values equal to or greater than Tv are set to 1 (coating) to give an Intensity Map (IM). An image of the thresholded I plane is illustrated in FIG. 50.

As in the tinted coating segmentation one more check is performed at this point to insure that the clear coating map ONLY is being examined by insuring there is only one hue value in the coating map. First the IM plane is PNDed with the Hue plane (H) (2209). This leaves hue values corresponding to the coating in the hue plane and eliminates all others. There should be only one approximate hue value left in the image. This is guaranteed by histogramming the H plane (2210) (FIG. 33) and finding the largest lobe in the histogram along with this lobes left and right valley points, Hmin and Hmax as already describe in FIG. 34. Next, the H plane is band thresholded by setting all pixel values in the hue plane above and below Hmin and Hmax to 0, and all pixel values between or equal to Hmin and Hmax to 1 (2211). The resultant H plane is the checked coating map CM (2212) which will be used as input to the void detector. FIG. 50 represents the CM at this point for the clear coating segmentation application with IR illumination.

Coating Void Detector

At this point, the defect detection process depends on the coating map (CM) which is an image consisting of only two pixel values: 0 for non-coating and 1 for coating. The CM is illustrated in FIG. 42 for the tinted coating application and FIG. 50 for the clear coating application. The objective now is to find voids or small holes within homogeneous areas of coating (the CM map) which would indicate the coating is not being applied properly.

Figure 23:
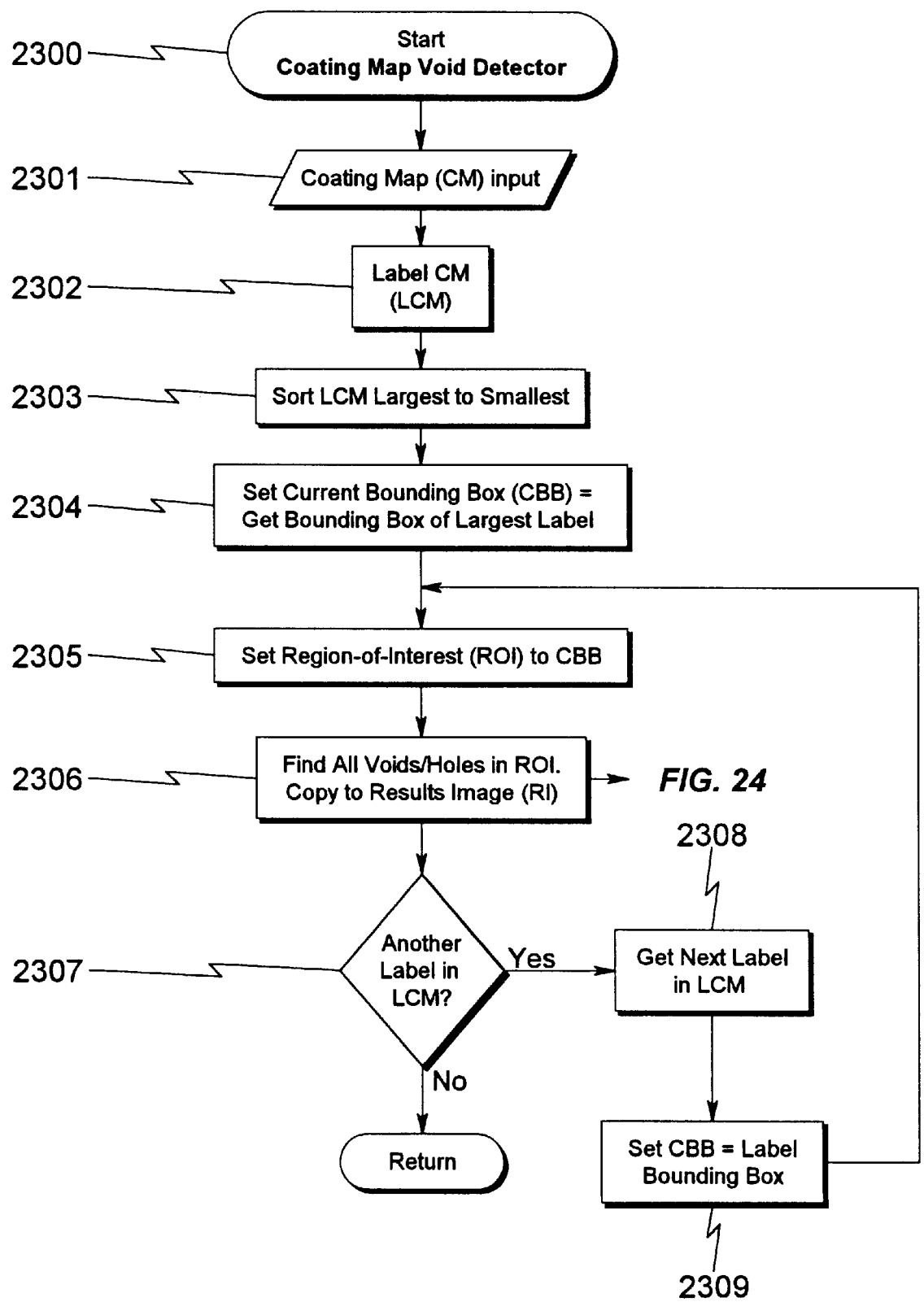
FIG. 23 illustrates an overview flowchart of an exemplary embodiment of the coating map void detector method taught by the present invention.

Referring to FIG. 23, the void detection subroutine is entered at (2300). The input to the void detector is the coating map (CM) from either of the two segmentation procedures that have been described so far (2301). First, the CM is labeled (2302). This is a two-pass image processing function which assigns all set 8-connected pixels (any pixel that has a value of one immediately adjacent on any diagonal to another set pixel) the same numeric label value. This is typically accomplished via the use of an image processing runtime system library subroutine call (RTP using an IMAGING TECHNOLOGY supplied software routine).

For example, IMAGING TECHNOLOGY supplies a library of image processing routines, some of which may be used in this application. This library is called the ITEX-IPL Image Processing Library. A typical labeling function call is label(Image, ObjectVal, Connect, Lminval, Lmaxval, LabelCount), where Image=the image to be labeled, ObjectVal=the pixel value in the image to be labeled (in this case 1), Connect=8 Connected or 4 Connected, in this case 8 connected, Lminval and Lmaxval=the minimum and maximum label values assigned respectively, and Count=the number of labels created by the operation. The function itself returns a pointer to a label list which is a linked list of all the found labels in the image. As a result of this function call, all pixels with the same numeric label value belong to the same label. This numeric value and the number of pixels that belong to it are returned in the label list (LCM) which is output from this function call.

The next step is to sort the LCM largest to smallest (2303) using an image processing runtime system library subroutine call (RTP using an IMAGING TECHNOLOGY supplied routine). A typical runtime routine function call format is label_measure_sort( LabelList, Mindex, Sortorder ) where LabelList is in this case the LCM, Mindex indicates what measure the list is to be sorted on, in this case Mindex is set to 0 so the sort is based on label area, and Sortorder indicates whether the sort should be done greatest to least or least to greatest, in this case Sortorder is set to greatest to least= DECREASING_SIZE. The function returns a pointer to the sorted label list, in this case LCM. The LCM is now cycled through, retrieving the first (and largest) label. By reading the numeric label value for this label, the CM is analyzed to find all pixels that belong to this label.

The minimum X and Y and the maximum X and Y extents of the pixels of this label are typically found using an image processing runtime system library function call (RTP using IMAGING TECHNOLOGY supplied routines). To find the minimum and maximum X's and Y's of the bounding box of this label the following runtime system routines are typical of what may be used to implement this functionality:

label_get bxmax(Label),
label_get_bxmin(Label),
label_get_bymax(Label), and
label_get_bymin(Label)

where Label is the current label being analyzed from the LCM and each function returns its corresponding bounding box coordinate. This gives us a bounding box (CBB) which completely encompasses the label (2304). At this point, the region-of-interest (ROI) for all subsequent image processing operations is now set to the CBB (2305). The job now is to find all holes or voids on the interior of the label being analyzed within the ROI (2306).

Void Finder

Figure 24:
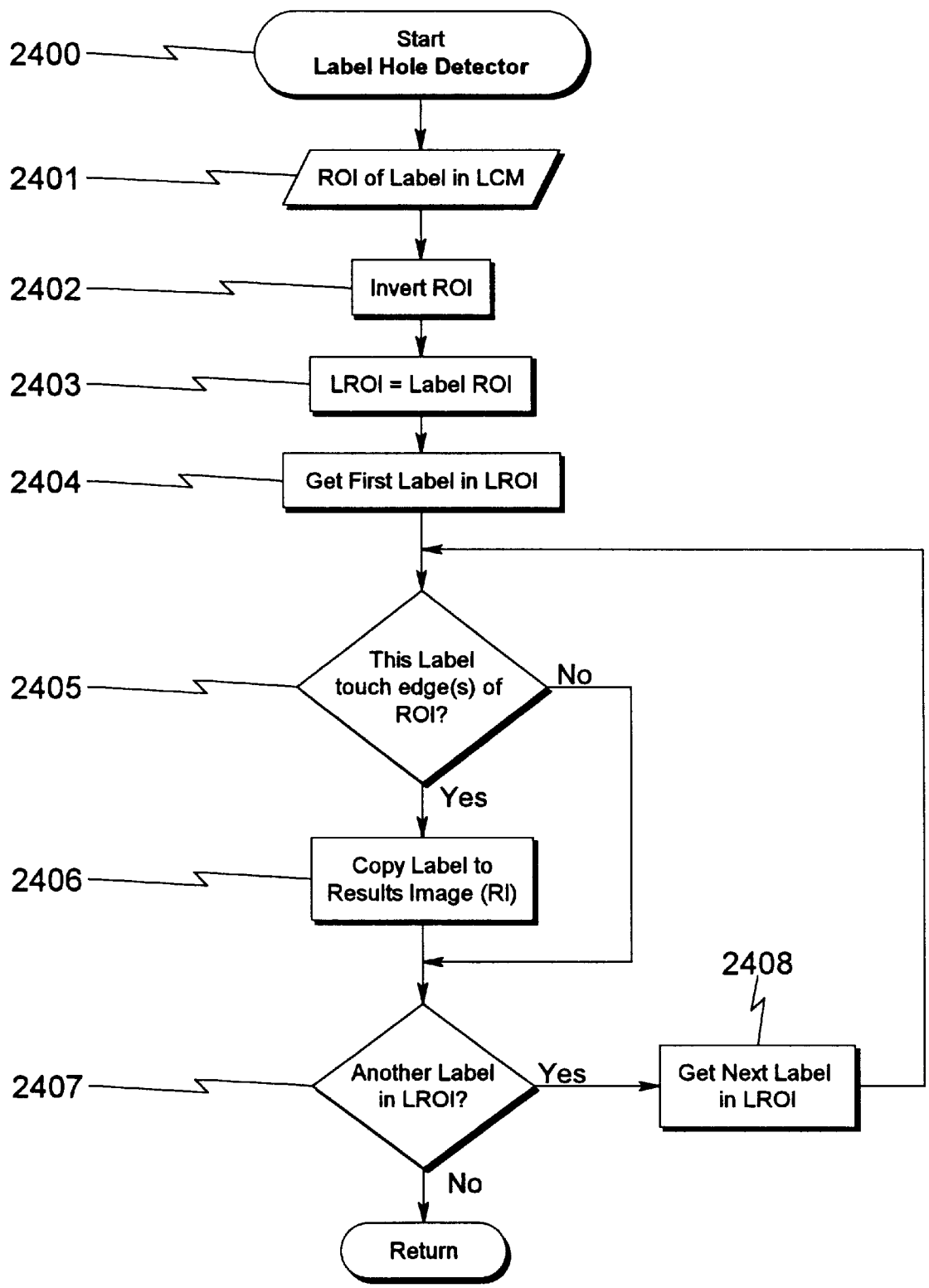
FIG. 24 illustrates an overview flowchart of an exemplary embodiment of a method taught by the present invention to label void holes.

Referring to FIG. 24, the void finder subroutine is entered at (2400). Input to the routine is the ROI of the LCM label determined previously (2401). First, all the pixels within the ROI are inverted: all pixels set to 0 are set to 1 and vice-versa (2402). This will have the effect of setting all hole pixels to as well as pixels outside the boundary of the label but inside the ROI. All other pixels will be set to zero (0). The ROI is now labeled using image processing runtime library subroutines described above (RTP using IMAGING TECHNOLOGY routines) and cycle through the label list LROI (2403).

The first label in the LROI is obtained (2404). This label is checked to see if it touches the ROI anywhere (2405) using an image processing runtime library subroutine call (RTP using IMAGING TECHNOLOGY routines) which checks each pixel in the label to see if it lies on the ROI boundary. A typical function call for this routine is label_get_touches(Label) where Label is the current label being analyzed and the function returns a non-zero value if the label touches the ROI anywhere, 0 is returned if the label does not touch the ROI. If no part of the label touches the ROI boundary, then this label is internal to the coating label and represents a void within it. This label is therefore copied to the result image (RI) (2406). At this point the next step is to check the label list LROI for another label from the labeled ROI (2407). If there is another label, it is read and again check if any pixel of this label touches the boundary of the ROI (2405). If there are no more labels in the ROI, this particular label is finished.

Coating Void Detector

Figure 43:
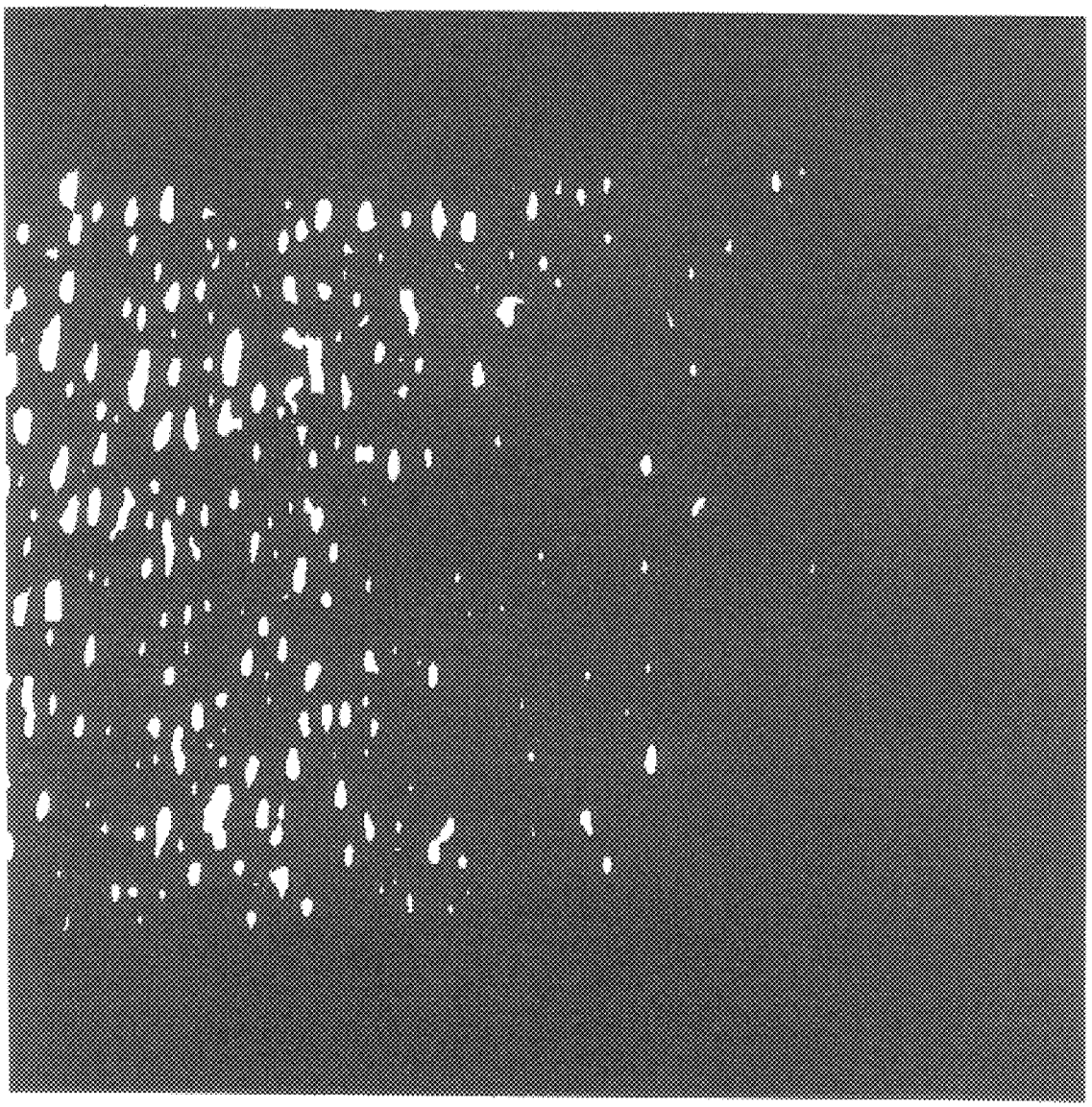
FIG. 43 illustrates in a tinted coating application an exemplary void display image obtained from the exemplary inverted image of FIG. 42.

Referencing the exemplary process flowchart of FIG. 23, the LCM is now checked to see if it contains another label (2307). If there is, the next label is read (2308). The minimum X and Y and the maximum X and Y extents of the pixels of this label in the image using an image processing runtime system library subroutine call (RTP using an IM4AGING TECHNOLOGY supplied routine) as described above. This results in a new bounding box (CBB) of this label which completely encompasses the label (2309). Cycling back in the subroutine, the region-of-interest (ROI) for all subsequent image processing operations is set to the CBB (2305) just as before and the ROI is analyzed for voids. This process continues for each label in the LCM. When all labels in the LCM have been analyzed then there are no more labels to check (2307). This process returns the result image (RI) which contains an image of all voids within the coating image. An exemplary image of the interior voids for the tinted coating application is illustrated in FIG. 43 and in for the clear coating application in FIG. 52.

Void Error Checking and Reporting

At this point it is necessary to determine if any of the voids are large enough to warrant warning the operator. Referencing-the exemplary process overall block diagram of FIG. 20, the detected voids need to be analyzed to determine whether any of the detected voids is greater than a warning size previously entered by the operator (2006). This process is detailed in the exemplary process flowchart of FIG. 30.

Figure 30:
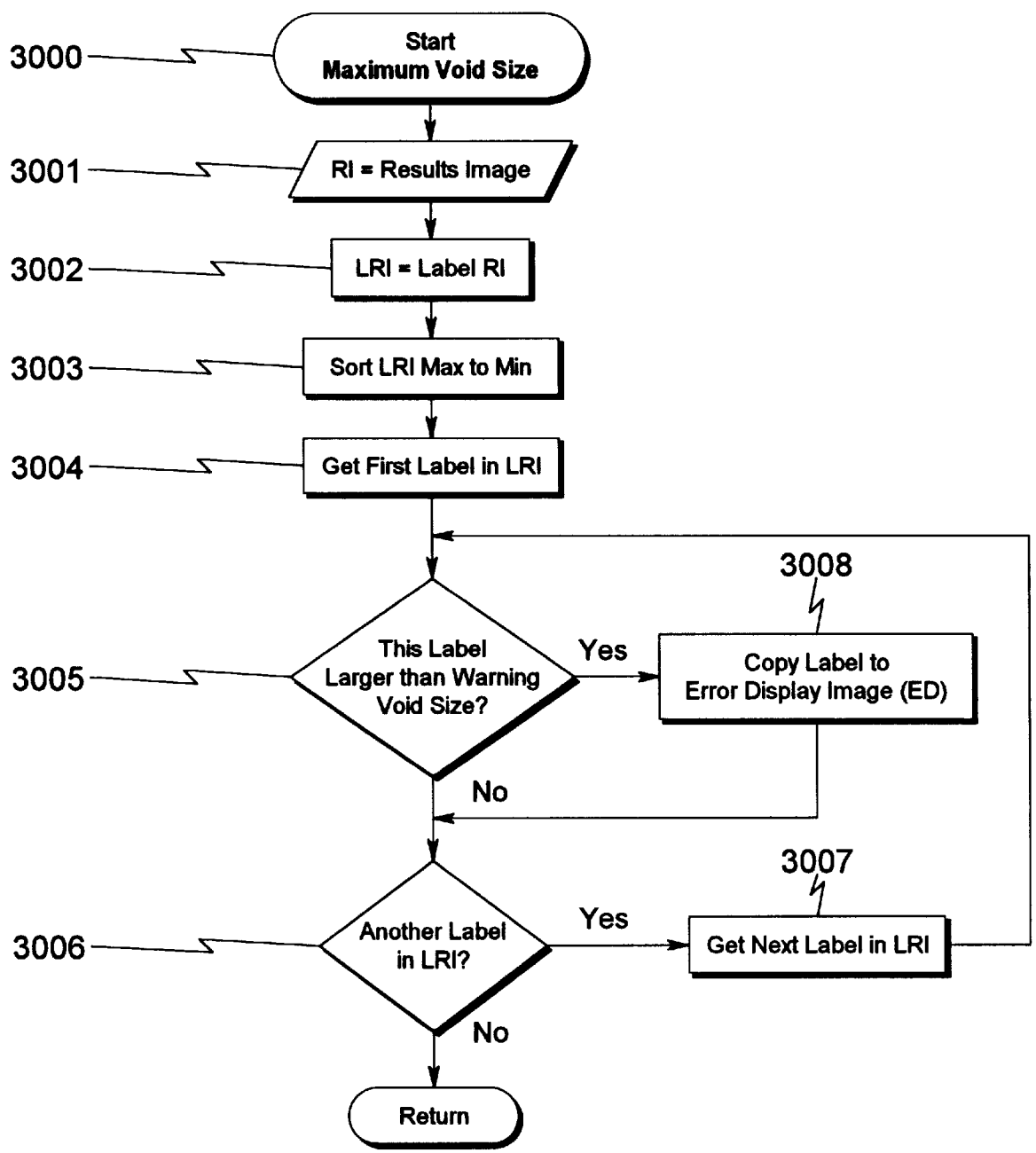
FIG. 30 illustrates an overview flowchart of an exemplary embodiment of a method taught by the present invention to determine the maximum void size present in a coating image.
Figure 52:
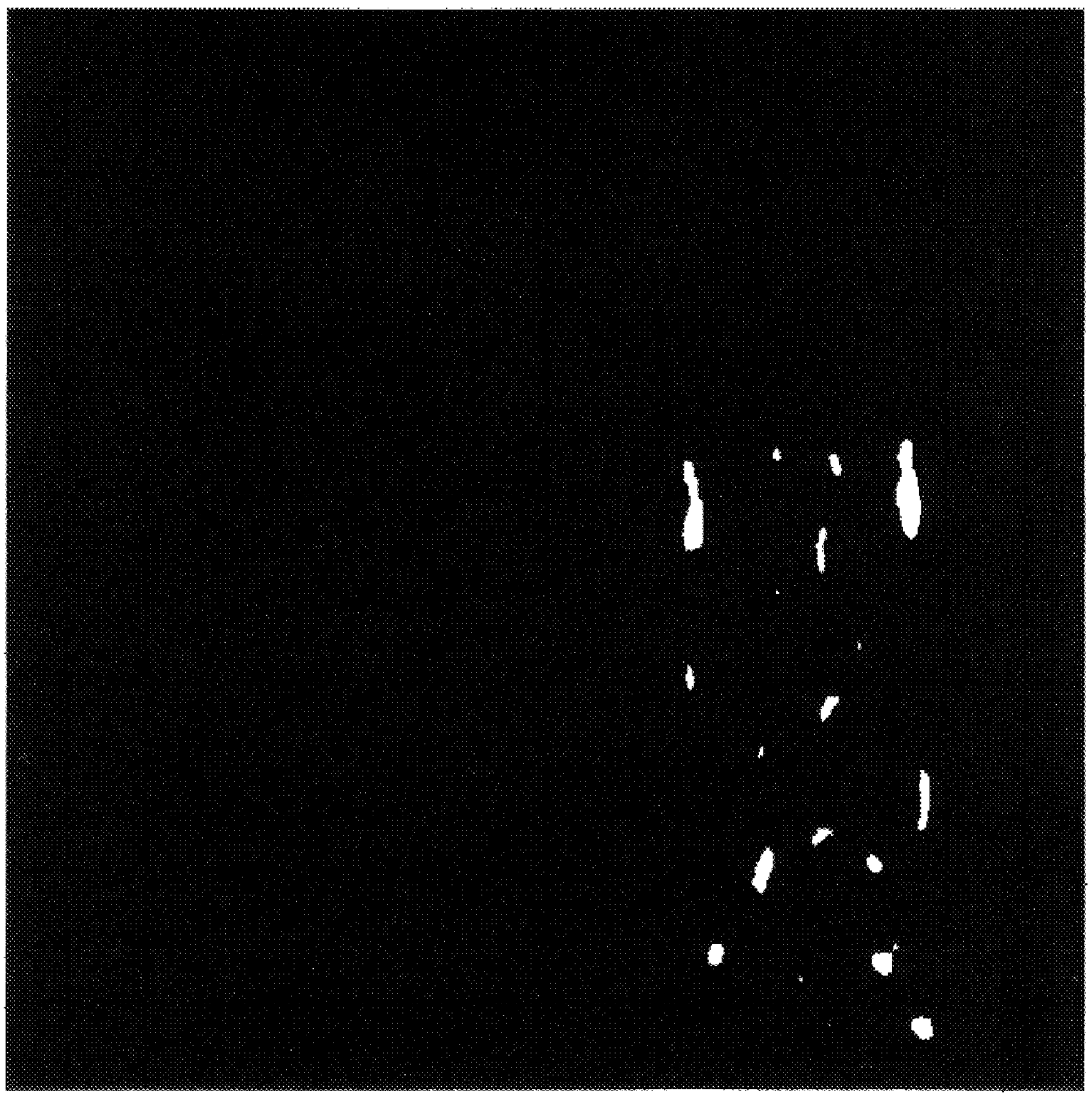
FIG. 52 illustrates in a clear coating application an exemplary void display image obtained from the exemplary inverted image of FIG. 51.

Referring to FIG. 30, the maximum void detector is entered at (3000). The input to this subroutine is the RI from the void detector (3001) (RTP void images are illustrated in FIG. 43 and FIG. 52 for tinted and clear coating respectively, these images would be input to this subroutine) First the RI is labeled using an image processing runtime system library subroutine call (RTP using an IMAGING TECHNOLOGY routine already described) (3002). The result of this operation is termed the RI label list LRI. Next the LRI is sorted based on size, maximum to minimum using a sort routine (RTP using an IMAGING TECHNOLOGY supplied sorter) already described (3003). The first label in the sorted LRI (which will be the largest) is then obtained (3004).

The width and length of this label using IMAGING TECHNOLOGY supplied routines described above are obtained and compared against the operator input maximum allowable void warning size (3005). If the width or length of the label is greater than the warning size this label is copied to the Error Display (ED) image (3008). Next, the LRI is checked to see if it contains another label (3006). If there is another label, the next label in the LRI is read (3007), the width and length of this label using an image processing runtime system library subroutine call (RTP using IMAG- ING TECHNOLOGY supplied routines) described above is obtained and compared against the operator input maximum allowable void warning size (3005) as before. This process is continued for all labels in the LRI. At the conclusion of this routine, if there are any labels in the ED, an operator warning condition exists.

Referencing the exemplary process overall block diagram of FIG. 20, if the results of the void size check (2006) as just described result in at least one error label copied to the ED, any void error labels in the ED must be displayed to the operator (2007). This process is detailed in the exemplary process flowchart of FIG. 31.

Figure 31:
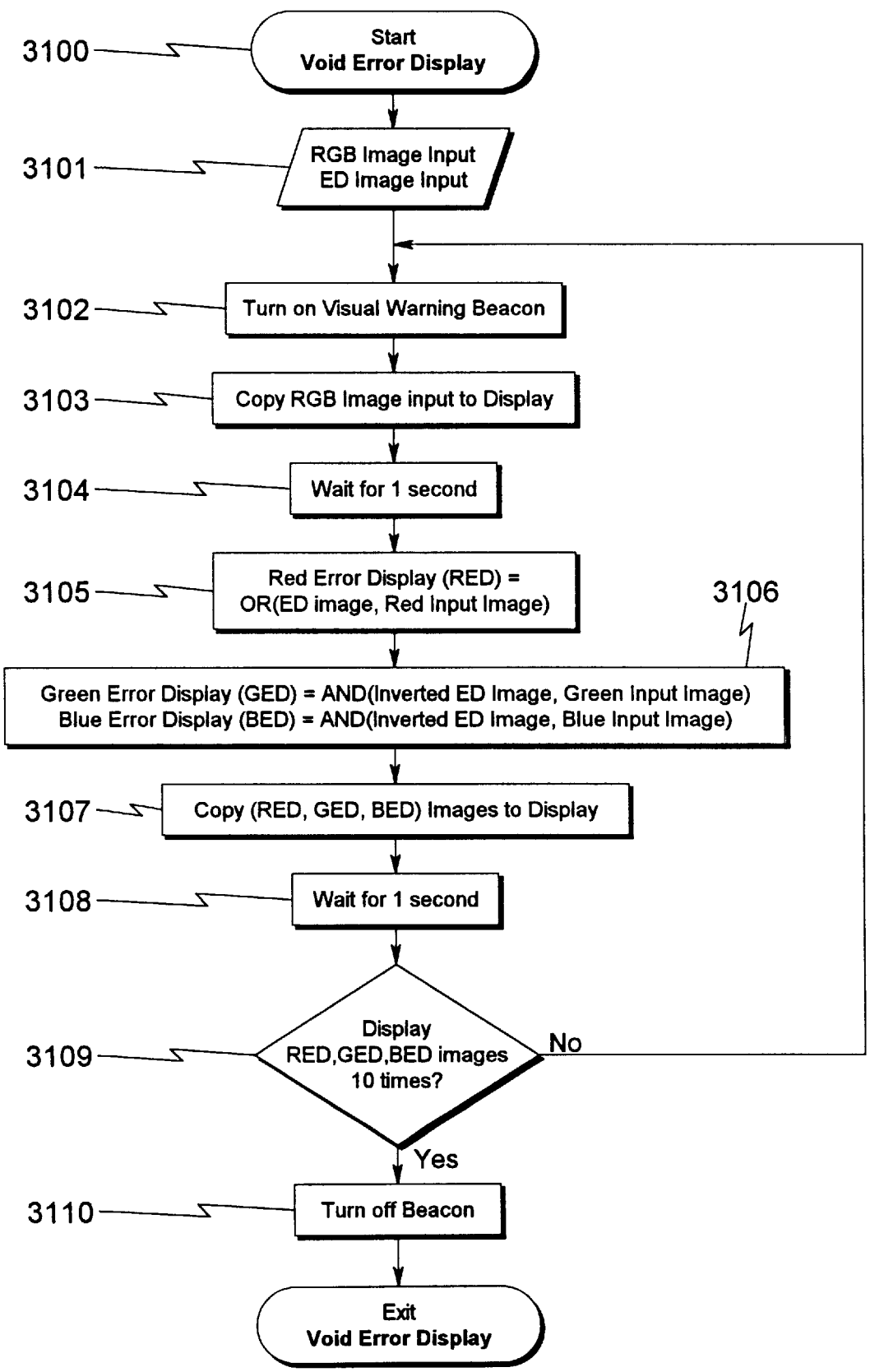
FIG. 31 illustrates an overview flowchart of an exemplary embodiment of a method taught by the present invention to provide an operator display of the voids detected by the present invention.

Referring to FIG. 31, the void error display subroutine is entered at (3100). Inputs to the void error display are the original RGB image inputs and the ED as described above (3101). First the Warning Beacon is turned on (3102) which will call the operators attention to the display monitor. Next, the RGB images are copied to the operator display monitor causing the input RGB image to be immediately displayed to the operator (3103). Then a wait loop of 1 second is entered (3104) so the RGB image remains on the operator display monitor for 1 second. Next, the Input R image is logically ORed with the ED image and the result is copied to the Red Error Display image (RED) (3105). This operation has the effect of not disturbing the original input R image except where an error label is where the RED image is set to 255, the highest intensity red. Next the Input G and B images are logically ANDed with the inverted ED image and the results are copied to the Green and Blue Error Display Images respectively (GED, BED) (3106). This operation has the effect of not disturbing the original input G and B images except where an error label is where the GED and BED images are set to 0, the lowest intensity green and blue respectively. Next the RED, GED, BED images are copied to the operator display monitor (3107) where they are immediately viewed by the operator. The operator will see at this point the normal input RGB images except where there are void errors which will be displayed in bright red. A wait loop of 1 second is now entered (3108) so the RED, GED, BED images remain on the monitor for 1 second.

Figure 44:
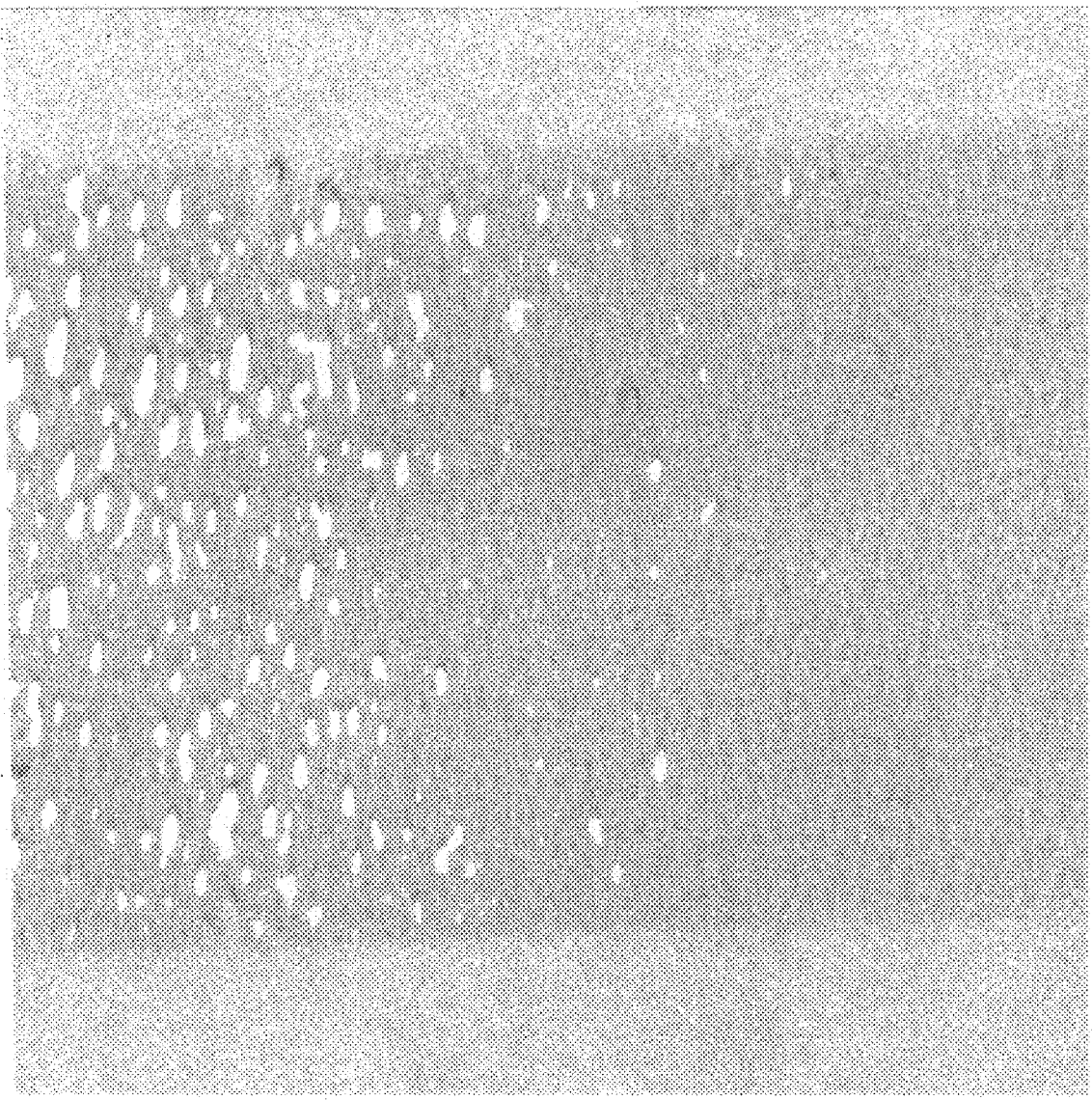
FIG. 44 illustrates in a tinted coating application an exemplary superimposed void display image obtained from the void display image of FIG. 43.
Figure 45:
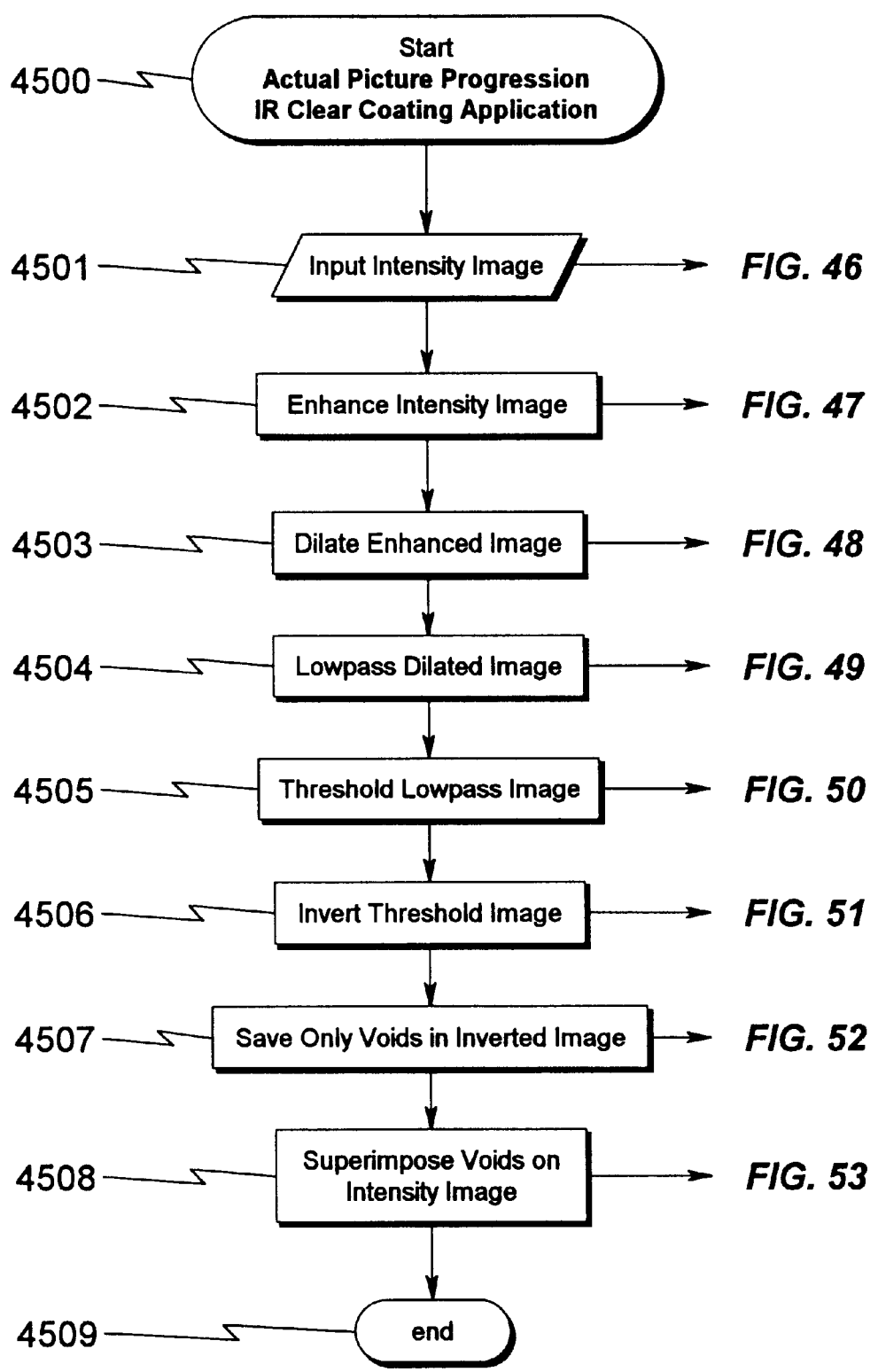
FIG. 45 illustrates an overview flowchart of an exemplary experimental image capture sequence used by a method taught by the present invention to detect voids within clear coating applications.
Figure 53:
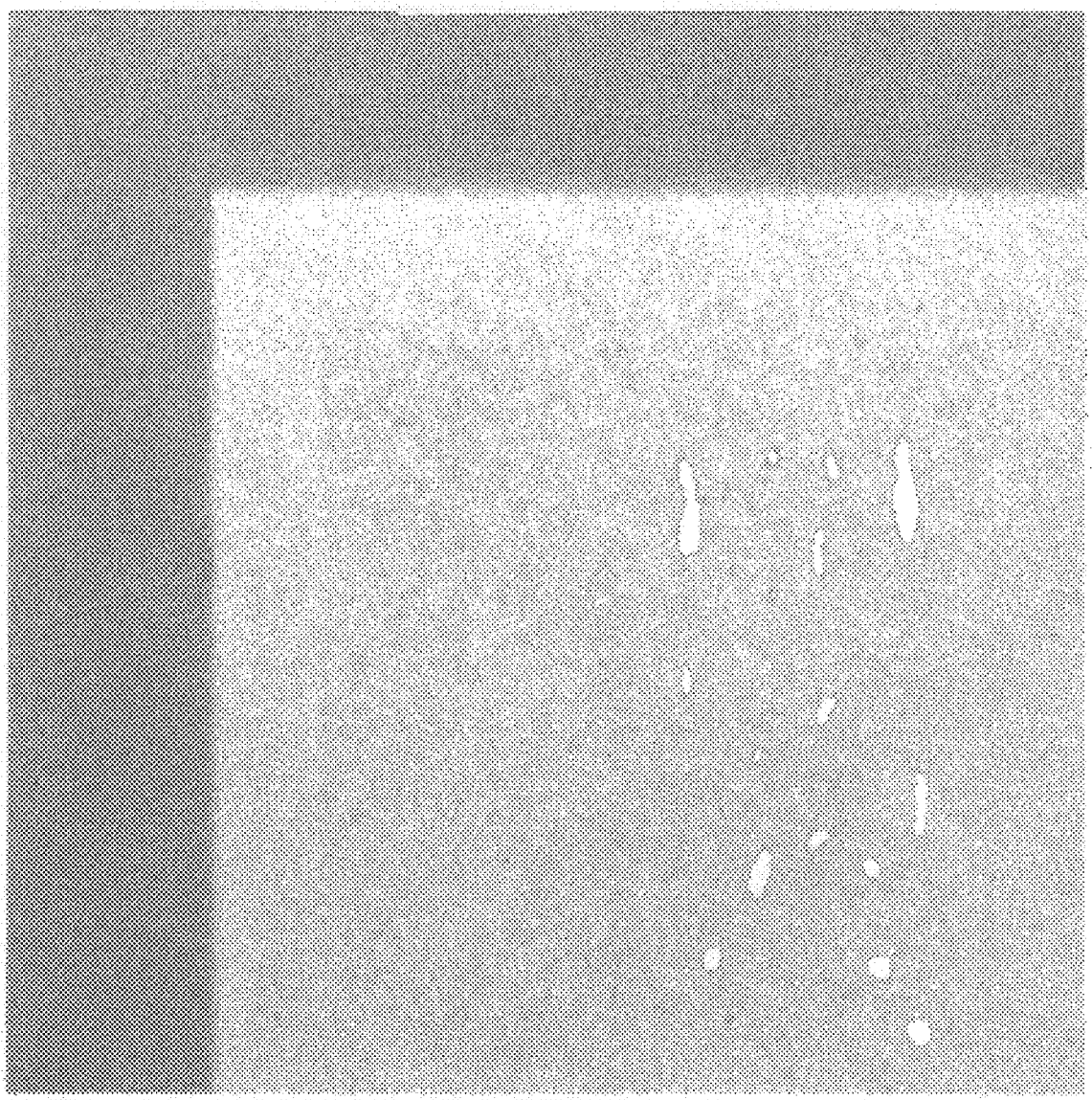
FIG. 53 illustrates in a clear coating application an exemplary superimposed void display image obtained from the void display image of FIG. 52.

Next, the number of times this subroutine has been performed is checked (3109). If this subroutine has been performed less than 10 times, the subroutine returns to (3103) and the operation is performed again. The effect from the operators perspective is to have blinking red blotches appear on the display monitor which indicate to the operator where coating voids exist. Returning to step (3109), if this subroutine has been performed 10 times, the Warning Beacon is turned off (3110) and exit the void error display subroutine. Monochrome images illustrating the warning images displayed to the operator are illustrated in FIG. 44 and FIG. 53 in the case of tinted coating and clear coating respectively. The white areas on the images represent void areas found in error.

Referencing the exemplary process overall block diagram of FIG. 20, if the results of the void size check (2006) as just described result in no error labels being copied to the ED, the coating void detection software is exited and control returns to the calling user interface software.

Software Application Environment

Aspects of the function of the present invention may be embodied in a wide variety of forms, but one presently preferred embodiment has components which are significantly controlled by application software. This software is conventionally loaded into a personal computer for operation and may reside on floppy disk, hard disk, or some other mass storage device. When in actual operation, this software may reside in the main computer system random access memory (RAM) or some other storage means for use with the operational computer.

The present invention program code software embodiments are envisioned to operate in a wide variety of operating system environments. However, several presently preferred embodiments make use of the Microsoft Windows NT 4.0 operating system or the like. For example, other operating systems such as UNIX and its variants as well as virtual memory based operating systems would be suitable in this application. Furthermore, operating systems employing multiprocessor support, multitasking support, multiprogramming and/or multiprocessing support may be suitable in this application. One advantage in this application available with the Microsoft Windows NT 4.0 operating system is the ability to support multiple processors. Microsoft Windows NT is also a fully virtual environment, which is helpful when working with large image data captures such as are present in many exemplary embodiments of the present invention (RTP using 768×512×3×8-bit images which consume 1.2 MB per image).

Embodiments of software used to implement the teachings of the present invention have been successfully implemented using Microsoft C++ and C programming languages under Revision 5.0 of the Microsoft Visual C++ development platform utilizing Microsoft Foundation Classes.

These examples are by no means limitive of the development tools, platforms and/or operating systems on which the teachings of the present invention may be implemented, but may be of use to individuals who desire to generate embodiments of the teachings of the present invention.

PREFERRED SYSTEM CONTEXT OF THE PRESENT INVENTION

The numerous innovative teachings of the present application will be described with particular reference to the presently preferred embodiments, wherein these innovative teachings are advantageously applied to the particular problems of a SYSTEM AND METHOD FOR MONITORING AND CONTROLLING THE DEPOSITION OF PATTERN AND OVERALL MATERIAL COATINGS. However, it should be understood that these embodiments are only one example of the many advantageous uses of the innovative teachings herein. In general, statements made in the specification of the present application do not necessarily limit any of the various claimed inventions. Moreover, some statements may apply to some inventive features but not to others.

Coating Applications

The application of coatings on continuous webs covers a wide range of manufacturing processes. Usually the coating has a mechanical property where voids often called pinholes create the most significant potential for causing defective material. Microscopic pinholes or voids are present in all coating operations. It is only when they reach a specific size that they cause defective material. The present invention provides a means whereby the size of pinholes can be accurately determined. This allows the detection of the size of the pinholes or voids which if corrected prevent waste material.

A few of the categories in which the present invention may be utilized to generate a new class of coating technologies have reliabilities far beyond the performance of existing technologies will now be discussed.

Registered Cold Seals

Traditional product packaging operations have used hot wax and/or hot glue to perform sealing functions. This function typically required a back-end machine specifically designed to apply the hot sealant to the finished product package. This method of product packaging is currently being replaced by 'cold seal' techniques in which the a room temperature sealant is applied to the product packaging as part of the normal printing/coating operation. This permits elimination of the costly and unreliable hot sealant machines which have heretofore been used in the packaging industry. However, the key to implementing a successful cold seal in the packaging industry is the control of the seal registration (alignment on the product package) as well as the quality and reliability of the cold seal, which relate directly to control of the voids/pinholes present in the cold seal coating. This is one of the objectives of the present invention.

It must be mentioned that registered cold seals currently experience wide use, and a partial application list may include the following exemplary situations:
1. packaging for an increasing number of food products (foodstuffs) such as candy and bread, where this method of package sealing is replacing hot glue;
2. medical packaging of items such as surgical instruments and medical supplies that require a sterile package sealing bond;
3. airline baggage tickets and the like which are coated with a cold seal to permit semi-permanent attachment of the ticket to the baggage.

While these sealing applications may seem somewhat routine, the first two can have significant health/safety ramifications if not performed properly.

For example, voids in the cold seal of foodstuffs can permit air to enter the foodstuff package, causing the product to go stale. More importantly, the foodstuff product could be contaminated and actually cause death or serious injury to the person ingesting the foodstuff product. The recent use of resealable cold seals in foodstuff product packaging only increases the need for this type of coating to be rigorously inspected for excessive voids, as in this application the cold seal is repeatedly opened and resealed as the foodstuff product is removed from the bag at various intervals in time.

Similarly, the failure of a cold seal in a packaged medical instrument or supply (pill, bandage, etc.) can result in the product becoming nonsterile, the result being a possibly deadly infection resulting from the contamination of the medical instrument and/or supply. Thus, these sealing applications as well as a whole host of others require tight monitoring of the voids in the cold seal coatings. The present invention permits this type of rigorous inspection to be performed and as a result generates a class of seal coating which is quantitatively more reliable than that which can be achieved using traditional inspection methods.

Registered Ton Lacquer and/or Varnish in Packaging Materials

Clear lacquer or varnish is currently used to protect or enhance the visual effect of products such as cigarettes, detergent, and disposable diapers to name a few exemplary items. Registration of these materials is important as glue will not adhere to areas with lacquer or varnish and these areas must remain free of coating. The present invention permits registration of the coatings to be accurately maintained across variations in the manufacturing process.

Coated Colored Papers

Pinholes or voids in coated colored papers affect the aesthetic value of the coating, and thus it is important to maintain tight controls over these pinhole sizes. The present invention permits a level of control which is not possible using the manual means of the prior art.

Adhesive Coatings

Adhesive coatings may be used in many applications, such as in bonding vinyl to a fabric as in the manufacture of convertible tops or lamination of aluminum foil, vinyl, film, and other substrates to a second substrate where voids in the bond produce delamination in use.

The tight control of voids in this type of manufacturing process produces an end product with significantly higher reliability and long-term wear characteristics than that which can be produced by the inspection techniques of the prior art. Thus, by using the present invention to monitor material voids, the resulting end product has different functional characteristics than its counterpart which is inspected solely using manual methods. The reason for this is that it is generally impossible for an operator to accurately and consistently perform visual inspections at the rate and with the accuracy of the present invention. Additionally, the optional use of a feedback control means to adjust manufacturing parameters such as the solvent-solid ratio and impression pressure may be done continuously by the present invention at a rate which is far more responsive than that possible using a manual operator.

Special Coatings

Special coatings may be used in a wide variety of applications, such as in film manufacture with coating of the emulsion and coatings to insulate minute contacts in the manufacture of touch screens. These applications are typically characterized by an overall requirement for tight control of void sizes as well as a corresponding high material waste should these controls not be properly and continuously monitored. The present invention addresses the needs of this manufacturing environment in that the inspections can be performed once every 2–3 seconds which permits trends in void/pinhole sizes to be determined and corrected long before material waste occurs because of excessive void/pinhole sizes.

Waste Prevention and Reliability Considerations

One aspect of the present invention which tends to create product of a different kind than that of the prior art inspection techniques is the issue of waste prevention and reliability. As mentioned previously, a typical coating process may be operating on 4-foot wide rolls of material which travel at 1000 linear feet/minute past the inspection station. Furthermore, the presence of voids/pinholes in the coating that is being inspected is usually a progressive process. That is to say, minute voids/pinholes are present in all manufactured product, but there exists a critical size at which these voids/pinholes impact product reliability.

This trend from void/pinhole sizes which may be ignored to those which impact product quality and reliability is a primary advantage of the present invention over the prior art. Since the present system can detect void/pinhole sizes on the order of 0.001 inch, minute changes in the rate of pinhole size can be tracked. This permits the operator to be notified long in advance of the appearance of voids/pinholes in the manufactured product which will impact the product quality or generate product waste. As mentioned previously, this also permits automatic feedback means to be employed with the present invention to automatically adjust the manufacturing process and thus reverse the trend from smaller-to-larger void/pinhole sizes.

This concentration on reliability has critical implications in the sealing of medical instruments and/or supplies in sterile environments as well as contamination control in the packaging of foodstuffs. Several of the exemplary embodiments of the present invention make use of roving image capture devices to sample and inspect the coating across the width of a web surface (RTP using camera systems which have a 4-inch square image capture area), but other configurations are possible as well. For example, using linear cameras and/or sensors it would be possible using the teachings of the present invention to continuously inspect the entire width of the web, rather than sample specific areas along the web width. This particular application of the present invention teachings is specifically envisioned for a wide variety of applications where the coating process must be continuously and rigorously monitored. Such applications, as well as others which may be supported by a roving image capture device (which performs a statistical process monitoring function), are beyond the inspection capabilities of the manual methods of the prior art.

In all web coating applications mentioned herein, the issue of reliability is inextricably linked with reduction in product waste. For example, by the time most operators notice that there is a void problem in a given web coating process, product waste already occurred. This means that some of the manufactured product must be scrapped, and furthermore that some portion of the material which is not scrapped may be unreliable. To what extent this is the case is a highly product- and manufacturing-dependent issue. However, suffice it to say the confidence level of the resulting manufactured product is not as high as it should be. In contrast, the present invention provides immediate feedback to the operator and optionally to the manufacturing process itself to correct the trend in increasing voids/pinholes which are observed in the manufactured product. Since the trends in void/pinhole size can be automatically calculated, is possible to reverse these trends with appropriate feedback to ensure both a reliable manufactured product as well as a manufactured product with minimum waste. As mentioned previously, many of the critical coating applications are more concerned with coating reliability than product waste, and the issue of product reliability is a much more rigorous inspection standard than that of product waste.

CONCLUSION

While only a few exemplary embodiments of the present invention have been described above, it will be clear to one skilled in the art that the teachings and scope of the present invention are quite broad and may be deduced by inspection from the foregoing detailed description. To aid in this process, the generalized pictorial of FIG. 60 has been provided and will now be discussed.

Figure 60:
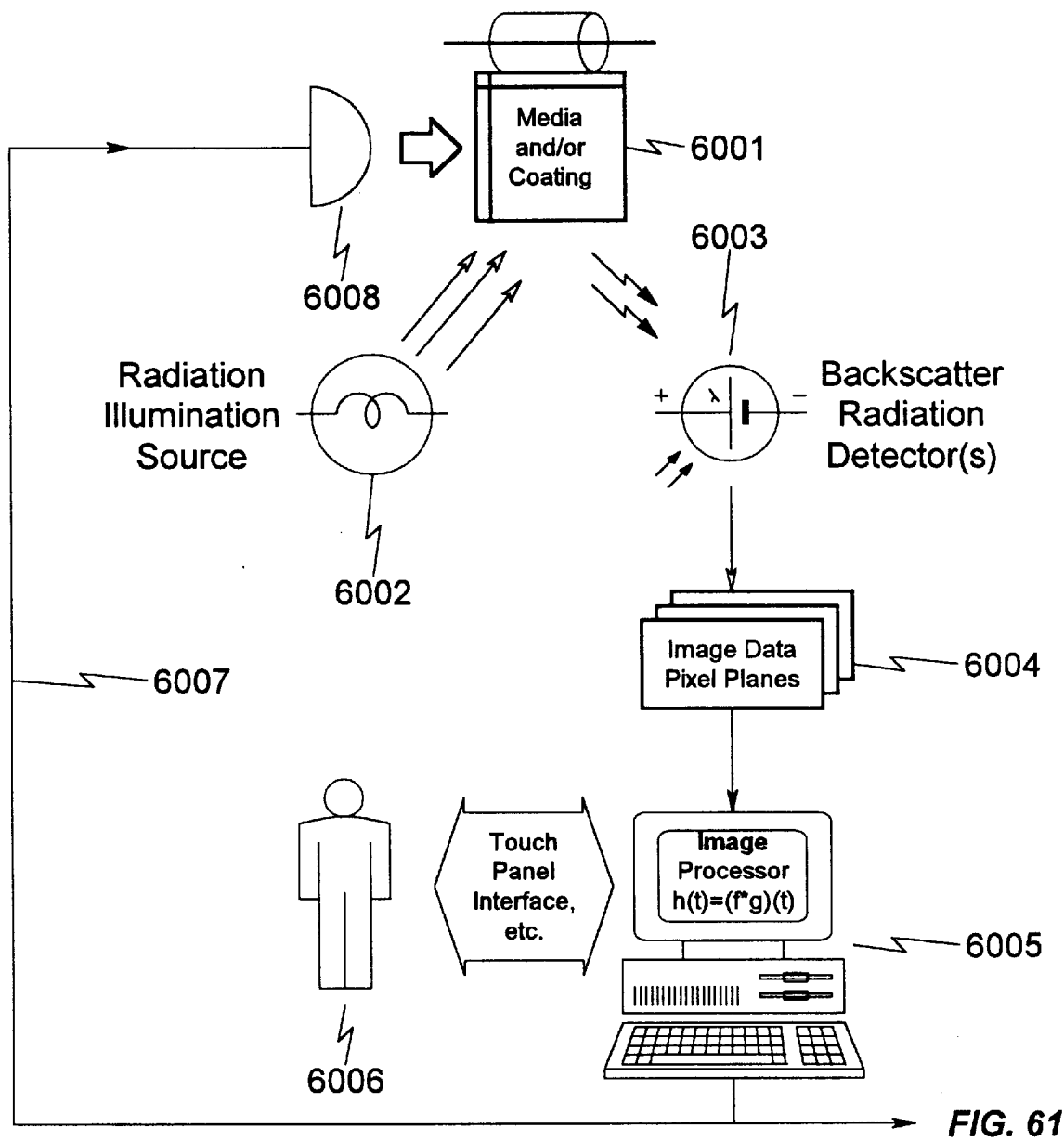
FIG. 60 illustrates a generalized system overview of the teachings of the present invention.

Referencing FIG. 60, at its most fundamental level the present invention teaches that drastically improved material coatings can be obtained by illuminating the media and/or coating (6001) with a source of radiation illumination (6002) and then detecting the backscatter radiation with a detector (6003), converting this information to one or more image pixel planes of data (6004), processing this image data with an image processor (6005), and then informing an operator (6006) of the detection of voids/pinholes in the media coating and/or optionally issuing some form of manufacturing process feedback (6007) to control some mechanical aspect of the coating deposition process (6008). As mentioned previously, this optional feedback control can provide a wide degree of modulation of the manufacturing process at a speed and with a granularity not presently possible with a manual operator.

Figure 61:
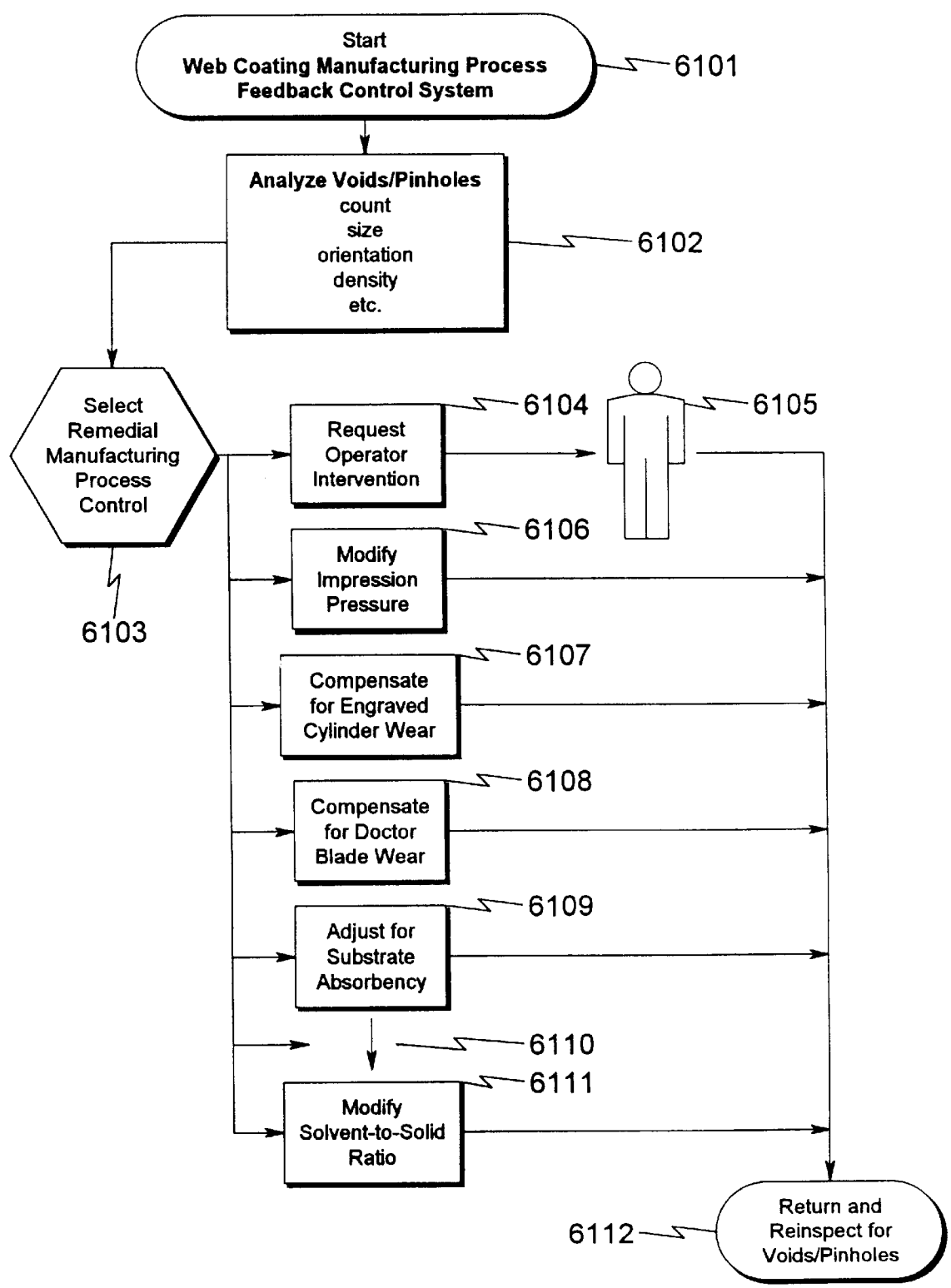
FIG. 61 illustrates a number of exemplary process control feedback controls which may be present in some embodiments of the present invention, and which generalize one of many methods of web coating process control taught by the present invention.

Examples of possible feedback control schemes mentioned previously are illustrated in FIG. 61 which shows how the stylized feedback path (6007) of FIG. 60 may be in fact a control system for a multiple number of mechanized manufacturing controls. Each of these adjustments are normally performed by an operator, but may be integrated in to the void/pinhole control system described herein. An exemplary feedback process control system as illustrated by the exemplary process flowchart of FIG. 61 starts with an entrypoint (6101) at which may be invoked at the detection of web coating voids or lack thereof. These voids/pinholes are then analyzed (6102) and categorized for use by a software selection algorithm (6103) which selects the appropriate remedial process control actions based on the types of voids detected. These may include a wide variety of actions, such as requesting operator intervention (6104) in which an operator (6105) is prompted to take a specific or general action; modifying the impression pressure (6106); compensating for engraved cylinder wear (6107); compensating for doctor blade wear (6108); adjusting for substrate absorbency (6109); modifying the solvent-to-solid ratio (6111); or providing for some other process-specific action (6110). Once these actions are taken, the process control returns and reinspects the web coating (6112) in an attempt to verify that these remedial actions were effective in correcting the problem. Of course, this feedback control scheme is amenable to a wide variety of possible embodiments, and may include neural net, systolic array, or other types of goal-seeking processor architectures in an attempt to optimize the process control monitoring function.

What must be stressed in viewing the generalized flowchart of FIG. 60 is that the coating quality and reliability possible with the present invention is of a different kind than currently possible with existing manual operator inspection methods. While current manual operator methods are aimed at preventing waste, the present invention provides continuous feedback and trend analysis to permit elimination of waste by keeping voids/pinholes within acceptable limits prior to waste occurring. Furthermore, the much more stringent requirements associated with generating a reliable web coating require that much narrower tolerances for void/pinhole sizes be maintained, which is typically not possible with existing manual operator inspection methods. Thus, the quality levels possible with coatings produced by the instant invention system and method permit coating materials to be used in situations where it would be imprudent or unsafe to use existing manual operator inspection, such as in many food, medical instrument, medical supply, and similar packaging operations where quality must be rigorously controlled and enforced.

Therefore, the present invention specifically envisions the use of the enhanced cold seals possible with the system and method of the present invention as they apply to product packaging. Furthermore, the specific application of these improved cold seals to the packaging of foodstuffs, candy, medical instruments, medical supplies, medicines, pills, convertible tops, and any other application in which the integrity, quality, or reliability of the cold seal must be held to a high quality level is specifically envisioned by the teachings of the present invention.

Although a preferred embodiment of the present invention has been illustrated in the accompanying Drawings and described in the foregoing Detailed Description, it will be understood that the invention is not limited to the embodiments disclosed, but is capable of numerous rearrangements, modifications, and substitutions without departing from the spirit of the invention as set forth and defined by the following claims.

What is claimed is:

1. A method for monitoring and/or controlling the deposition of pattern and/or overall material coatings comprising the steps of:

(a) Illuminating a material coating with a radiation source to generate backscattered radiation;

(b) Acquiring an input RGB image from said backscattered radiation;

(c) Building a monochrome image from said input RGB image;

(d) Generating an enhanced image from said monochrome image;

(e) Generating a dilated image from said enhanced image;

(f) Generating a lowpass image from said dilated image;

(g) Generating a thresholded image from said lowpass image;

(h) Generating an inverted image from said thresholded image;

(i) Saving only coating voids in said inverted image;

(j) Superimposing said coating voids on said monochrome image.

2. The method of claim 1 wherein said radiation source is a strobe light.

3. The method of claim 1 wherein said radiation source is infrared radiation (IR).

4. The method of claim 1 wherein said radiation source is ultraviolet radiation (UV).

5. A method for monitoring and/or controlling the deposition of pattern and/or overall material coatings comprising the steps of:

(a) Illuminating a material coating with a radiation source to generate backscattered radiation;

(b) Acquiring an input intensity image from said backscattered radiation;

(c) Generating an enhanced image from said intensity image;

(d) Generating a dilated image from said enhanced image;

(e) Generating a lowpass image from said dilated image;

(f) Generating a thresholded image from said lowpass image;

(g) Generating an inverted image from said thresholded image;

(h) Saving only coating voids in said inverted image; and (i) Superimposing said coating voids on said monochrome image.

6. The method of claim 5 wherein said radiation source is a strobe light.

7. The method of claim 5 wherein said radiation source is infrared radiation (IR).

8. The method of claim 5 wherein said radiation source is ultraviolet radiation (W).

9. A method for monitoring and/or controlling the deposition of pattern and/or overall material coatings comprising the steps of:

a) Illuminating a material coating with a radiation source to generate backscattered radiation;

b) Acquiring an input intensity image from said backscattered radiation; and, c) Image processing said intensity image to detect voids in said deposition pattern and/or overall material coating, wherein said image processing step further comprises generating an enhanced image from said intensity image, wherein said image processing step further comprises generating a dilated image from said enhanced image, and wherein said image processing step further comprises generating a lowpass image from said dilated image.

10. The method of claim 9 wherein said image processing step further comprises generating a thresholded image from said lowpass image.

11. The method of claim 10 wherein said image processing step further comprises generating an inverted image from said thresholded image.

12. The method of claim 11 wherein said image processing step further comprises saving only coating voids in said inverted image.

13. The method of claim 12 wherein said image processing step further comprises superimposing said coating voids on said intensity image.

* * * * *